US012617857B2

(12) United States Patent
Yan et al.

(10) Patent No.: US 12,617,857 B2
(45) Date of Patent: May 5, 2026

(54) CHEMOKINE RECEPTOR 4 (CXCR4) ANTAGONIST ANTIBODIES

(71) Applicant: REMD Biotherapeutics, Inc., Camarillo, CA (US)

(72) Inventors: Hai Yan, Thousand Oaks, CA (US); John Zhang, Camarillo, CA (US)

(73) Assignee: REMD Biotherapeutics, Inc, Camarillo, CA (US)

( * ) Notice: Subject to any disclaimer, the term of this patent is extended or adjusted under 35 U.S.C. 154(b) by 742 days.

(21) Appl. No.: 17/920,534

(22) PCT Filed: Apr. 22, 2021

(86) PCT No.: PCT/US2021/028583
§ 371 (c)(1),
(2) Date: Oct. 21, 2022

(87) PCT Pub. No.: WO2021/216832
PCT Pub. Date: Oct. 28, 2021

(65) Prior Publication Data
US 2023/0151104 A1 May 18, 2023

Related U.S. Application Data

(60) Provisional application No. 63/014,602, filed on Apr. 23, 2020.

(51) Int. Cl.
| | |
|---|---|
| *A61P 35/00* | (2006.01) |
| *A61K 39/00* | (2006.01) |
(Continued)

(52) U.S. Cl.
CPC .......... *C07K 16/2866* (2013.01); *A61P 35/00* (2018.01); *C12N 15/63* (2013.01);
(Continued)

(58) Field of Classification Search
CPC .......... C07K 16/2866; C07K 2317/565; C07K 2317/567; C07K 2317/92; C07K 2317/24;
(Continued)

(56) References Cited

U.S. PATENT DOCUMENTS

| | | | |
|---|---|---|---|
| 7,682,611 B2 | 3/2010 | Hanai et al. | |
| 9,708,405 B2 * | 7/2017 | Liu ......................... | A61P 11/00 |
(Continued)

OTHER PUBLICATIONS

Koenig P, Lee CV, Walters BT, et al. Mutational landscape of antibody variable domains reveals a switch modulating the interdomain conformational dynamics and antigen binding. Proc Natl Acad Sci U S A. 2017;114(4):E486-E495. (Year: 2017).*
(Continued)

*Primary Examiner* — Joanne Hama
*Assistant Examiner* — Hannah Sunshine
(74) *Attorney, Agent, or Firm* — Craig A Crandall, APC; Craig A Crandall

(57) ABSTRACT

This application provides isolated antibodies, and antigen-binding fragments thereof that specifically bind chemokine receptor 4 (CXCR4). These CXCR4 antibodies, or antigen-binding fragments thereof, have a high affinity for CXCR4, function to effectively block SDF-1 binding to CXCR4, thereby inhibiting forskolin stimulated cAMP with low nM IC50, are less immunogenic compared to their unmodified parent antibodies in a given species (e.g., in a human), and can be used to treat CXCR4-associated disorders while avoiding the adverse side effects associated with the current CXCR4 antagonist therapies.

14 Claims, 5 Drawing Sheets

Specification includes a Sequence Listing.

(51) Int. Cl.
    *C07K 16/28*         (2006.01)
    *C12N 15/63*        (2006.01)

(52) U.S. Cl.
    CPC ........ *A61K 39/00* (2013.01); *C07K 2317/565*
        (2013.01); *C07K 2317/567* (2013.01); *C07K*
                                *2317/92* (2013.01)

(58) Field of Classification Search
    CPC . C07K 2317/56; C07K 2317/76; A61P 35/00;
                         C12N 15/63; A61K 39/00
    See application file for complete search history.

(56)                   References Cited

U.S. PATENT DOCUMENTS

| | | |
|---|---|---|
| 11,312,777 B2 | 4/2022 | Kuhne et al. |
| 2014/0363455 A1 | 12/2014 | Stull et al. |
| 2015/0037328 A1 | 2/2015 | Liu et al. |

OTHER PUBLICATIONS

Rabia LA, Desai AA, Jhajj HS, Tessier PM. Understanding and overcoming trade-offs between antibody affinity, specificity, stability and solubility. Biochem Eng J. Sep. 15, 2018;137:365-374. (Year: 2018).*

* cited by examiner

| | #8 | #15 | #17 |
|---|---|---|---|
| IC50 | 0.3805 | 1.178 | 1.478 |

| | C3683CA130-VH1+VL1 | C3683CA130-VH1+VL3 | C3683CA130-VH1+VL2 | C3683CA130-chimeric | Human IgG |
|---|---|---|---|---|---|
| EC50 | 1.599 | 1.718 | 2.345 | 1.799 | ~1702 |

| | VH1+VL1 | VH+VL | VH1+VL2 | VH1+VL3 |
|---|---|---|---|---|
| IC50 | 20.69 | 21.37 | 95.4 | 21.51 |

SEQUENCE LISTING

```
<160> NUMBER OF SEQ ID NOS: 43

<210> SEQ ID NO 1
<211> LENGTH: 360
<212> TYPE: PRT
<213> ORGANISM: Homo sapiens

<400> SEQUENCE: 1

Met Glu Gly Ile Ser Ser Ile Pro Leu Pro Leu Leu Gln Ile Tyr Thr
1               5                   10                  15

Ser Asp Asn Tyr Thr Glu Glu Met Gly Ser Gly Asp Tyr Asp Ser Met
            20                  25                  30

Lys Glu Pro Cys Phe Arg Glu Glu Asn Ala Asn Phe Asn Lys Ile Phe
        35                  40                  45

Leu Pro Thr Ile Tyr Ser Ile Ile Phe Leu Thr Gly Ile Val Gly Asn
    50                  55                  60

Gly Leu Val Ile Leu Val Met Gly Tyr Gln Lys Lys Leu Arg Ser Met
65                  70                  75                  80

Thr Asp Lys Tyr Arg Leu His Leu Ser Val Ala Asp Leu Leu Phe Val
                85                  90                  95

Ile Thr Leu Pro Phe Trp Ala Val Asp Ala Val Ala Asn Trp Tyr Phe
            100                 105                 110

Gly Asn Phe Leu Cys Lys Ala Val His Val Ile Tyr Thr Val Asn Leu
        115                 120                 125

Tyr Ser Ser Val Leu Ile Leu Ala Phe Ile Ser Leu Asp Arg Tyr Leu
    130                 135                 140

Ala Ile Val His Ala Thr Asn Ser Gln Arg Pro Arg Lys Leu Leu Ala
145                 150                 155                 160
```

-continued

```
Glu Lys Val Val Tyr Val Gly Val Trp Ile Pro Ala Leu Leu Leu Thr
            165             170             175

Ile Pro Asp Phe Ile Phe Ala Asn Val Ser Glu Ala Asp Asp Arg Tyr
            180             185             190

Ile Cys Asp Arg Phe Tyr Pro Asn Asp Leu Trp Val Val Val Phe Gln
            195             200             205

Phe Gln His Ile Met Val Gly Leu Ile Leu Pro Gly Ile Val Ile Leu
    210             215             220

Ser Cys Tyr Cys Ile Ile Ile Ser Lys Leu Ser His Ser Lys Gly His
225             230             235             240

Gln Lys Arg Lys Ala Leu Lys Thr Thr Val Ile Leu Ile Leu Ala Phe
            245             250             255

Phe Ala Cys Trp Leu Pro Tyr Tyr Ile Gly Ile Ser Ile Asp Ser Phe
            260             265             270

Ile Leu Leu Glu Ile Ile Lys Gln Gly Cys Glu Phe Glu Asn Thr Val
            275             280             285

His Lys Trp Ile Ser Ile Thr Glu Ala Leu Ala Phe Phe His Cys Cys
    290             295             300

Leu Asn Pro Ile Leu Tyr Ala Phe Leu Gly Ala Lys Phe Lys Thr Ser
305             310             315             320

Ala Gln His Ala Leu Thr Ser Val Ser Arg Gly Ser Ser Leu Lys Ile
            325             330             335

Leu Ser Lys Gly Lys Arg Gly Gly His Ser Ser Val Ser Thr Glu Ser
            340             345             350

Glu Ser Ser Ser Phe His Ser Ser
            355             360
```

```
<210> SEQ ID NO 2
<211> LENGTH: 5
<212> TYPE: PRT
<213> ORGANISM: Mus musculus

<400> SEQUENCE: 2

Ser Ser Gly Met His
1               5

<210> SEQ ID NO 3
<211> LENGTH: 10
<212> TYPE: PRT
<213> ORGANISM: Mus musculus

<400> SEQUENCE: 3

Gly Tyr Ala Phe Thr Asp Phe His Leu Asn
1               5               10

<210> SEQ ID NO 4
<211> LENGTH: 17
<212> TYPE: PRT
<213> ORGANISM: Mus musculus

<400> SEQUENCE: 4

Tyr Ile Ser Ser Gly Ser Ser Ser Ile Tyr Tyr Ala Asp Thr Val Lys
1               5               10              15

Gly

<210> SEQ ID NO 5
<211> LENGTH: 17
<212> TYPE: PRT
```

-continued

```
<213> ORGANISM: Mus musculus

<400> SEQUENCE: 5

Val Ile Asn Pro Tyr Asn Gly Gly Thr Asn Tyr Asn Gln Lys Phe Lys
1               5                   10                  15

Asp

<210> SEQ ID NO 6
<211> LENGTH: 11
<212> TYPE: PRT
<213> ORGANISM: Mus musculus

<400> SEQUENCE: 6

Pro Tyr Tyr Tyr Gly Ser Ile Ala Met Asp Tyr
1               5                   10

<210> SEQ ID NO 7
<211> LENGTH: 12
<212> TYPE: PRT
<213> ORGANISM: Mus musculus

<400> SEQUENCE: 7

Tyr Tyr Ala Ser Arg Tyr Gly Tyr Ala Met Asp Tyr
1               5                   10

<210> SEQ ID NO 8
<211> LENGTH: 11
<212> TYPE: PRT
<213> ORGANISM: Mus musculus

<400> SEQUENCE: 8

Lys Ala Ser Gln Asp Ile Asn Ser Tyr Leu Ser
1               5                   10

<210> SEQ ID NO 9
<211> LENGTH: 16
<212> TYPE: PRT
<213> ORGANISM: Mus musculus

<400> SEQUENCE: 9

Arg Ser Ser Lys Ser Leu Leu His Ser Asn Gly Asn Thr Tyr Leu Tyr
1               5                   10                  15

<210> SEQ ID NO 10
<211> LENGTH: 7
<212> TYPE: PRT
<213> ORGANISM: Mus musculus

<400> SEQUENCE: 10

Arg Ala Asn Arg Leu Val Asp
1               5

<210> SEQ ID NO 11
<211> LENGTH: 7
<212> TYPE: PRT
<213> ORGANISM: Mus musculus

<400> SEQUENCE: 11

Arg Met Ser Asn Leu Ala Ser
1               5

<210> SEQ ID NO 12
<211> LENGTH: 9
<212> TYPE: PRT
```

<213> ORGANISM: Mus musculus

<400> SEQUENCE: 12

Leu Gln Tyr Asp Glu Phe Pro Phe Thr
1               5

<210> SEQ ID NO 13
<211> LENGTH: 9
<212> TYPE: PRT
<213> ORGANISM: Mus musculus

<400> SEQUENCE: 13

Met Gln His Val Glu Tyr Pro Leu Thr
1               5

<210> SEQ ID NO 14
<211> LENGTH: 120
<212> TYPE: PRT
<213> ORGANISM: Mus musculus

<400> SEQUENCE: 14

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Ser
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ser Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Pro Tyr Tyr Tyr Gly Ser Ile Ala Met Asp Tyr Trp Gly Gln
            100                 105                 110

Gly Thr Ser Val Thr Val Ser Ser
        115                 120

<210> SEQ ID NO 15
<211> LENGTH: 360
<212> TYPE: DNA
<213> ORGANISM: Mus musculus

<400> SEQUENCE: 15
gatgtgcagc tggtggagtc tgggggaggc ttagtgcagc ctggagggtc ccggaaactc      60
tcctgtgcag cctctggatt cactttcagt agctctggaa tgcactgggt tcgtcaggct     120
ccagagaagg gactggagtg ggtcgcatac attagtagtg gcagtagttc catctactat     180
gcagacacag tgaagggccg attcaccatc tccagagaca atcccaagaa caccctgttc     240
ttgcaaatga ccagtctaag gtctgaggac acggccatgt attactgtgc aagaccttat     300
tactacggct ccattgctat ggactactgg ggtcaaggaa cctcagtcac cgtctcctca     360

<210> SEQ ID NO 16
<211> LENGTH: 121
<212> TYPE: PRT
<213> ORGANISM: Mus musculus

<400> SEQUENCE: 16

Glu Val Gln Leu Gln Gln Ser Gly Pro Val Leu Val Arg Pro Gly Ala

-continued

```
1               5                   10                  15
Ser Val Lys Met Ser Cys Lys Ala Ser Gly Tyr Ala Phe Thr Asp Phe
            20                  25                  30

His Leu Asn Trp Val Lys Gln Ser His Gly Lys Ser Leu Glu Trp Ile
        35                  40                  45

Gly Val Ile Asn Pro Tyr Asn Gly Gly Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Asn Arg Leu Thr Ser Glu Asp Ser Ala Val Tyr Tyr Cys
                85                  90                  95

Ala Arg Tyr Tyr Ala Ser Arg Tyr Gly Tyr Ala Met Asp Tyr Trp Gly
            100                 105                 110

Gln Gly Thr Ser Val Thr Val Ser Ser
        115                 120
```

```
<210> SEQ ID NO 17
<211> LENGTH: 363
<212> TYPE: DNA
<213> ORGANISM: Mus musculus

<400> SEQUENCE: 17
gaggtccaac tgcaacagtc tggacctgtg ctggtgaggc ctggggcttc agtgaagatg      60
tcctgtaagg cttctggata cgcattcact gacttccatt tgaactgggt gaagcagagc     120
catggaaaga gccttgagtg gattggagtt attaatcctt acaacggtgg tactaactac     180
aaccagaagt tcaaggacaa ggccacattg actgttgaca gtcctccag cacagcctac      240 atggagctca acagactgac atctgaggac tctgcagtct attactgtgc aagatactac     300
gctagtaggt acggctatgc tatggactac tggggtcaag aacctcagt caccgtctcc      360 tca                                                                    363
```

```
<210> SEQ ID NO 18
<211> LENGTH: 107
<212> TYPE: PRT
<213> ORGANISM: Mus musculus

<400> SEQUENCE: 18

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Phe
                85                  90                  95

Thr Phe Gly Ser Gly Thr Lys Leu Glu Ile Lys
            100                 105
```

```
<210> SEQ ID NO 19
<211> LENGTH: 321
<212> TYPE: DNA
<213> ORGANISM: Mus musculus
```

<400> SEQUENCE: 19

```
gacatcaaga tgacccagtc tccatcttcc atgtatgcat ctctaggaga gagagtcact      60
atcacttgca aggcgagtca ggacattaat agctatttaa gctggttcca gcagaaacca     120
gggaaatctc ctaagaccct gatctatcgt gcaaacagat tggtagatgg ggtcccatca     180
aggttcagtg gcagtggatc tgggcaagat tattctctca ccatcagcag cctggagtat     240
gaagatatgg gaatttatta ttgtctacag tatgatgagt ttccattcac gttcggctcg     300
gggacaaagt tggaaataaa a                                                321
```

<210> SEQ ID NO 20
<211> LENGTH: 112
<212> TYPE: PRT
<213> ORGANISM: Mus musculus

<400> SEQUENCE: 20

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Ile Tyr Tyr Cys Met Gln His
                85                  90                  95

Val Glu Tyr Pro Leu Thr Phe Gly Ala Gly Thr Lys Leu Glu Leu Lys
            100                 105                 110
```

<210> SEQ ID NO 21
<211> LENGTH: 336
<212> TYPE: DNA
<213> ORGANISM: Mus musculus

<400> SEQUENCE: 21

```
gatattgtga tgactcaggc tgcaccctct gtacctgtca ctcctggaga gtcagtatcc      60
atctcctgca ggtctagtaa gagtctcctg catagtaatg caacactta cttgtattgg      120 ttcctgcaga ggccaggcca gtctcctcag ctcctgatat atcggatgtc caaccttgcc     180
tcaggagtcc cagacaggtt cagtggcagt gggtcaggaa ctgctttcac actgagaatc     240
agtagagtgg aggctgagga tgtgggtatt tattattgta tgcaacatgt agaatatcct     300
ctcacgttcg gtgctgggac caagctggag ctgaaa                                336
```

<210> SEQ ID NO 22
<211> LENGTH: 470
<212> TYPE: PRT
<213> ORGANISM: Artificial
<220> FEATURE:
<223> OTHER INFORMATION: Heavy chain sequence of a murine-human chimeric
     antibody

<400> SEQUENCE: 22

```
Met Gly Trp Ser Cys Ile Ile Leu Phe Leu Val Ala Thr Ala Thr Gly
1               5                   10                  15

Val His Ser Glu Val Gln Leu Gln Gln Ser Gly Pro Val Leu Val Arg
```

```
                  20                    25                    30

Pro Gly Ala Ser Val Lys Met Ser Cys Lys Ala Ser Gly Tyr Ala Phe
            35                    40                    45

Thr Asp Phe His Leu Asn Trp Val Lys Gln Ser His Gly Lys Ser Leu
        50                    55                    60

Glu Trp Ile Gly Val Ile Asn Pro Tyr Asn Gly Thr Asn Tyr Asn
65                    70                    75                    80

Gln Lys Phe Lys Asp Lys Ala Thr Leu Thr Val Asp Lys Ser Ser Ser
                85                    90                    95

Thr Ala Tyr Met Glu Leu Asn Arg Leu Thr Ser Glu Asp Ser Ala Val
            100                   105                   110

Tyr Tyr Cys Ala Arg Tyr Tyr Ala Ser Arg Tyr Gly Tyr Ala Met Asp
            115                   120                   125

Tyr Trp Gly Gln Gly Thr Ser Val Thr Val Ser Ser Ala Ser Thr Lys
        130                   135                   140

Gly Pro Ser Val Phe Pro Leu Ala Pro Ser Ser Lys Ser Thr Ser Gly
145                   150                   155                   160

Gly Thr Ala Ala Leu Gly Cys Leu Val Lys Asp Tyr Phe Pro Glu Pro
                165                   170                   175

Val Thr Val Ser Trp Asn Ser Gly Ala Leu Thr Ser Gly Val His Thr
            180                   185                   190

Phe Pro Ala Val Leu Gln Ser Ser Gly Leu Tyr Ser Leu Ser Ser Val
            195                   200                   205

Val Thr Val Pro Ser Ser Ser Leu Gly Thr Gln Thr Tyr Ile Cys Asn
        210                   215                   220

Val Asn His Lys Pro Ser Asn Thr Lys Val Asp Lys Lys Val Glu Pro
225                   230                   235                   240

Lys Ser Cys Asp Lys Thr His Thr Cys Pro Pro Cys Pro Ala Pro Glu
                245                   250                   255

Leu Leu Gly Gly Pro Ser Val Phe Leu Phe Pro Pro Lys Pro Lys Asp
            260                   265                   270

Thr Leu Met Ile Ser Arg Thr Pro Glu Val Thr Cys Val Val Val Asp
            275                   280                   285

Val Ser His Glu Asp Pro Glu Val Lys Phe Asn Trp Tyr Val Asp Gly
        290                   295                   300

Val Glu Val His Asn Ala Lys Thr Lys Pro Arg Glu Glu Gln Tyr Asn
305                   310                   315                   320

Ser Thr Tyr Arg Val Val Ser Val Leu Thr Val Leu His Gln Asp Trp
                325                   330                   335

Leu Asn Gly Lys Glu Tyr Lys Cys Lys Val Ser Asn Lys Ala Leu Pro
            340                   345                   350

Ala Pro Ile Glu Lys Thr Ile Ser Lys Ala Lys Gly Gln Pro Arg Glu
            355                   360                   365

Pro Gln Val Tyr Thr Leu Pro Pro Ser Arg Asp Glu Leu Thr Lys Asn
        370                   375                   380

Gln Val Ser Leu Thr Cys Leu Val Lys Gly Phe Tyr Pro Ser Asp Ile
385                   390                   395                   400

Ala Val Glu Trp Glu Ser Asn Gly Gln Pro Glu Asn Asn Tyr Lys Thr
                405                   410                   415

Thr Pro Pro Val Leu Asp Ser Asp Gly Ser Phe Phe Leu Tyr Ser Lys
            420                   425                   430

Leu Thr Val Asp Lys Ser Arg Trp Gln Gln Gly Asn Val Phe Ser Cys
            435                   440                   445
```

```
Ser Val Met His Glu Ala Leu His Asn His Tyr Thr Gln Lys Ser Leu
    450                 455                 460

Ser Leu Ser Pro Gly Lys
465                 470

<210> SEQ ID NO 23
<211> LENGTH: 238
<212> TYPE: PRT
<213> ORGANISM: Artificial
<220> FEATURE:
<223> OTHER INFORMATION: Light chain sequence of a murine-human chimeric
      antibody

<400> SEQUENCE: 23

Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Pro Val
                20                  25                  30

Thr Pro Gly Glu Ser Val Ser Ile Ser Cys Arg Ser Ser Lys Ser Leu
            35                  40                  45

Leu His Ser Asn Gly Asn Thr Tyr Leu Tyr Trp Phe Leu Gln Arg Pro
        50                  55                  60

Gly Gln Ser Pro Gln Leu Leu Ile Tyr Arg Met Ser Asn Leu Ala Ser
65                  70                  75                  80

Gly Val Pro Asp Arg Phe Ser Gly Ser Gly Ser Gly Thr Ala Phe Thr
                85                  90                  95

Leu Arg Ile Ser Arg Val Glu Ala Glu Asp Val Gly Ile Tyr Tyr Cys
            100                 105                 110

Met Gln His Val Glu Tyr Pro Leu Thr Phe Gly Ala Gly Thr Lys Leu
        115                 120                 125

Glu Leu Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 24
<211> LENGTH: 121
<212> TYPE: PRT
<213> ORGANISM: Artificial
<220> FEATURE:
<223> OTHER INFORMATION: Humanized heavy chain variable region amino
      acid sequence

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asp Phe
                20                  25                  30
```

-continued

```
His Leu Asn Trp Val Arg Gln Ala Pro Gly Gln Gly Leu Glu Trp Met
    35                  40                  45

Gly Val Ile Asn Pro Tyr Asn Gly Gly Thr Asn Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Tyr Ala Ser Arg Tyr Gly Tyr Ala Met Asp Tyr Trp Gly
            100                 105                 110

Gln Gly Thr Leu Val Thr Val Ser Ser
        115                 120

<210> SEQ ID NO 25
<211> LENGTH: 121
<212> TYPE: PRT
<213> ORGANISM: Artificial
<220> FEATURE:
<223> OTHER INFORMATION: Humanized heavy chain variable region amino
      acid sequence

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asp Phe
                20                  25                  30

His Leu Asn Trp Val Arg Gln Ser Pro Gly Gln Gly Leu Glu Trp Ile
    35                  40                  45

Gly Val Ile Asn Pro Tyr Asn Gly Gly Thr Asn Tyr Asn Gln Lys Phe
    50                  55                  60

Lys Asp Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Tyr Ala Ser Arg Tyr Gly Tyr Ala Met Asp Tyr Trp Gly
            100                 105                 110

Gln Gly Thr Leu Val Thr Val Ser Ser
        115                 120

<210> SEQ ID NO 26
<211> LENGTH: 121
<212> TYPE: PRT
<213> ORGANISM: Artificial
<220> FEATURE:
<223> OTHER INFORMATION: Humanized heavy chain variable region amino
      acid sequence

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asp Phe
                20                  25                  30

His Leu Asn Trp Val Arg Gln Ser His Gly Gln Gly Leu Glu Trp Ile
    35                  40                  45

Gly Val Ile Asn Pro Tyr Asn Gly Gly Thr Asn Tyr Asn Gln Lys Phe
    50                  55                  60

Lys Asp Arg Val Thr Leu Thr Val Asp Thr Ser Ile Ser Thr Ala Tyr
65                  70                  75                  80
```

-continued

```
Met Glu Leu Ser Arg Leu Arg Ser Asp Asp Thr Ala Val Tyr Tyr Cys
                85                  90                  95

Ala Arg Tyr Tyr Ala Ser Arg Tyr Gly Tyr Ala Met Asp Tyr Trp Gly
            100                 105                 110

Gln Gly Thr Leu Val Thr Val Ser Ser
        115                 120

<210> SEQ ID NO 27
<211> LENGTH: 121
<212> TYPE: PRT
<213> ORGANISM: Artificial
<220> FEATURE:
<223> OTHER INFORMATION: Humanized heavy chain variable region amino
      acid sequence

<400> SEQUENCE: 27

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Ala Phe Thr Asp Phe
            20                  25                  30

His Leu Asn Trp Val Arg Gln Ser His Gly Gln Gly Leu Glu Trp Ile
        35                  40                  45

Gly Val Ile Asn Pro Tyr Asn Gly Gly Thr Asn Tyr Asn Gln Lys Phe
    50                  55                  60

Lys Asp Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Tyr Ala Ser Arg Tyr Gly Tyr Ala Met Asp Tyr Trp Gly
            100                 105                 110

Gln Gly Thr Leu Val Thr Val Ser Ser
        115                 120

<210> SEQ ID NO 28
<211> LENGTH: 121
<212> TYPE: PRT
<213> ORGANISM: Artificial
<220> FEATURE:
<223> OTHER INFORMATION: Humanized heavy chain variable region amino
      acid sequence

<400> SEQUENCE: 28

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Ala Phe Thr Asp Phe
            20                  25                  30

His Leu Asn Trp Val Lys Gln Ser His Gly Gln Gly Leu Glu Trp Ile
        35                  40                  45

Gly Val Ile Asn Pro Tyr Asn Gly Gly Thr Asn Tyr Asn Gln Lys Phe
    50                  55                  60

Lys Asp Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Tyr Ala Ser Arg Tyr Gly Tyr Ala Met Asp Tyr Trp Gly
            100                 105                 110

Gln Gly Thr Leu Val Thr Val Ser Ser
        115                 120
```

```
<210> SEQ ID NO 29
<211> LENGTH: 121
<212> TYPE: PRT
<213> ORGANISM: Artificial
<220> FEATURE:
<223> OTHER INFORMATION: Humanized heavy chain variable region amino
      acid sequence

<400> SEQUENCE: 29

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Ala Phe Thr Asp Phe
            20                  25                  30

His Leu Asn Trp Val Lys Gln Ser His Gly Gln Gly Leu Glu Trp Ile
        35                  40                  45

Gly Val Ile Asn Pro Tyr Asn Gly Gly Thr Asn Tyr Asn Gln Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Ser Ala Val Tyr Tyr Cys
                85                  90                  95

Ala Arg Tyr Tyr Ala Ser Arg Tyr Gly Tyr Ala Met Asp Tyr Trp Gly
            100                 105                 110

Gln Gly Thr Leu Val Thr Val Ser Ser
        115                 120

<210> SEQ ID NO 30
<211> LENGTH: 112
<212> TYPE: PRT
<213> ORGANISM: Artificial
<220> FEATURE:
<223> OTHER INFORMATION: Humanized light chain variable region amino
      acid sequence

<400> SEQUENCE: 30

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Val Glu Tyr Pro Leu Thr Phe Gly Gly Gly Thr Lys Leu Glu Ile Lys
            100                 105                 110

<210> SEQ ID NO 31
<211> LENGTH: 112
<212> TYPE: PRT
<213> ORGANISM: Artificial
<220> FEATURE:
<223> OTHER INFORMATION: Humanized light chain variable region amino
      acid sequence

<400> SEQUENCE: 31
```

-continued

```
Asp Ile Val Met Thr Gln Ser Pro Leu Ser Leu Pro Val Thr Pro Gly
1               5                   10                  15

Glu Pro Val Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
            85                  90                  95

Val Glu Tyr Pro Leu Thr Phe Gly Gly Gly Thr Lys Leu Glu Ile Lys
            100                 105                 110
```

```
<210> SEQ ID NO 32
<211> LENGTH: 112
<212> TYPE: PRT
<213> ORGANISM: Artificial
<220> FEATURE:
<223> OTHER INFORMATION: Humanized light chain variable region amino
      acid sequence

<400> SEQUENCE: 32
```

```
Asp Ile Val Met Thr Gln Ser Ala Leu Ser Leu Pro Val Thr Pro Gly
1               5                   10                  15

Glu Pro Val Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
            85                  90                  95

Val Glu Tyr Pro Leu Thr Phe Gly Gly Gly Thr Lys Leu Glu Ile Lys
            100                 105                 110
```

```
<210> SEQ ID NO 33
<211> LENGTH: 451
<212> TYPE: PRT
<213> ORGANISM: Artificial
<220> FEATURE:
<223> OTHER INFORMATION: Humanized heavy chain amino acid sequence

<400> SEQUENCE: 33
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asp Phe
            20                  25                  30

His Leu Asn Trp Val Arg Gln Ala Pro Gly Gln Gly Leu Glu Trp Met
        35                  40                  45

Gly Val Ile Asn Pro Tyr Asn Gly Gly Thr Asn Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
```

-continued

```
                    85                  90                  95
Ala Arg Tyr Tyr Ala Ser Arg Tyr Gly Tyr Ala Met Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450
```

<210> SEQ ID NO 34
<211> LENGTH: 1356
<212> TYPE: DNA
<213> ORGANISM: Artificial
<220> FEATURE:
<223> OTHER INFORMATION: Humanized heavy chain nucleic acid sequence -continued

```
<400> SEQUENCE: 34
caggtgcagc tggtgcagag cggagcagag gtgaagaagc caggagcctc cgtgaaggtg     60
tcttgcaagg ccagcggcta cgccttcacc gactttcacc tgaactgggt gcggcaggca    120
ccaggacagg gactggagtg gatgggcgtg atcaaccctt acaatggcgg cacaaactat    180
aatcagaagt tcaaggacag ggtgaccatg acacgcgata cctctatcag cacagcctac    240
atggagctgt cccggctgag atctgacgat accgccgtgt actattgtgc ccggtactat    300
gcctccagat acggctatgc catggattat tggggccagg gcaccctggt gacagtgagc    360
tccgccagca ccaagggccc ttccgtgttt ccactggccc cctcctctaa atccacatct    420
ggcggcaccg ccgccctggg ctgtctggtg aaggactact cccagagcc tgtgacagtg     480 tcctggaact ctggcgccct gacatccggc gtgcacacat ttccagccgt gctgcagagc    540
tccggcctgt acagcctgtc tagcgtggtg acagtgccct cctctagcct gggcacacag    600
acctatatct gcaacgtgaa tcacaagcca agcaatacca aggtggacaa gaaggtggag    660
cccaagtcct gtgataagac acacacctgc ccccccttgtc ctgctcccga gctgctgggc    720
ggccctagcg tgttcctgtt tccacccaag cctaaggaca ccctgatgat ctcccggaca    780
cccgaggtga cctgcgtggt ggtggacgtg tctcacgagg atcctgaggt gaagttcaac    840
tggtatgtgg atggcgtgga ggtgcacaat gccaagacca gcccagaga ggagcagtac     900 aactctacat atagggtggt gagcgtgctg accgtgctgc accaggactg gctgaacggc    960
aaggagtata agtgcaaggt gtccaataag gccctgcccg cccccatcga gaagacaatc   1020
agcaaggcca agggccagcc tcgggagcca caggtgtaca ccctgcctcc atccagagac   1080
gagctgacaa agaaccaggt gtctctgaca tgtctggtga agggcttcta tcctagcgat   1140
atcgccgtgg agtgggagtc caatggccag ccagagaaca attacaagac cacacccccct   1200 gtgctggact ccgatggctc cttctttctg tattccaagc tgaccgtgga taagtctcgg   1260
tggcagcagg gcaacgtgtt cagctgttcc gtgatgcacg aagccctgca taatcactat   1320
actcagaaat ccctgtccct gtcacctgga aagtga                           1356

<210> SEQ ID NO 35
<211> LENGTH: 219
<212> TYPE: PRT
<213> ORGANISM: Artificial
<220> FEATURE:
<223> OTHER INFORMATION: Humanized light chain amino acid sequence

<400> SEQUENCE: 35

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Val Glu Tyr Pro Leu Thr Phe Gly Gly Gly Thr Lys Leu Glu Ile Lys
            100                 105                 110
```

-continued

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 36
<211> LENGTH: 660
<212> TYPE: DNA
<213> ORGANISM: Artificial
<220> FEATURE:
<223> OTHER INFORMATION: Humanized light chain nucleic acid sequence

<400> SEQUENCE: 36
gacatcgtga tgacccagtc ccctctgtct ctgcccgtga cacctggcga gccagcctct      60
atcagctgca ggagctccaa gagcctgctg cactccaacg gcaataccta cctgtattgg     120
tacctgcaga gcccggcca gtcccctcag ctgctgatct atcggatgtc taacctggcc     180
agcggcgtgc cagacagatt ctccggatct ggaagcggaa ccgacttcac cctgaagatc     240
tctcgggtgg aggccgagga tgtgggcgtg tactattgta tgcagcacgt ggagtaccca     300
ctgaccttcg gcggaggaac aaagctggag atcaagagga cagtggccgc cccaagcgtg     360
ttcatctttc cccttccga cgagcagctg aagtctggca ccgccagcgt ggtgtgcctg     420
ctgaacaact ctaccctcg ggaggccaag gtccagtgga aggtggataa cgccctgcag     480
tctggcaata gccaggagtc cgtgaccgag caggactcta aggatagcac atattccctg     540
tctagcaccc tgacactgag caaggccgat tacgagaagc acaaggtgta tgcctgtgaa     600
gtcacccatc aggggctgtc atcacccgtc actaagtcat tcaatcgcgg agaatgctag     660
```

```
<210> SEQ ID NO 37
<211> LENGTH: 219
<212> TYPE: PRT
<213> ORGANISM: Artificial
<220> FEATURE:
<223> OTHER INFORMATION: Humanized light chain amino acid sequence

<400> SEQUENCE: 37
```

```
Asp Ile Val Met Thr Gln Ser Pro Leu Ser Leu Pro Val Thr Pro Gly
1               5                   10                  15

Glu Pro Val Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
```

```
                  85                  90                  95

Val Glu Tyr Pro Leu Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 38
<211> LENGTH: 660
<212> TYPE: DNA
<213> ORGANISM: Artificial
<220> FEATURE:
<223> OTHER INFORMATION: Humanized light chain nucleic acid sequence

<400> SEQUENCE: 38
gacatcgtga tgacccagtc ccctctgtct ctgcccgtga cacctggcga gccagtgtct      60
atcagctgca ggagctccaa gagcctgctg cactccaacg gcaatacctact cctgtattgg     120 ttcctgcaga agcccggcca gtcccctcag ctgctgatct accggatgtc taacctggcc     180
agcggcgtgc cagacagatt ctccggatct ggaagcggaa ccgacttcac cctgaagatc     240
tctcgggtgg aggccgagga tgtgggcgtg tactattgta tgcagcacgt ggagtatccc     300
ctgacctttg gcggcggcac aaagctggag atcaagagga cagtggccgc cccaagcgtg     360
ttcatctttc cccttccga cgagcagctg aagtctggca ccgccagcgt ggtgtgcctg     420
ctgaacaact ctaccctcg ggaggccaag gtccagtgga aggtggataa cgccctgcag     480
tctggcaata gccaggagtc cgtgaccgag caggactcta aggatagcac atattccctg     540
tctagcaccc tgacactgag caaggccgat tacgagaagc acaaggtgta tgcctgtgaa     600
gtcacccatc aggggctgtc atcacccgtc actaagtcat tcaatcgcgg agaatgctag     660

<210> SEQ ID NO 39
<211> LENGTH: 219
<212> TYPE: PRT
<213> ORGANISM: Artificial
<220> FEATURE:
<223> OTHER INFORMATION: Humanized heavy chain amino acid sequence

<400> SEQUENCE: 39

Asp Ile Val Met Thr Gln Ser Ala Leu Ser Leu Pro Val Thr Pro Gly
1               5                   10                  15

Glu Pro Val Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60
```

-continued

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Val Glu Tyr Pro Leu Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 40
<211> LENGTH: 660
<212> TYPE: DNA
<213> ORGANISM: Artificial
<220> FEATURE:
<223> OTHER INFORMATION: Humanized heavy chain nucleic acid sequence

<400> SEQUENCE: 40
gacatcgtga tgacccagtc cgccctgtct ctgccagtga cacctggaga gccagtgtct     60
atcagctgca ggagctccaa gagcctgctg cactccaacg caataccta cctgtattgg     120 ttcctgcaga agcccggcca gtcccctcag ctgctgatct accggatgtc taacctggcc     180
agcggcgtgc cagacagatt ctccggatct ggaagcggaa ccgacttcac cctgaagatc     240
tctcgggtgg aggccgagga tgtgggcgtg tactattgta tgcagcacgt ggagtatccc     300
ctgacctttg gcggcggcac aaagctggag atcaagagga cagtggccgc cccaagcgtg     360
ttcatctttc ccccttccga cgagcagctg aagtctggca ccgccagcgt ggtgtgcctg     420
ctgaacaact ctaccctcg ggaggccaag gtccagtgga aggtggataa cgccctgcag     480
tctggcaata gccaggagtc cgtgaccgag caggactcta aggatagcac atattccctg     540
tctagcaccc tgacactgag caaggccgat tacgagaagc acaaggtgta tgcctgtgaa     600
gtcacccatc aggggctgtc atcacccgtc actaagtcat tcaatcgcgg agaatgctag     660
```

```
<210> SEQ ID NO 41
<211> LENGTH: 107
<212> TYPE: PRT
<213> ORGANISM: Homo sapiens

<400> SEQUENCE: 41

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

```
Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 42
<211> LENGTH: 106
<212> TYPE: PRT
<213> ORGANISM: Homo sapiens

<400> SEQUENCE: 42

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
                100                 105

<210> SEQ ID NO 43
<211> LENGTH: 330
<212> TYPE: PRT
<213> ORGANISM: Homo sapiens

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

-continued

```
Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
        275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330
```

CHEMOKINE RECEPTOR 4 (CXCR4) ANTAGONIST ANTIBODIES

RELATED PATENT APPLICATIONS

This application is a U.S. National Stage Application pursuant to 35 U.S.C. § 371 of PCT/US2021/028583, filed Apr. 22, 2021, which claims benefit of U.S. Provisional Application No. 63/014,602, filed on Apr. 23, 2020, incorporated in its entirety by reference herein.

TECHNICAL FIELD

Chemokines (chemoattractant cytokines) are comprised of a family of structurally and functionally related polypeptides with 8-10 kilodaltons. Chemokines are involved in diverse biological functions including regulation of immune cell proliferation, migration, activation, differentiation and homing. The biological activities of chemokines are mediated by a family of 7-transmembrane G-protein coupled receptors (GPCRs). One member of the chemokine receptor family is CXCR4 which is specific for chemokine CXCL12 (also known as stromal-derived-factor-1 (SDF-1)). SDF-1 binding to CXCR4 activates a cascade of signaling molecules including suppression of cAMP, activation of phospholipase C and intracellular calcium flux (Mukaida et al., Exp Cell Res., 318(2):95-102, 2012). SDF-1 is expressed on a wide variety of human tissues, including liver, lungs, bone marrow, lymph nodes, stromal and endothelial cells. Similarly, CXCR4 is found in various tissues with predominant expression on lymphocytes (Zhou et al., Curr Med Chem., 26 (17): 3026-3041, 2019). Human genetic studies support the concept that increased CXCR4 activity is associated with compromised immune system and increased risks of cancer and other immunodeficiency diseases.

Overexpression of CXCR4 has been found in 75% of solid and hematopoietic cancers, including pancreatic, lung, breast, ovarian, prostate and colorectal tumors, leukemias and lymphomas (Zlotnik et al., Homeostatic chemokine receptors and organ-specific metastasis. Nat Rev Immunol., 11(9):597-606, 2011). Activation of CXCR4 by CXCL12 stimulates various signaling pathways that promote chemotaxis, adhesion, migration, cell proliferation and survival (Balkwill et al., J Pathol., 226(2):148-157, 2012). The downstream effectors of CXCR4/SDF-1, including PI3 kinase, Ras, stress-activated protein kinase (SAPK), c-Jun N-terminal kinase (JNK), phospholipase C (PLC), mitogen-activated protein kinase (MAPK), p38 MAPK and AKT are involved in tumor cell proliferation, migration and metastasis. Both SDF-1 and CXCR4 were identified in cancer stem cells (CSC), a population of tumor cells that drive carcinogenesis and resistant to conventional cancer therapies (Larzabal et al., Plos one, 8(11) e79798, 2013). In clinical studies, CXCR4 has been associated with increased propensity for metastasis and decreased survival and greater expression of CXCR4 correlates with disease severity (Spano et al., Ann Oncol, 15:613-7, 2004).

Immunotherapy using agonistic, antagonistic, or blocking antibodies to co-stimulatory or co-inhibitory molecules (immune checkpoints) has been an area of extensive research and clinical evaluation. Immune checkpoint proteins include CTLA-4, PD-1, PD-L1, LAG-3, and TIM-3 as well as several others (Sharpe et al., Nat Immunol, 8:239-45, 2007). Under normal physiological conditions, immune checkpoints are crucial for the maintenance of self-tolerance (that is, the prevention of autoimmunity) and protect tissues from damage when the immune system is responding to pathogenic infection. It is now also clear that tumors co-opt certain immune-checkpoint pathways as a major mechanism of immune resistance, particularly against T cells that are specific for tumor antigens (Pardoll D M., Nat Rev Cancer, 12:252-64, 2012). Accordingly, treatment utilizing antibodies to immune checkpoint molecules including, e.g., CTLA-4 (ipilimumab), PD-1 (nivolumab; pembrolizumab; pidilizumab) and PD-L1 (BMS-936559; MPLD3280A; MED14736; MSB0010718C)(see, e.g, Philips and Atkins, International Immunology, 27(1); 39-46, October 2014), and OX-40, CD137, GITR, LAGS, TIM-3, and VISTA (see, e.g., Sharon et al., Chin J Cancer., 33(9): 434-444, September 2014; Hodi et al., N Engl J Med, 2010; Topalian et al., N Engl J Med, 366:2443-54) are being evaluated as new, alternative immunotherapies to treat patients with proliferative diseases such as cancer, and in particular, patients with refractory and/or recurrent cancers.

Currently, checkpoint inhibitor therapy has become the preferred second- or third-line therapy for many cancers, and PD1/PDL1 antibodies have changed the treatment paradigm for several cancers. Despite these significant advancements, there remains a major need to improve on the current state-of-the-art. For example, checkpoint inhibitor therapy remains limited by concerns over potential severe side effects and the fact that many tumors lack the targeted antigen and will therefore evade treatment. In general, about 20% of patients with various cancers respond to PD-1/PD-L1 antibodies or CTLA-4 antibodies and overall survival remains less than a year in most instances and objective response rates are modest, underscoring the large unmet need for nearly 70-80% of these patients.

In preclinical glioblastoma animal studies, combination of anti-PD-1 and anti-CXCR4 mAb treatment demonstrated a significant survival benefit compared to control and monotherapy arms. Tumor bearing mice that received combination therapy demonstrated immune memory and decreased populations of immunosuppressive tumor infiltrating leukocytes (Wu et al., Journal of Neuro-Oncology., 143:241-249, 2019). It thus appears that anti-CXCR4 mAb upon combination with anti-PD-1/PDL1 agents may provide additional antitumor activity and meet an important unmet need in the treatment of patients with solid tumors resistant to current immunotherapy.

Aberrant CXCR4 expression by genetic and somatic mutations is also the reported causes of two rare diseases, Waldenstrom Macroglobulinemia (WM) and WHIM syndrome. Waldenstrom Macroglobulinemia (WM) is a rare form of non-Hodgkin's lymphoma which affects about 2700 patients per year in the US. The mutations in CXCR4 led to its overexpression on cell membranes and overactivation of the receptor signaling pathways Poulain et al., Clin Cancer Res., 22(6) 1480-1488, 2016). WHIM syndrome is a congenital immune deficiency inherited in an autosomal dominant manner which affects young children. Individuals affected by WHIM are more susceptible to life-threating bacterial and viral infections. Chronic viral infections combined with neutropenia (low levels of circulating neutrophils) and hypogammaglobulinemia (low levels of certain antibodies) were reported to be the causes of lymphoma and carcinoma developed in some affected individuals with WHIM syndrome. To date, there are no approved therapeutics to treat the underline genetic causes of WHIM and WM. The present inventors propose that inhibitors of CXCR4 may be promising therapeutic agents for the treatment of rare disorders such as WHIM and WM.

DISCLOSURE OF THE INVENTION

In accordance with the present invention, there are provided isolated antibodies, and antigen-binding fragments thereof, that specifically bind chemokine receptor 4 (CXCR4). These CXCR4 antibodies, or antigen-binding fragments thereof, have a high affinity for CXCR4, function to effectively block SDF-1 binding to CXCR4, thereby inhibiting forskolin stimulated cAMP with low nM $IC_{50}$, are less immunogenic compared to their unmodified parent antibodies in a given species (e.g., in a human), and can be used to treat CXCR4-associated disorders. Importantly, compared to small molecule CXCR4 antagonists, the antibodies of the present invention have advantages of longer serum half-life, higher target specificity, thereby limiting the risk of off-target toxicity and improving therapeutic window.

In various embodiments, the antibody or antigen-binding fragment is selected from a human antibody, a humanized antibody, chimeric antibody, a monoclonal antibody, a polyclonal antibody, a recombinant antibody, a single chain antibody, a diabody, a triabody, a tetrabody, a Fab fragment, a Fab' fragment, a $Fab_2$ fragment, a $F(ab)'_2$ fragment, a domain antibody, an IgD antibody, an IgE antibody, an IgM antibody, an IgG1 antibody, an IgG2 antibody, an IgG3 antibody, an IgG4 antibody, or an IgG4 antibody having at least one mutation in the hinge region that alleviates a tendency to form intra H-chain disulfide bonds. In various embodiments, the antibody is a chimeric antibody. In various embodiments, the antibody is a humanized antibody. In various embodiments, the antibody is a fully human antibody. In various embodiments, isolated antibodies, and antigen-binding fragments thereof, that have a high affinity for the human CXCR4 of SEQ ID NO: 1 are provided.

In various embodiments, the antibody or antigen-binding fragment binds to CXCR4 protein with a dissociation constant ($K_D$) of at least about $1 \times 10^{-6}$ M, at least about $1 \times 10^{-7}$ M, at least about $1 \times 10^{-8}$ M, at least about $1 \times 10^{-9}$ M, at least about $1 \times 10^{-10}$ M, at least about $1 \times 10^{-11}$ M, or at least about $1 \times 10^{-12}$ M.

In various embodiments, an isolated antibody or antigen-binding fragment thereof of the present invention binds to human CXCR4 and comprises either: (a) a light chain CDR3 sequence identical, substantially identical or substantially similar to a CDR3 sequence selected from SEQ ID NOs: 12-13; (b) a heavy chain CDR3 sequence identical, substantially identical or substantially similar to a CDR3 sequence selected from SEQ ID NOs: 6-7; or (c) the light chain CDR3 sequence of (a) and the heavy chain CDR3 sequence of (b).

In various embodiments, the isolated antibody or antigen-binding fragment further comprises an amino acid sequence selected from: (d) a light chain CDR1 sequence identical, substantially identical or substantially similar to a CDR1 sequence selected from SEQ ID NOs: 8-9; (e) a light chain CDR2 sequence identical, substantially identical or substantially similar to a CDR2 sequence selected from SEQ ID NOs: 10-11; (f) a heavy chain CDR1 sequence identical, substantially identical or substantially similar to a CDR1 sequence selected from SEQ ID NOS: 2-3; (g) a heavy chain CDR2 sequence identical, substantially identical or substantially similar to a CDR2 sequence selected from SEQ ID NOs: 4-5; (h) the light chain CDR1 sequence of (d) and the heavy chain CDR1 sequence of (f); or (i) the light chain CDR2 sequence of (e) and the heavy chain CDR2 sequence of (g).

In various embodiments, the isolated human monoclonal antibody or antigen-binding fragment thereof of the present invention binds to human CXCR4 and comprises: (a) a light chain CDR1 sequence identical, substantially identical or substantially similar to a CDR1 sequence selected from SEQ ID NOs: 8-9; (b) a light chain CDR2 sequence identical, substantially identical or substantially similar to a CDR2 sequence selected from SEQ ID NOs: 10-11; (c) a light chain CDR3 sequence identical, substantially identical or substantially similar to a CDR3 sequence selected from SEQ ID NOs: 12-13; (d) a heavy chain CDR1 sequence identical, substantially identical or substantially similar to a CDR1 sequence selected from SEQ ID NOS: 2-3; (e) a heavy chain CDR2 sequence identical, substantially identical or substantially similar to a CDR2 sequence selected from SEQ ID NOs: 4-5; and (f) a heavy chain CDR3 sequence identical, substantially identical or substantially similar to a CDR3 sequence selected from SEQ ID NOs: 6-7.

In various embodiments, the isolated human monoclonal antibody or antigen-binding fragment thereof of the present invention binds to human CXCR4 and comprises: (a) a light chain CDR1 sequence identical, substantially identical or substantially similar to SEQ ID NO: 8; (b) a light chain CDR2 sequence identical, substantially identical or substantially similar to SEQ ID NO: 10; (c) a light chain CDR3 sequence identical, substantially identical or substantially similar to SEQ ID NO: 12; (d) a heavy chain CDR1 sequence identical, substantially identical or substantially similar to SEQ ID NO: 2; (e) a heavy chain CDR2 sequence identical, substantially identical or substantially similar to SEQ ID NO: 4; and (f) a heavy chain CDR3 sequence identical, substantially identical or substantially similar to SEQ ID NO: 6.

In various embodiments, the isolated human monoclonal antibody or antigen-binding fragment thereof of the present invention binds to human CXCR4 and comprises: (a) a light chain CDR1 sequence identical, substantially identical or substantially similar to SEQ ID NO: 9; (b) a light chain CDR2 sequence identical, substantially identical or substantially similar to SEQ ID NO: 11; (c) a light chain CDR3 sequence identical, substantially identical or substantially similar to SEQ ID NO: 13; (d) a heavy chain CDR1 sequence identical, substantially identical or substantially similar to SEQ ID NO: 3; (e) a heavy chain CDR2 sequence identical, substantially identical or substantially similar to SEQ ID NO: 5; and (f) a heavy chain CDR3 sequence identical, substantially identical or substantially similar to SEQ ID NO: 7.

In various embodiments, an isolated antibody or antigen-binding fragment thereof of the present invention binds to human CXCR4 and comprises either: (a) a heavy and/or light chain variable domain(s), the variable domain(s) having a set of three light chain CDR1, CDR2, and CDR3 identical, substantially identical or substantially similar to SEQ ID NOs: 8-9, 10-11, and 12-13, and/or a set of three heavy chain CDR1, CDR2, and CDR3 identical, substantially identical or substantially similar to SEQ ID NOS: 2-3, 4-5, and 6-7; and (b) a set of four variable region framework regions from a human immunoglobulin (IgG). In various embodiments, the antibody can optionally include a hinge region. In various embodiments, the framework regions are chosen from human germline exon $X_H$, $J_H$, $V_K$ and $J_K$ sequences. In various embodiments, the antibody is a fully humanized antibody. In various embodiments, the antibody is a fully human antibody.

In various embodiments, an isolated antibody or antigen-binding fragment thereof of the present invention binds to human CXCR4 and comprises the heavy chain variable region having the amino acid sequence set forth in SEQ ID NO: 14 and the light chain variable region having the amino acid sequence set forth in SEQ ID NO: 18. In various embodiments, an isolated antibody or antigen-binding fragment thereof of the present invention binds to human CXCR4 and comprises the heavy chain variable region having the amino acid sequence set forth in SEQ ID NO: 16 and the light chain variable region having the amino acid sequence set forth in SEQ ID NO: 20.

In various embodiments, the isolated antibody or antigen-binding fragment, when bound to human CXCR4: (a) binds to human CXCR4 with substantially the same or greater Kd as a reference antibody; (b) competes for binding to human CXCR4 with said reference antibody; or (c) is less immunogenic in a human subject than said reference antibody, wherein said reference antibody comprises a combination of heavy chain variable domain and light chain variable domain sequences selected from SEQ ID NOs: 14/18 and 16/20.

In various embodiments, an isolated humanized antibody or antigen-binding fragment thereof of the present invention binds to human CXCR4 and comprises a heavy chain variable region having a sequence identical, substantially identical or substantially similar to SEQ ID NOs: 24-29, and a light chain variable region having the sequence identical, substantially identical or substantially similar to SEQ ID NOs: 30-32.

In various embodiments, the isolated antibody or antigen-binding fragment, when bound to human CXCR4: (a) binds to human CXCR4 with substantially the same or greater Kd as a reference antibody; (b) competes for binding to human CXCR4 with said reference antibody; or (c) is less immunogenic in a human subject than said reference antibody, wherein said reference antibody comprises the combination of heavy chain variable domain and light chain variable domain sequences set forth in SEQ ID NOs: 24 and 30.

In various embodiments, an isolated humanized antibody or antigen-binding fragment thereof of the present invention binds to human CXCR4 and comprises a heavy chain having a sequence identical, substantially identical or substantially similar to SEQ ID NOs: 33, and a light chain variable region having the sequence identical, substantially identical or substantially similar to SEQ ID NOs: 35, 37 and 39. In various embodiments, an isolated humanized antibody or antigen-binding fragment thereof of the present invention binds to human CXCR4 and comprises the heavy chain sequence set forth in SEQ ID NO: 33, and the light chain sequence set forth in SEQ ID NO: 35. In various embodiments, an isolated humanized antibody or antigen-binding fragment thereof of the present invention binds to human CXCR4 and comprises the heavy chain sequence set forth in SEQ ID NO: 33, and the light chain sequence set forth in SEQ ID NO: 37. In various embodiments, an isolated humanized antibody or antigen-binding fragment thereof of the present invention binds to human CXCR4 and comprises the heavy chain sequence set forth in SEQ ID NO: 33, and the light chain sequence set forth in SEQ ID NO: 39.

In another aspect, the present invention relates to a pharmaceutical composition comprising an isolated antibody or antigen-binding fragment of the present invention in admixture with a pharmaceutically acceptable carrier. In various embodiments, the pharmaceutical composition comprises an isolated human antibody in admixture with a pharmaceutically acceptable carrier. In various embodiments, the pharmaceutical composition is formulated for administration via a route selected from the group consisting of subcutaneous injection, intraperitoneal injection, intramuscular injection, intrasternal injection, intravenous injection, intraarterial injection, intrathecal injection, intraventricular injection, intraurethral injection, intracranial injection, intrasynovial injection or via infusions.

In another aspect, the present invention relates to methods of treating a subject suffering from a CXCR4-associated disorder, comprising administering to said subject a therapeutically effective amount of an antibody or antigen-binding fragment thereof of the present invention. In various embodiments, the subject is a human subject. In various embodiments, the CXCR4-associated disorder is selected from the group consisting of cancer, WM, and WHIM.

In another aspect, the present invention relates to methods for treating cancer in a subject, comprising administering to the subject a therapeutically effective amount (either as monotherapy or in a combination therapy regimen) of an isolated antibody or antigen-binding fragment of the present invention. In another aspect, the present invention relates to methods for enhancing the immune response to cancerous cells in a subject, comprising administering to the subject a therapeutically effective amount (either as monotherapy or in a combination therapy regimen) of an isolated antibody or antigen-binding fragment of the present invention. In various embodiments, the present invention provides for a method of treating cancerous cells in a subject, comprising administering to said subject a therapeutically effective amount (either as monotherapy or in a combination therapy regimen) of an antibody or antigen-binding fragment thereof of the present invention. In various embodiments, the cancerous cell is selected from the group consisting of ovarian cancer, lung cancer, breast cancer, gastric cancer, prostate cancer, colon cancer, renal cell cancer, glioblastoma, and melanoma.

In various embodiments, the subject previously responded to treatment with an anti-cancer therapy, but, upon cessation of therapy, suffered relapse (hereinafter "a recurrent cancer"). In various embodiments, the subject has resistant or refractory cancer. In various embodiments, the cancerous cells are immunogenic tumors (e.g., those tumors for which vaccination using the tumor itself can lead to immunity to tumor challenge).

In another aspect, the present invention relates to combination therapies designed to treat a cancer in an subject, comprising administering to the subject a therapeutically effective amount of an isolated antibody or antigen-binding fragment of the present invention, and b) one or more additional therapies selected from the group consisting of immunotherapy, chemotherapy, small molecule kinase inhibitor targeted therapy, surgery, radiation therapy, and stem cell transplantation, wherein the combination therapy provides increased cell killing of tumor cells, i.e., a synergy exists between the isolated antibody or antigen-binding fragment and the additional therapies when co-administered.

In another aspect, an isolated immunoconjugate or fusion protein comprising an antibody or antigen-binding fragment conjugated to, linked to (or otherwise stably associated with) an effector molecule is provided. In various embodiments, the effector molecule is an immunotoxin, cytokine, chemokine, therapeutic agent, or chemotherapeutic agent.

In another aspect, the antibodies or antigen-binding fragments disclosed herein may be covalently linked to (or otherwise stably associated with) an additional functional moiety, such as a label or a moiety that confers desirable pharmacokinetic properties. In various embodiments, the label is selected from the group consisting of: a fluorescent label, a radioactive label, and a label having a distinctive nuclear magnetic resonance signature.

In another aspect, the present invention provides a method for detecting in vitro or in vivo the presence of human CXCR4 peptide in a sample, e.g., for diagnosing a human CXCR4-associated disorder.

In another aspect, isolated nucleic acids comprising the polynucleotide sequence that encodes the antibodies or antigen-binding fragments disclosed herein are provided. In various embodiments, the polynucleotide comprises a heavy chain sequence as set forth in SEQ ID NO: 34 a light chain sequence as set forth in SEQ ID NOs: 36, 38 and 40, or both. Also provided are expression vectors comprising the nucleic acid of the present invention. Also provided are isolated cells comprising the expression vectors of the invention. In various embodiments, the cell is a host cell comprising an expression vector of the present invention. In various embodiments, the cell is a hybridoma, wherein the chromosome of the cell comprises a nucleic acid of the present invention. Further provided is a method of making the antibody or antigen-binding fragment of the present invention comprising culturing or incubating the cell under conditions that allow the cell to express the antibody or antigen-binding fragment of the present invention.

MODE(S) OF CARRYING OUT THE INVENTION

Figure 1:
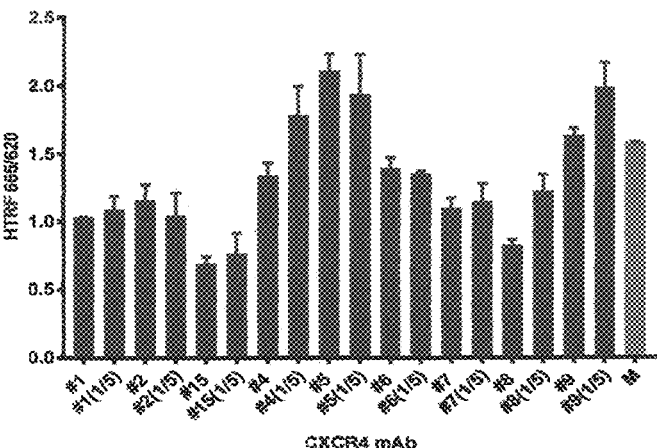
FIG. 1 is a bar graph depicting the CXCR4 cAMP functional assay data for murine mAbs #1-#9.

The present invention relates to antigen binding proteins such as antibodies, or antigen-binding fragments thereof that specifically bind to human CXCR4. In one aspect, there are provided isolated antibodies, and antigen-binding fragments thereof, that specifically bind CXCR4, have a high affinity for CXCR4, function to inhibit CXCR4, are less immunogenic compared to their unmodified parent antibodies in a given species (e.g., a human), and can be used to treat human disorders mediated by CXCR4. Also provided are nucleic acid molecules, and derivatives and fragments thereof, comprising a sequence of polynucleotides that encode all or a portion of a polypeptide that binds to CXCR4, such as a nucleic acid encoding all or part of an anti-CXCR4 antibody, antibody fragment, or antibody derivative. Also provided are vectors and plasmids comprising such nucleic acids, and cells or cell lines comprising such nucleic acids and/or vectors and plasmids. Also provided are methods of making, identifying, or isolating antigen binding proteins that bind to human CXCR4, such as anti-CXCR4 antibodies, methods of determining whether an antigen binding protein binds to CXCR4, methods of making compositions, such as pharmaceutical compositions, comprising an antigen binding protein that binds to human CXCR4, and methods for administering an antibody, or antigen-binding fragment thereof that binds CXCR4 to a subject, for example, methods for treating a condition mediated by CXCR4.

DEFINITIONS

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those commonly used and well known in the art. The methods and techniques of the present invention are generally performed according to conventional methods well known in the art and as described in various general and more specific references that are cited and discussed throughout the present specification unless otherwise indicated. See, e.g., Green and Sambrook, Molecular Cloning: A Laboratory Manual, 4th ed., Cold Spring Harbor Laboratory Press, Cold Spring Harbor, N.Y. (2012), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those commonly used and well known in the art. Standard techniques are used for chemical syntheses, chemical analyses, pharmaceutical preparation, formulation, and delivery, and treatment of subjects.

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular section of a polypeptide can be designated by amino acid residue number such as amino acids 80 to 119, or by the actual residue at that site such as Ser80 to Ser119. A particular polypeptide or polynucleotide sequence also can be described based upon how it differs from a reference sequence. Polynucleotide and polypeptide sequences of particular light and heavy chain variable domains are designated L1 ("light chain variable domain 1") and H1 ("heavy chain variable domain 1"). Antibodies comprising a light chain and heavy chain are indicated by combining the name of the light chain and the name of the heavy chain variable domains. For example, "L4H7," indicates, for example, an antibody comprising the light chain variable domain of L4 and the heavy chain variable domain of H7.

The term "antibody" is used herein to refer to a protein comprising one or more polypeptides substantially or partially encoded by immunoglobulin genes or fragments of immunoglobulin genes and having specificity to a tumor antigen or specificity to a molecule overexpressed in a pathological state. The recognized immunoglobulin genes include the kappa, lambda, alpha, gamma, delta, epsilon and mu constant region genes, as well as subtypes of these genes and myriad of immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition.

In a full-length antibody, each heavy chain is comprised of a heavy chain variable region (abbreviated herein as HCVR or VH) and a heavy chain constant region. The heavy chain constant region is comprised of three domains, CH1, CH2 and CH3 (and in some instances, CH4). Each light chain is comprised of a light chain variable region (abbreviated herein as LCVR or VL) and a light chain constant region. The light chain constant region is comprised of one domain, $C_L$. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The extent of the framework region and CDRs has been defined. The sequences of the framework regions of different light or heavy chains are relatively conserved within a species, such as humans. The framework region of an antibody, that is the combined framework regions of the constituent light and heavy chains, serves to position and align the CDRs in three-dimensional space. Immunoglobulin molecules can be of any type (e.g., IgG, IgE, IgM, IgD, IgA and IgY), class (e.g., IgG1, IgG2, IgG 3, IgG4, IgA1 and IgA2) or subclass.

The CDRs are primarily responsible for binding to an epitope of an antigen. The CDRs of each chain are typically referred to as CDR1, CDR2, CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

The Kabat definition is a standard for numbering the residues in an antibody and is typically used to identify CDR regions. The Kabat database is now maintained online and CDR sequences can be determined, for example, see IMGT/V-QUEST programme version: 3.2.18 Mar. 29, 2011, available on the internet and Brochet, X. et al., Nucl. Acids Res. 36, W503-508, 2008). The Chothia definition is similar to the Kabat definition, but the Chothia definition takes into account positions of certain structural loop regions. See, e.g., Chothia et al., J. Mol. Biol., 196: 901-17, 1986; Chothia et al., Nature, 342: 877-83, 1989. The AbM definition uses an integrated suite of computer programs produced by Oxford Molecular Group that model antibody structure. See, e.g., Martin et al., Proc. Natl. Acad. Sci. USA, 86:9268-9272, 1989; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198, 1999. The contact definition is based on an analysis of the available complex crystal structures. See, e.g., MacCallum et al., J. Mol. Biol., 5:732-45, 1996.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. The Fc portion of an antibody mediates several important effector functions e.g. cytokine induction, ADCC, phagocytosis, complement dependent cytotoxicity (CDC) and half-life/clearance rate of antibody and antigen-antibody complexes (e.g., the neonatal FcR (FcRn) binds to the Fc region of IgG at acidic pH in the endosome and protects IgG from degradation, thereby contributing to the long serum half-life of IgG). Replacements of amino acid residues in the Fc portion to alter antibody effector function are known in the art (see, e.g., Winter et al., U.S. Pat. Nos. 5,648,260 and 5,624,821).

Antibodies exist as intact immunoglobulins or as a number of well characterized fragments. Such fragments include Fab fragments, Fab' fragments, $Fab_2$, $F(ab)'_2$ fragments, single chain Fv proteins ("scFv") and disulfide stabilized Fv proteins ("dsFv"), that bind to the target antigen. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. While various antibody fragments are defined in terms of the digestion of an intact antibody, one of skill will appreciate that such fragments may be synthesized de novo either chemically or by utilizing recombinant DNA methodology. Thus, as used herein, the term antibody encompasses e.g., monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, $F(ab')_2$ fragments, antibody fragments that exhibit the desired biological activity, disulfide-linked Fvs (sdFv), intrabodies, and epitope-binding fragments or antigen binding fragments of any of the above.

Papain digestion of antibodies produces two identical antigen-binding fragments, called "Fab" fragments, each with a single antigen-binding site. A "Fab fragment" comprises one light chain and the CH1 and variable regions of one heavy chain. The heavy chain of a Fab molecule cannot form a disulfide bond with another heavy chain molecule. A "Fab' fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an $F(ab')_2$ molecule.

Pepsin treatment of an antibody yields an $F(ab')_2$ fragment that has two antigen-combining sites and is still capable of cross-linking antigen. A "$F(ab')_2$ fragment" contains two light chains and two heavy chains containing a portion of the constant region between the CH1 and CH2 domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649, U.S. Pat. Nos. 4,946,778 and 5,260,203, the disclosures of which are incorporated by reference.

The terms "an antigen-binding fragment" and "antigen-binding protein" as used herein means any protein that binds a specified target antigen. "Antigen-binding fragment" includes but is not limited to antibodies and binding parts thereof, such as immunologically functional fragments. An exemplary antigen-binding fragment of an antibody is the heavy chain and/or light chain CDR(s), or the heavy and/or light chain variable region.

The term "immunologically functional fragment" (or simply "fragment") of an antibody or immunoglobulin chain (heavy or light chain) antigen binding protein, as used herein, is a species of antigen binding protein comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding proteins, including intact antibodies, for binding to a given epitope. In some embodiments, the fragments are neutralizing fragments. In one aspect, such a fragment will retain at least one CDR present in the full-length light or heavy chain, and in some embodiments will comprise a single heavy chain and/or light chain or portion thereof. These biologically active fragments can be produced by recombinant DNA techniques or can be produced by enzymatic or chemical cleavage of antigen binding proteins, including intact antibodies. Immunologically functional immunoglobulin fragments include, but are not limited to, Fab, a diabody, Fab', F(ab')$_2$, Fv, domain antibodies and single-chain antibodies, and can be derived from any mammalian source, including but not limited to human, mouse, rat, camelid or rabbit. It is further contemplated that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

Diabodies are bivalent antibodies comprising two polypeptide chains, wherein each polypeptide chain comprises VH and VL regions joined by a linker that is too short to allow for pairing between two regions on the same chain, thus allowing each region to pair with a complementary region on another polypeptide chain (see, e.g., Holliger et al., Proc. Natl. Acad. Sci. USA, 90:6444-48, 1993; and Poljak et al., Structure, 2:1121-23, 1994). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al., Proc. Natl. Acad. Sci. USA, 78:5807, 1981; by "polydoma" techniques (see, e.g., U.S. Pat. No. 4,474,893); or by recombinant DNA techniques. In various embodiments bispecific antibodies of the present disclosure can have binding specificities for at least two different epitopes at least one of which is a tumor associate antigen. In various embodiments the antibodies and fragments can also be heteroantibodies. Heteroantibodies are two or more antibodies, or antibody binding fragments (e.g., Fab) linked together, each antibody or fragment having a different specificity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method.

The term "chimeric antibody" as used herein refers to an antibody which has framework residues from one species, such as human, and CDRs (which generally confer antigen binding) from another species, such as a murine antibody that specifically binds targeted antigen.

The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "humanized antibody" as used herein refers to an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. In various embodiments, the framework regions are chosen from human germline exon $X_H$, $J_H$, $V_K$ and $J_K$ sequences. For example, acceptor sequences for humanization of FR of a $V_H$ domain can be chosen from genuine $V_H$ exons $V_H$ 1-18 (Matsuda et al., Nature Genetics 3:88-94, 1993) or $V_H$ 1-2 (Shin et al., EMBO J. 10:3641-3645, 1991) and for the hinge region ($J_H$), exon $J_H$-6 (Mattila et al., Eur. J. Immunol. 25:2578-2582, 1995). In other examples, germline $V_K$ exon B3 (Cox et al., Eur. J. Immunol. 24:827-836, 1994) and $J_K$ exon $J_K$-1 (Hieter et al., J. Biol. Chem. 257:1516-1522, 1982) can be chosen as acceptor sequences for $V_L$ domain humanization.

The term "recombinant human antibody", as used herein, is intended to include all human antibodies that are prepared, expressed, created or isolated by recombinant means, such as antibodies expressed using a recombinant expression vector transfected into a host cell; antibodies isolated from a recombinant, combinatorial human antibody library; antibodies isolated from an animal (e.g., a mouse) that is transgenic for human immunoglobulin genes; or antibodies prepared, expressed, created or isolated by any other means that involves splicing of human immunoglobulin gene sequences to other DNA sequences. Such recombinant human antibodies have variable and constant regions derived from human germline immunoglobulin sequences. In various embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. All such recombinant means are well known to those of ordinary skill in the art.

The term "anti-CXCR4 antagonist antibody" (interchangeably termed "anti-CXCR4 antibody") refers to an antibody that is able to bind to CXCR4 and inhibit CXCR4 biological activity and/or downstream pathway(s) mediated by CXCR4 signaling. An anti-CXCR4 antagonist antibody encompasses antibodies that block, antagonize, suppress or reduce (including significantly) CXCR4 biological activity, including downstream pathways mediated by CXCR4 signaling, such as receptor binding and/or elicitation of a cellular response to CXCR4. For purpose of the present invention, it will be explicitly understood that the term "anti-CXCR4 antagonist antibody" encompasses all the previously identified terms, titles, and functional states and characteristics whereby the CXCR4 itself, an CXCR4 biological activity (including but not limited to its ability to mediate any aspect of headache), or the consequences of the biological activity, are substantially nullified, decreased, or neutralized in any meaningful degree. In some embodiment, an anti-CXCR4 antagonist antibody binds CXCR4 and prevents CXCR4 binding to a CXCR4 receptor. In other embodiments, an anti-CXCR4 antibody binds CXCR4 and prevents activation of a CXCR4 receptor. Examples of anti-CXCR4 antagonist antibodies are provided herein.

The term "epitope" as used herein includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. Once a desired epitope on an antigen is determined, it is possible to generate antibodies to that epitope, e.g., using the techniques described in the present disclosure. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen.

An antigen binding protein, including an antibody, "specifically binds" to an antigen if it binds to the antigen with a high binding affinity as determined by a dissociation constant ($K_D$, or corresponding Kb, as defined below) value of at least $1\times10^{-6}$ M, or at least $1\times10^{-7}$ M, or at least $1\times10^{-8}$ M, or at least $1\times10^{-9}$ M, or at least $1\times10^{-10}$ M, or at least $1\times10^{-11}$ M. An antigen binding protein that specifically binds to the human antigen of interest may be able to bind to the same antigen of interest from other species as well, with the same or different affinities. The term "$K_D$" as used herein refers to the equilibrium dissociation constant of a particular antibody-antigen interaction.

The term "surface plasmon resonance" as used herein refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.). For further descriptions, see Jonsson U. et al., Ann. Biol. Clin., 51:19-26, 1993; Jonsson U. et al., Biotechniques, 11:620-627, 1991; Jonsson B. et al., J. Mol. Recognit., 8:125-131, 1995; and Johnsson B. et al., Anal. Biochem, 198:268-277, 1991.

The term "immunogenicity" as used herein refers to the ability of an antibody or antigen binding fragment to elicit an immune response (humoral or cellular) when administered to a recipient and includes, for example, the human anti-mouse antibody (HAMA) response. A HAMA response is initiated when T-cells from a subject make an immune response to the administered antibody. The T-cells then recruit B-cells to generate specific "anti-antibody" antibodies.

The term "immune cell" as used herein means any cell of hematopoietic lineage involved in regulating an immune response against an antigen (e.g., an autoantigen). In various embodiments, an immune cell is, e.g., a T cell, a B cell, a dendritic cell, a monocyte, a natural killer cell, a macrophage, Langerhan's cells, or Kupffer cells.

The terms "polypeptide", "peptide" and "protein" are used interchangeably herein to refer to a polymer of amino acid residues. In various embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

The term "recombinant polypeptide", as used herein, is intended to include all polypeptides, including fusion molecules that are prepared, expressed, created, derived from, or isolated by recombinant means, such as polypeptides expressed using a recombinant expression vector transfected into a host cell.

Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions)

may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

Alanine (A), Serine (S), and Threonine (T)

Aspartic acid (D) and Glutamic acid (E)

Asparagine (N) and Glutamine (Q)

Arginine (R) and Lysine (K)

Isoleucine (I), Leucine (L), Methionine (M), and Valine (V)

Phenylalanine (F), Tyrosine (Y), and Tryptophan (W)

A "non-conservative amino acid substitution" refers to the substitution of a member of one of these classes for a member from another class. In making such changes, according to various embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in various embodiments, the substitution of amino acids whose hydropathic indices are within ±2 is included. In various embodiments, those that are within ±1 are included, and in various embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In various embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in various embodiments, the substitution of amino acids whose hydrophilicity values are within ±2 is included, in various embodiments, those that are within ±1 are included, and in various embodiments, those within ±0.5 are included. Exemplary amino acid substitutions are set forth in Table 1.

TABLE 1

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | |
| Glu | Asp | |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | |
| Trp | Tyr, Phe | Tyr |
| Tyr | Trp, Phe, Thr, Ser | Phe |
| Val | Ile, Met, Leu, Phe, Ala, Norleucine | Leu |

The term "polypeptide fragment" and "truncated polypeptide" as used herein refers to a polypeptide that has an amino-terminal and/or carboxy-terminal deletion as compared to a corresponding full-length protein. In various embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In various embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant" and "polypeptide mutant" as used herein refers to a polypeptide that comprises an amino acid sequence wherein one or more amino acid residues are inserted into, deleted from and/or substituted into the amino acid sequence relative to another polypeptide sequence. In various embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Variants of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm and means that a given sequence is at least 80% identical to another length of another sequence. In various embodiments, the % identity is selected from, e.g., at least 60%, at least 65%, at least 70%, at least 75%, at least 80%, at least 85%, at least 90%, at least 95%, or at least 99% or more sequence identity to a given sequence. In various embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In various embodiments, the % homology is selected from, e.g., at least 60%, at least 65%, at least 70%, at least 75%, at least 80%, at least 85%, at least 90%, at least 95%, or at least 99% or more sequence homology to a given sequence. In various embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., J. Mol. Biol. 215:403-10, 1990 (with special reference to the published default setting, i.e., parameters w=4, t=17) and Altschul et al., Nucleic Acids Res., 25:3389-3402, 1997. Sequence searches are typically carried out using the BLASTP program when evaluating a given amino acid sequence relative to amino acid sequences in the Gen Bank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See Id.

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., less than about 0.1, less than about 0.01, or less than about 0.001.

The terms "substantial similarity" or "substantially similar," in the context of polypeptide sequences, indicate that a polypeptide region has a sequence with at least 70%, typically at least 80%, more typically at least 85%, or at least 90% or at least 95% sequence similarity to a reference sequence. For example, a polypeptide is substantially similar to a second polypeptide, for example, where the two peptides differ by one or more conservative substitution(s).

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA. The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence-dependent and are different under different environmental parameters. An extensive guide to the hybridization of nucleic acids can be found in Tijssen, 1993, Laboratory Techniques in Biochemistry and Molecular Biology—Hybridization with Nucleic Acid Probes, part I, chapter 2, "Overview of principles of hybridization and the strategy of nucleic acid probe assays", Elsevier, N.Y.; Sambrook et al., 2001, Molecular Cloning: A Laboratory Manual, Cold Spring Harbor Laboratory, 3.sup.rd ed., NY; and Ausubel et al., eds., Current Edition, Current Protocols in Molecular Biology, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

A "vector" is a polynucleotide that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06. A nucleotide sequence is "operably linked" to a regulatory sequence if the regulatory sequence affects the expression (e.g., the level, timing, or location of expression) of the nucleotide sequence.

A "host cell" is a cell that can be used to express a polynucleotide of the disclosure. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "isolated molecule" (where the molecule is, for example, a polypeptide or a polynucleotide) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, changes in temperature, pH, salt concentration, etc.

The terms "label" or "labeled" as used herein refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I) fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "immunoconjugate" or "fusion protein" as used herein refers to a molecule comprising an antibody or antigen-binding fragment thereof conjugated (or linked) directly or indirectly to an effector molecule. The effector molecule can be a detectable label, an immunotoxin, cytokine, chemokine, therapeutic agent, or chemotherapeutic agent. The antibody or antigen-binding fragment thereof may be conjugated to an effector molecule via a peptide linker. An immunoconjugate and/or fusion protein retains the immunoreactivity of the antibody or antigen-binding fragment, e.g., the antibody or antigen-binding fragment has approximately the same, or only slightly reduced, ability to bind the antigen after conjugation as before conjugation. As used herein, an immunoconjugate may also be referred to as an antibody drug conjugate (ADC). Because immunoconjugates and/or fusion proteins are originally prepared from two molecules with separate functionalities, such as an antibody and an effector molecule, they are also sometimes referred to as "chimeric molecules."

"Pharmaceutical composition" refers to a composition suitable for pharmaceutical use in an animal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

The terms "treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. As used herein, "treatment" is an approach for obtaining beneficial or desired clinical results. For purposes of this invention, beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delay or slowing of disease progression, amelioration of the disease state, and remission (whether partial or total). Also encompassed by "treatment" is a reduction of pathological consequence of a proliferative disease. The methods of the invention contemplate any one or more of these aspects of treatment.

The term "effective amount" or "therapeutically effective amount" as used herein refers to an amount of a compound or composition sufficient to treat a specified disorder, condition or disease such as ameliorate, palliate, lessen, and/or delay one or more of its symptoms.

It is understood that aspects and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

CXCR4

CXCR4 is an alpha-chemokine receptor specific for stromal-derived-factor-1 (SDF-1 also called CXCL12), a molecule endowed with potent chemotactic activity for lymphocytes. CXCR4 is found in various tissues with predominant expression on lymphocytes (ref). Human genetic studies support the concept that increased CXCR4 activity is associated with compromised immune system and increased risks of cancer and other immunodeficiency diseases. SDF-1 binding to CXCR4 activates a cascade of signaling molecules including suppression of cAMP, activation of phospholipase C and intracellular calcium flux (Mukaida et al., Exp Cell Res., 318(2):95-102, 2012). SDF-1 is expressed on a wide variety of human tissues, including liver, lungs, bone marrow, lymph nodes, stromal and endothelial cells. Similarly, CXCR4 is found in various tissues with predominant expression on lymphocytes (Zhou et al., Curr Med Chem., 26 (17): 3026-3041, 2019). Human genetic studies support the concept that increased CXCR4 activity is associated with compromised immune system and increased risks of cancer and other immunodeficiency diseases.

The term "CXCR4" as used herein includes human CXCR4 (hCXCR4), variants, isoforms, and species homologs of hCXCR4, and analogs having at least one common epitope with hCXCR4. In various embodiments, a hCXCR4 as used herein may comprise the amino acid sequence set forth in SEQ ID NO: 1:

```
                                        (SEQ ID NO: 1)
MEGISSIPLPLLQIYTSDNYTEEMGSGDYDSMKEPCFREENANFNKIFLP

TIYSIIFLTGIVGNGLVILVMGYQKKLRSMTDKYRLHLSVADLLFVITLP

FWAVDAVANWYFGNFLCKAVHVIYTVNLYSSVLILAFISLDRYLAIVHAT

NSQRPRKLLAEKVVYVGVWIPALLLTIPDFIFANVSEADDRYICDRFYPN

DLWVVVFQFQHIMVGLILPGIVILSCYCIIISKLSHSKGHQKRKALKTTV

ILILAFFACWLPYYIGISIDSFILLEIIKQGCEFENTVHKWISITEALAF

FHCCLNPILYAFLGAKFKTSAQHALTSVSRGSSLKILSKGKRGGHSSVST

ESESSSFHSS
```

In various embodiments, a CXCR4 comprises an amino acid sequence that shares an observed homology of, e.g., at least 70%, at least 75%, at least 80%, at least 85%, at least 90%, at least 95%, at least 96%, at least 97%, at least 98%, or at least 99% with the human CXCR4 sequence of SEQ ID NO: 1. In some embodiments, the has at least 70%, at least 75%, at least 80%, at least 85%, at least 90%, at least 95%, at least 96%, at least 97%, at least 98%, at least 99%, at least 1x, at least 1.5x, at least 2x, at least 2.5x, or at least 3x activity of the human CXCR4 of SEQ ID NO: 1. Variants of CXCR4 may be described herein by reference to the addition, deletion, or substitution of amino acid residue present at a given position in the 360 amino acid sequence of SEQ ID NO: 1. Thus, for example, the term "P29W" indicates that the "P" (proline, in standard single letter code) residue at position 29 in SEQ ID NO: 1 has been substituted with a "W" (tryptophan, in standard single letter code).

Antibodies

Methods of generating novel antibodies that bind to human CXCR4 are known to those skilled in the art. For example, a method for generating a monoclonal antibody that binds specifically to an CXCR4 may comprise administering to a mouse an amount of an immunogenic composition comprising the CXCR4 effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the CXCR4. Once obtained, a hybridoma can be propagated in a cell culture, optionally in culture conditions where the hybridoma-derived cells produce the monoclonal antibody that binds specifically to CXCR4. The monoclonal antibody may be purified from the cell culture. A variety of different techniques are then available for testing antibody:antigen interactions to identify particularly desirable antibodies.

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies. See e.g., Jakobovits et al., Proc. Natl. Acad. Sci. USA, 90: 2551-2555, 1993; Jakobovits et al., Nature, 362:255-258, 1993; Lonberg et al., U.S. Pat. No. 5,545,806; Surani et al., U.S. Pat. No. 5,545,807.

Antibodies can be engineered in numerous ways. They can be made as single-chain antibodies (including small modular immunopharmaceuticals or SMIPs™), Fab and $F(ab')_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al., Science, 240:1041-1043, 1988; Liu et al., PNAS USA, 84:3439-3443, 1987; Liu et al., J. Immunol. 139:3521-3526, 1987; Sun et al., PNAS USA, 84:214-218, 1987; Nishimura et al., Canc. Res. 47:999-1005, 1987; Wood et al., Nature 314:446-449, 1985; and Shaw et al., J. Natl Cancer Inst., 80:1553-1559, 1988).

Methods for humanizing antibodies have been described in the art. In practice, humanized antibodies are typically human antibodies in which some hypervariable region residues and possibly some framework region residues are substituted by residues from analogous sites in rodent antibodies. Accordingly, such "humanized" antibodies are chimeric antibodies wherein substantially less than an intact human variable region has been substituted by the corresponding sequence from a nonhuman species. To a degree, this can be accomplished in connection with techniques of humanization and display techniques using appropriate libraries. It will be appreciated that murine antibodies or antibodies from other species can be humanized or primatized using techniques well known in the art (see e.g., Winter et al., Immunol Today, 14:43-46, 1993; and Wright et al., Crit. Reviews in Immunol., 12125-168, 1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777, 085). Also, the use of Ig cDNA for construction of chimeric immunoglobulin genes is known in the art (Liu et al., P.N.A.S. 84:3439, 1987; J. Immunol. 139:3521, 1987). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683, 202). Alternatively, a library is made and screened to isolate the sequence of interest. The DNA sequence encoding the variable region of the antibody is then fused to human constant region sequences. The sequences of human constant regions to genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. In various embodiments, the isotype is selected from the group consisting of IgG1, IgG2, IgG3 and IgG4. Either of the human light chain constant regions, kappa or lambda, may be used. The chimeric, humanized antibody is then expressed by conventional methods.

U.S. Pat. No. 5,693,761 to Queen et al, discloses a refinement on Winter et al. for humanizing antibodies, and is based on the premise that ascribes avidity loss to problems in the structural motifs in the humanized framework which, because of steric or other chemical incompatibility, interfere with the folding of the CDRs into the binding-capable conformation found in the mouse antibody. To address this problem, Queen teaches using human framework sequences closely homologous in linear peptide sequence to framework sequences of the mouse antibody to be humanized. Accordingly, the methods of Queen focus on comparing framework sequences between species. Typically, all available human variable region sequences are compared to a particular mouse sequence and the percentage identity between correspondent framework residues is calculated. The human variable region with the highest percentage is selected to provide the framework sequences for the humanizing project. Queen also teaches that it is important to retain in the humanized framework, certain amino acid residues from the mouse framework critical for supporting the CDRs in a binding-capable conformation. Potential criticality is assessed from molecular models. Candidate residues for retention are typically those adjacent in linear sequence to a CDR or physically within 6 Å of any CDR residue.

In other approaches, the importance of particular framework amino acid residues is determined experimentally once a low-avidity humanized construct is obtained, by reversion of single residues to the mouse sequence and assaying antigen-binding as described by Riechmann et al, 1988. Another example approach for identifying important amino acids in framework sequences is disclosed by U.S. Pat. No. 5,821,337 to Carter et al, and by U.S. Pat. No. 5,859,205 to Adair et al. These references disclose specific Kabat residue positions in the framework, which, in a humanized antibody may require substitution with the correspondent mouse amino acid to preserve avidity.

Another method of humanizing antibodies, referred to as "framework shuffling", relies on generating a combinatorial library with nonhuman CDR variable regions fused in frame into a pool of individual human germline frameworks (Dall'Acqua et al., Methods, 36:43, 2005). The libraries are then screened to identify clones that encode humanized antibodies which retain good binding.

The choice of human variable regions, both light and heavy, to be used in making the desired humanized antibodies is very important to reduce antigenicity. According to the so-called "best-fit" method, the sequence of the variable region of a rodent antibody is screened against the entire library of known human variable-domain sequences. The human sequence that is closest to that of the rodent is then accepted as the human framework region (framework region) for the humanized antibody (Sims et al., J. Immunol., 151:2296, 1993; Chothia et al., J. Mol. Biol., 196:901, 1987). Another method uses a particular framework region derived from the consensus sequence of all human antibodies of a particular subgroup of light or heavy chain variable regions. The same framework may be used for several different humanized antibodies (Carter et al., Proc. Natl. Acad. Sci. USA, 89:4285, 1992; Presta et al., J. Immunol., 151:2623, 1993).

The choice of nonhuman residues to substitute into the human variable region can be influenced by a variety of factors. These factors include, for example, the rarity of the amino acid in a particular position, the probability of interaction with either the CDRs or the antigen, and the probability of participating in the interface between the light and heavy chain variable domain interface. (See, for example, U.S. Pat. Nos. 5,693,761, 6,632,927, and 6,639,055). One method to analyze these factors is through the use of three-dimensional models of the nonhuman and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, nonhuman residues can be selected and substituted for human variable region residues in order to achieve the desired antibody characteristic, such as increased affinity for the target antigen(s).

Methods for making fully human antibodies have been described in the art. By way of example, a method for producing an anti-CXCR4 antibody or antigen-binding fragment thereof comprises the steps of synthesizing a library of human antibodies on phage, screening the library with CXCR4 or an antibody-binding portion thereof, isolating phage that bind CXCR4, and obtaining the antibody from the phage. By way of another example, one method for preparing the library of antibodies for use in phage display techniques comprises the steps of immunizing a non-human animal comprising human immunoglobulin loci with CXCR4 or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant anti-CXCR4 antibodies of the invention may be obtained in this way.

Recombinant human anti-CXCR4 antibodies of the invention can also be isolated by screening a recombinant combinatorial antibody library. Preferably the library is a scFv phage display library, generated using human VL and VH cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology 9:1370-1372 (1991); Hay et al., Hum. Antibod. Hybridomas 3:81-85, 1992; Huse et al., Science 246:1275-1281, 1989; McCafferty et al., Nature 348:552-554, 1990; Griffiths et al., EMBO J. 12:725-734, 1993; Hawkins et al., J. Mol. Biol. 226:889-896, 1992; Clackson et al., Nature 352:624-628, 1991; Gram et al., Proc. Natl. Acad. Sci. USA 89:3576-3580, 1992; Garrad et al., Bio/Technology 9:1373-1377, 1991; Hoogenboom et al., Nuc. Acid Res. 19:4133-4137, 1991; and Barbas et al., Proc. Natl. Acad. Sci. USA 88:7978-7982, 1991, each incorporated herein by reference for purposes of teaching preparation and screening of phase display libraries.

Human antibodies are also produced by immunizing a non-human, transgenic animal comprising within its genome some or all of human immunoglobulin heavy chain and light chain loci with a human IgE antigen, e.g., a XenoMouse™ animal (Abgenix, Inc./Amgen, Inc.—Fremont, Calif.). XenoMouse™ mice are engineered mouse strains that comprise large fragments of human immunoglobulin heavy chain and light chain loci and are deficient in mouse antibody production. See, e.g., Green et al., Nature Genetics 7:13-21, 1994; and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504. XenoMouse™ mice produce an adult-like human repertoire of fully human antibodies and generate antigen-specific human antibodies. In some embodiments, the XenoMouse™ mice contain approximately 80% of the human antibody V gene repertoire through introduction of megabase sized, germline configuration fragments of the human heavy chain loci and kappa light chain loci in yeast artificial chromosome (YAC). In other embodiments, Xeno-Mouse™ mice further contain approximately all of the human lambda light chain locus. See Mendez et al., Nature Genetics 15:146-156, 1997, Green and Jakobovits, J. Exp. Med. 188:483-495 (1998), and WO 98/24893 (each incorporated by reference in its entirety for purposes of teaching the preparation of fully human antibodies). In another aspect, the present invention provides a method for making anti-CXCR4 antibodies from non-human, non-mouse animals by immunizing non-human transgenic animals that comprise human immunoglobulin loci with a CXCR4 antigen. One can produce such animals using the methods described in the above-cited documents.

Characterization of Antibody Binding to Antigen

Antibodies of the present invention can be tested for binding to human CXCR4 by, for example, standard ELISA. As an example, microtiter plates are coated with purified CXCR4 in PBS, and then blocked with 5% bovine serum albumin in PBS. Dilutions of antibody (e.g., dilutions of plasma from CXCR4-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml) and analyzed at OD of 405-650. Preferably, mice which develop the highest titers will be used for fusions. An ELISA assay can also be used to screen for hybridomas that show positive reactivity with CXCR4 immunogen. Hybridomas that bind with high avidity to CXCR4 are subcloned and further characterized. One clone from each hybridoma, which retains the reactivity of the parent cells (by ELISA), can be chosen for making a 5-10 vial cell bank stored at −140° C., and for antibody purification.

To determine if the selected anti-CXCR4 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using CXCR4 coated-ELISA plates as described above. Biotinylated mAb binding can be detected with a strep-avidin-alkaline phosphatase probe. To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-CXCR4 human IgGs can be further tested for reactivity with CXCR4 antigen by Western blotting. Briefly, CXCR4 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Identification of Anti-CXCR4 Antibodies

The present invention provides monoclonal antibodies, and antigen-binding fragments thereof, that specifically bind to CXCR4 antigen.

Further included in the present invention are antibodies that bind to the same epitope as the anti-CXCR4 antibodies of the present invention. To determine if an antibody can compete for binding to the same epitope as the epitope bound by the anti-CXCR4 antibodies of the present invention, a cross-blocking assay, e.g., a competitive ELISA assay, can be performed. In an exemplary competitive ELISA assay, CXCR4 coated on the wells of a microtiter plate is pre-incubated with or without candidate competing antibody and then the biotin labeled anti-CXCR4 antibody of the invention is added. The amount of labeled anti- CXCR4 antibody bound to the CXCR4 antigen in the wells is measured using avidin-peroxidase conjugate and appropriate substrate. The antibody can be labeled with a radioactive or fluorescent label or some other detectable and measurable label. The amount of labeled anti-CXCR4 antibody that bound to the antigen will have an indirect correlation to the ability of the candidate competing antibody (test antibody) to compete for binding to the same epitope, i.e., the greater the affinity of the test antibody for the same epitope, the less labeled antibody will be bound to the antigen-coated wells. A candidate competing antibody is considered an antibody that binds substantially to the same epitope or that competes for binding to the same epitope as an anti-CXCR4 antibody of the invention if the candidate antibody can block binding of the CXCR4 antibody by at least 20%, preferably by at least 20-50%, even more preferably, by at least 50% as compared to the control performed in parallel in the absence of the candidate competing antibody. It will be understood that variations of this assay can be performed to arrive at the same quantitative value.

The amino acid sequences of the heavy chain variable region CDRs and the light chain variable region CDRs of two murine antibodies, 132F3F3H11 (also referred to hereinafter as "A8") and 201D10A1201 (also referred to hereinafter as "A15"), generated as described herein, are shown below in Table 2.

TABLE 2

|  | Heavy Chain CDRs | | |
| --- | --- | --- | --- |
| Ab | HCDR1 | HCDR2 | HCDR3 |
| A8 | SSGMH (SEQ ID NO: 2) | YISSGSSSIYYADTVKG (SEQ ID NO: 4) | PYYYGSIAMDY (SEQ ID NO: 6) |
| A15 | GYAFTDFHLN (SEQ ID NO: 3) | VINPYNGGTNYNQKFKD (SEQ ID NO: 5) | YYASRYGYAMDY (SEQ ID NO: 7) |
|  | Light Chain CDRs | | |
| Ab | LCDR1 | LCDR2 | LCDR3 |
| A8 | KASQDINSYLS (SEQ ID NO: 8) | RANRLVD (SEQ ID NO: 10) | LQYDEFPFT (SEQ ID NO: 12) |
| A15 | RSSKSLLHSNGNTYLY (SEQ ID NO: 9) | RMSNLAS (SEQ ID NO: 11) | MQHVEYPLT (SEQ ID NO: 13) |

In various embodiments of the present invention, the antibody or antigen-binding fragment is a murine antibody, 132F3F3H11 ("A8"), comprising the heavy chain variable region sequence of SEQ ID NO: 14:

(SEQ ID NO: 14)
DVQLVESGGGLVQPGGSRKLSCAASGFTFSSSGMHWVRQAPEKGLEWVAY

ISSGSSSIYYADTVKGRFTISRDNPKNTLFLQMTSLRSEDTAMYYCARPY

YYGSIAMDYWGQGTSVTVSS and the light chain variable region sequence of SEQ ID NO: 18:

(SEQ ID NO: 18)
DIKMTQSPSSMYASLGERVTITCKASQDINSYLSWFQQKPGKSPKTLIYR

ANRLVDGVPSRFSGSGSGQDYSLTISSLEYEDMGIYYCLQYDEFPFTFGS

GTKLEIK

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 14, or its corresponding polynucleotide sequence SEQ ID NO: 15:

(SEQ ID NO: 15)
gatgtgcagctggtggagtctggggggaggcttagtgcagcctggagggtc ccggaaactctcctgtgcagcctctggattcactttcagtagctctggaa tgcactgggttcgtcaggctccagagaagggactggagtgggtcgcatac attagtagtggcagtagttccatctactatgcagacacagtgaagggccg attcaccatctccagagacaatcccaagaacaccctgttcttgcaaatga ccagtctaaggtctgaggacacggccatgtattactgtgcaagaccttat tactacggctccattgctatggactactggggtcaaggaacctcagtcac cgtctcctca and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 18, or its corresponding polynucleotide sequence SEQ ID NO: 19:

(SEQ ID NO: 19)
gacatcaagatgacccagtctccatcttccatgtatgcatctctaggaga gagagtcactatcacttgcaaggcgagtcaggacattaatagctatttaa gctggttccagcagaaaccagggaaatctcctaagaccctgatctatcgt gcaaacagattggtagatggggtcccatcaaggttcagtggcagtggatc tgggcaagattattctctcaccatcagcagcctggagtatgaagatatgg gaatttattattgtctacagtatgatgagtttccattcacgttcggctcg gggacaaagttggaaataaaa

In various embodiments of the present invention, the antibody or antigen-binding fragment is a murine antibody, 201D10A12C1 ("A15"), comprising the heavy chain variable region sequence of SEQ ID NO: 16:

```
                                    (SEQ ID NO: 16)
EVQLQQSGPVLVRPGASVKMSCKASGYAFTDFHLNWVKQSHGKSLEWIGV

INPYNGGTNYNQKFKDKATLTVDKSSSTAYMELNRLTSEDSAVYYCARYY

ASRYGYAMDYWGQGTSVTVSS
``` and the light chain variable region sequence of SEQ ID NO: 20:

```
                                    (SEQ ID NO: 20)
    DIVMTQAAPSVPVTPGESVSISCRSSKSLLHSNGN

TYLYWFLQRPGQSPQLLIYRMSNLASGVPDRFSGS

GSGTAFTLRISRVEAEDVGIYYCMQHVEYPLTFGA

GTKLELK
```

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 16, or its corresponding polynucleotide sequence SEQ ID NO: 17:

```
                                    (SEQ ID NO: 17)
    gaggtccaactgcaacagtctggacctgtgctggt gaggcctgggcttcagtgaagatgtcctgtaagg cttctggatacgcattcactgacttccatttgaac tgggtgaagcagagccatggaaagagccttgagtg gattggagttattaatccttacaacggtggtacta actacaaccagaagttcaaggacaaggccacattg actgttgacaagtcctccagcacagcctacatgga gctcaacagactgacatctgaggactctgcagtct attactgtgcaagatactacgctagtaggtacggc tatgctatggactactggggtcaaggaacctcagt caccgtctcctca
``` and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 20, or its corresponding polynucleotide sequence SEQ ID NO: 21:

```
                                    (SEQ ID NO: 21)
    gatattgtgatgactcaggctgcaccctctgtacc tgtcactcctggagagtcagtatccatctcctgca
```

32

```
                            -continued
    ggtctagtaagagtctcctgcatagtaatggcaac acttacttgtattggttcctgcagaggccaggcca gtctcctcagctcctgatatatcggatgtccaacc ttgcctcaggagtcccagacaggttcagtggcagt gggtcaggaactgctttcacactgagaatcagtag agtggaggctgaggatgtgggtatttattattgta tgcaacatgtagaatatcctctcacgttcggtgct gggaccaagctggagctgaaa
```

In various embodiments, the heavy chain variable domain comprises a sequence of amino acids that is encoded by a polynucleotide that hybridizes under moderately stringent conditions to the complement of a polynucleotide that encodes a heavy chain variable domain having the sequence of SEQ ID NOs: 14 and 16. In another embodiment, the heavy chain variable domain comprises a sequence of amino acids that is encoded by a polynucleotide that hybridizes under stringent conditions to the complement of a polynucleotide that encodes a heavy chain variable domain having the sequence of SEQ ID NOs: 15 and 17. In another embodiment, the light chain variable domain comprises a sequence of amino acids that is encoded by a polynucleotide that hybridizes under moderately stringent conditions to the complement of a polynucleotide that encodes a light chain variable domain having the sequence of SEQ ID NOs: 18 and 20. In another embodiment, the light chain variable domain comprises a sequence of amino acids that is encoded by a polynucleotide that hybridizes under stringent conditions to the complement of a polynucleotide that encodes a light chain variable domain having the sequence of SEQ ID NOs: 19 and 21.

In various embodiments, antibodies of the present invention include antibodies that bind to the same epitope as murine antibody A8. In various embodiments, antibodies of the present invention include antibodies that bind to the same epitope as murine antibody A15.

In various embodiments of the present invention, the antibody or antigen-binding fragment is a murine-human chimeric antibody (derived from murine antibody A15 and human IgG1) comprising the heavy chain sequence of SEQ ID NO: 22 and wherein amino acids 1-19 are a leader sequence:

```
                                    (SEQ ID NO: 22)
    MGWSCIILFLVATATGVHSEVQLQQSGPVLVRPGA

SVKMSCKASGYAFTDFHLNWVKQSHGKSLEWIGVI

NPYNGGTNYNQKFKDKATLTVDKSSSTAYMELNRL

TSEDSAVYYCARYYASRYGYAMDYWGQGTSVTVSS

ASTKGPSVFPLAPSSKSTSGGTAALGCLVKDYFPE

PVTVSWNSGALTSGVHTFPAVLQSSGLYSLSSVVT

VPSSSLGTQTYICNVNHKPSNTKVDKKVEPKSCDK

THTCPPCPAPELLGGPSVFLFPPKPKDTLMISRTP

EVTCVVVDVSHEDPEVKFNWYVDGVEVHNAKTKPR

EEQYNSTYRVVSVLTVLHQDWLNGKEYKCKVSNKA
```

-continued

```
LPAPIEKTISKAKGQPREPQVYTLPPSRDELTKNQ

VSLTCLVKGFYPSDIAVEWESNGQPENNYKTTPPV

LDSDGSFFLYSKLTVDKSRWQQGNVFSCSVMHEAL

HNHYTQKSLSLSPGK
``` and the light chain sequence of SEQ ID NO: 23 and wherein
amino acids 1-19 are a leader sequence:

```
                                  (SEQ ID NO: 23)
MGWSCIILFLVATATGVHSDIVMTQAAPSVPVTPG

ESVSISCRSSKSLLHSNGNTYLYWFLQRPGQSPQL

LIYRMSNLASGVPDRFSGSGSGTAFTLRISRVEAE

DVGIYYCMQHVEYPLTFGAGTKLELKRTVAAPSVF

IFPPSDEQLKSGTASVVCLLNNFYPREAKVQWKVD

NALQSGNSQESVTEQDSKDSTYSLSSTLTLSKADY

EKHKVYACEVTHQGLSSPVTKSFNRGEC
```

In various embodiments of the present invention, the
antibody or antigen-binding fragment is an isolated human-
ized antibody or antigen-binding fragment comprising a
heavy chain variable region having a sequence identical,
substantially identical or substantially similar to SEQ ID
NOs: 24-29, and a light chain variable region having the
sequence identical, substantially identical or substantially
similar to SEQ ID NOs: 30-32. In various embodiments the
antibody is a humanized antibody or antigen-binding frag-
ment thereof which comprises the heavy chain variable
region having the amino acid sequence set forth in SEQ ID
NO: 24 and the light chain variable region having the amino
acid sequence set forth in SEQ ID NO: 30. In various
embodiments the antibody is a humanized antibody or
antigen-binding fragment thereof which comprises the
heavy chain variable region having the amino acid sequence
set forth in SEQ ID NO: 24 and the light chain variable
region having the amino acid sequence set forth in SEQ ID
NO: 31. In various embodiments the antibody is a human-
ized antibody or antigen-binding fragment thereof which
comprises the heavy chain variable region having the amino
acid sequence set forth in SEQ ID NO: 24 and the light chain
variable region having the amino acid sequence set forth in
SEQ ID NO: 32.

In various embodiments, the antibodies or antigen-bind-
ing fragments thereof comprise a heavy chain variable
domain comprising a sequence of amino acids that differs
from the sequence of a heavy chain variable domain having
the amino acid sequence set forth in SEQ ID NOs: 24-29
only at 15, 14, 13, 12, 11, 10, 9, 8, 7, 6, 5, 4, 3, 2, 1 or 0
residues, wherein each such sequence difference is indepen-
dently either a deletion, insertion, or substitution of one
amino acid residue. In various embodiments, the antibodies
or antigen-binding fragments thereof comprise a heavy
chain variable domain comprising a sequence that has at
least about 80%, at least about 85%, at least about 90%,
91%, 92%, 93%, 94%, 95%, 96%, 97%, 98%, or at least
about 99% identity to the amino acid sequence as set forth
in SEQ ID NOs: 24-29.

In various embodiments, an isolated humanized antibody
or antigen-binding fragment thereof of the present invention
binds to human CXCR4 and comprises sequence of amino
acids that differs from the sequence of a light chain variable domain having the amino acid sequence set forth in SEQ ID
NOs: 30-32 only at 15, 14, 13, 12, 11, 10, 9, 8, 7, 6, 5, 4, 3,
2, 1 or 0 residues, wherein each such sequence difference is
independently either a deletion, insertion, or substitution of
one amino acid residue. In various embodiments, the anti-
bodies or antigen-binding fragments thereof comprise a light
chain variable domain comprising a sequence that has at
least about 80%, at least about 85%, at least about 90%,
91%, 92%, 93%, 94%, 95%, 96%, 97%, 98%, or at least
about 99% identity to the amino acid sequence as set forth
in SEQ ID NOs: 30-32.

In various embodiments of the present invention, the
antibody is a humanized IgG comprising the heavy chain
sequence ("H1") of SEQ ID NO: 33:

```
                                  (SEQ ID NO: 33)
QVQLVQSGAEVKKPGASVKVSCKASGYAFTDFHLN

WVRQAPGQGLEWMGVINPYNGGTNYNQKFKDRVTM

TRDTSISTAYMELSRLRSDDTAVYYCARYYASRYG

YAMDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKKVEPKSCDKTHTCPPCPAPELLGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK
``` and the light chain sequence ("L1") of SEQ ID NO: 35:

```
                                  (SEQ ID NO: 35)
DIVMTQSPLSLPVTPGEPASISCRSSKSLLHSNGN

TYLYWYLQKPGQSPQLLIYRMSNLASGVPDRFSGS

GSGTDFTLKISRVEAEDVGVYYCMQHVEYPLTFGG

GTKLEIKRTVAAPSVFIFPPSDEQLKSGTASVVCL

LNNFYPREAKVQWKVDNALQSGNSQESVTEQDSKD

STYSLSSTLTLSKADYEKHKVYACEVTHQGLSSPV

TKSFNRGEC
```

In certain alternative embodiments, the antibody is an
antibody comprising a heavy chain and a light chain,
wherein the heavy chain comprises a sequence that has at
least about 80%, at least about 85%, at least about 90%,
91%, 92%, 93%, 94%, 95%, 96%, 97%, 98%, or at least
about 99% identity to the amino acid sequence as set forth
in SEQ ID NO: 33, or its corresponding polynucleotide
sequence SEQ ID NO: 34:

```
                                  (SEQ ID NO: 34)
caggtgcagctggtgcagagcggagcagaggtgaa gaagccaggagcctccgtgaaggtgtcttgcaagg
```

-continued

```
ccagcggctacgccttcaccgactttcacctgaac tgggtgcggcaggcaccaggacagggactggagtg gatgggcgtgatcaacccttacaatggcggcacaa actataatcagaagttcaaggacagggtgaccatg acacgcgatacctctatcagcacagcctacatgga gctgtcccggctgagatctgacgataccgccgtgt actattgtgcccggtactatgcctccagatacggc tatgccatggattattggggccagggcaccctggt gacagtgagctccgccagcaccaagggcccttccg tgtttccactggccccctcctctaaatccacatct ggcggcaccgccgccctgggctgtctggtgaagga ctacttcccagagcctgtgacagtgtcctggaact ctggcgccctgacatccggcgtgcacacatttcca gccgtgctgcagagctccggcctgtacagcctgtc tagcgtggtgacagtgccctcctctagcctgggca cacagacctatatctgcaacgtgaatcacaagcca agcaataccaaggtggacaagaaggtggagcccaa gtcctgtgataagacacacacctgccccccttgtc ctgctcccgagctgctgggcggccctagcgtgttc ctgtttccacccaagcctaaggacaccctgatgat ctcccggacacccgaggtgacctgcgtggtggtgg acgtgtctcacgaggatcctgaggtgaagttcaac tggtatgtggatggcgtggaggtgcacaatgccaa gaccaagcccagagaggagcagtacaactctacat ataggtggtgagcgtgctgaccgtgctgcaccag gactggctgaacggcaaggagtataagtgcaaggt gtccaataaggccctgcccgcccccatcgagaaga caatcagcaaggccaagggccagcctcgggagcca caggtgtacaccctgcctccatccagagacgagct gacaaagaaccaggtgtctctgacatgtctggtga agggcttctatcctagcgatatcgccgtggagtgg gagtccaatggccagccagagaacaattacaagac cacacccctgtgctggactccgatggctccttct ttctgtattccaagctgaccgtggataagtctcgg tggcagcagggcaacgtgttcagctgttccgtgat gcacgaagccctgcataatcactatactcagaaat ccctgtccctgtcacctggaaagtga
``` and wherein the light chain comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 35, or its corresponding polynucleotide sequence SEQ ID NO: 36:

```
                                  (SEQ ID NO: 36)
gacatcgtgatgacccagtcccctctgtctctgcc cgtgacacctggcgagccagcctctatcagctgca ggagctccaagagcctgctgcactccaacggcaat acctacctgtattggtacctgcagaagcccggcca gtcccctcagctgctgatctatcggatgtctaacc tggccagcggcgtgccagacagattctccggatct ggaagcggaaccgacttcaccctgaagatctctcg ggtggaggccgaggatgtgggcgtgtactattgta tgcagcacgtggagtacccactgaccttcggcgga ggaacaaagctggagatcaagaggacagtggccgc cccaagcgtgttcatctttcccccttccgacgagc agctgaagtctggcaccgccagcgtggtgtgcctg ctgaacaacttctaccctcgggaggccaaggtcca gtggaaggtggataacgccctgcagtctggcaata gccaggagtccgtgaccgagcaggactctaaggat agcacatattccctgtctagcaccctgacactgag caaggccgattacgagaagcacaaggtgtatgcct gtgaagtcacccatcaggggctgtcatcacccgtc actaagtcattcaatcgcggagaatgctag
```

In various embodiments of the present invention, the antibody is a humanized IgG comprising the heavy chain sequence ("H1") of SEQ ID NO: 33 and the light chain sequence ("L2") of SEQ ID NO: 37:

```
                                  (SEQ ID NO: 37)
DIVMTQSPLSLPVTPGEPVSISCRSSKSLLHSNGN

TYLYWFLQKPGQSPQLLIYRMSNLASGVPDRFSGS

GSGTDFTLKISRVEAEDVGVYYCMQHVEYPLTFGG

GTKLEIKRTVAAPSVFIFPPSDEQLKSGTASVVCL

LNNFYPREAKVQWKVDNALQSGNSQESVTEQDSKD

STYSLSSTLTLSKADYEKHKVYACEVTHQGLSSPV

TKSFNRGEC
```

In certain alternative embodiments, the antibody is an antibody comprising a heavy chain and a light chain, wherein the heavy chain comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 33, or its corresponding polynucleotide sequence SEQ ID NO: 38, wherein the light chain comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 37, or its corresponding polynucleotide sequence SEQ ID NO: 38:

(SEQ ID NO: 38)

```
gacatcgtgatgacccagtccctctgtctctgcc cgtgacacctggcgagccagtgtctatcagctgca ggagctccaagagcctgctgcactccaacggcaat acctacctgtattggttcctgcagaagcccggcca gtcccctcagctgctgatctaccggatgtctaacc tggccagcggcgtgccagacagattctccggatct ggaagcggaaccgacttcaccctgaagatctctcg ggtggaggccgaggatgtgggcgtgtactattgta tgcagcacgtggagtatcccctgacctttggcggc ggcacaaagctggagatcaagaggacagtggccgc cccaagcgtgttcatctttcccccttccgacgagc agctgaagtctggcaccgccagcgtggtgtgcctg ctgaacaacttctaccctcgggaggccaaggtcca gtggaaggtggataacgccctgcagtctggcaata gccaggagtccgtgaccgagcaggactctaaggat agcacatattccctgtctagcaccctgacactgag caaggccgattacgagaagcacaaggtgtatgcct gtgaagtcacccatcaggggctgtcatcacccgtc actaagtcattcaatcgcggagaatgctag
```

In various embodiments of the present invention, the antibody is a humanized IgG comprising the heavy chain sequence ("H1") of SEQ ID NO: 33 and the light chain sequence ("L3") of SEQ ID NO: 39:

(SEQ ID NO: 39)

```
DIVMTQSALSLPVTPGEPVSISCRSSKSLLHSNGN

TYLYWFLQKPGQSPQLLIYRMSNLASGVPDRFSGS

GSGTDFTLKISRVEAEDVGVYYCMQHVEYPLTFGG

GTKLEIKRTVAAPSVFIFPPSDEQLKSGTASVVCL

LNNFYPREAKVQWKVDNALQSGNSQESVTEQDSKD

STYSLSSTLTLSKADYEKHKVYACEVTHQGLSSPV

TKSFNRGEC
```

In certain alternative embodiments, the antibody is an antibody comprising a heavy chain and a light chain, wherein the heavy chain comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 33, wherein the light chain comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 39, or its corresponding polynucleotide sequence SEQ ID NO: 40:

(SEQ ID NO: 40)

```
gacatcgtgatgacccagtccgccctgtctctgcc agtgacacctggagagccagtgtctatcagctgca ggagctccaagagcctgctgcactccaacggcaat acctacctgtattggttcctgcagaagcccggcca gtcccctcagctgctgatctaccggatgtctaacc tggccagcggcgtgccagacagattctccggatct ggaagcggaaccgacttcaccctgaagatctctcg ggtggaggccgaggatgtgggcgtgtactattgta tgcagcacgtggagtatcccctgacctttggcggc ggcacaaagctggagatcaagaggacagtggccgc cccaagcgtgttcatctttcccccttccgacgagc agctgaagtctggcaccgccagcgtggtgtgcctg ctgaacaacttctaccctcgggaggccaaggtcca gtggaaggtggataacgccctgcagtctggcaata gccaggagtccgtgaccgagcaggactctaaggat agcacatattccctgtctagcaccctgacactgag caaggccgattacgagaagcacaaggtgtatgcct gtgaagtcacccatcaggggctgtcatcacccgtc actaagtcattcaatcgcggagaatgctag
```

In various embodiments of the present disclosure, the antibody may be an anti-CXCR4 antibody that has the same or higher antigen-binding affinity as that of the antibody comprising the heavy chain sequence as set forth in any of SEQ ID NO: 33. In various embodiments, the antibody may be an anti-CXCR4 antibody which binds to the same epitope as the antibody comprising the heavy chain sequence as set forth in any of SEQ ID NO: 33. In various embodiments, the antibody is an anti-CXCR4 antibody which competes with the antibody comprising the heavy chain sequence as set forth in any of SEQ ID NO: 33. In various embodiments, the antibody may be an anti-CXCR4 antibody which comprises at least one (such as two or three) CDRs of the heavy chain sequence as set forth in any of SEQ ID NO: 33.

In various embodiments, the antibody contains an heavy chain amino acid sequence that shares an observed homology of, e.g., at least 70%, at least 75%, at least 80%, at least 85%, at least 90%, at least 95%, at least 96%, at least 97%, at least 98%, or at least 99% with any of SEQ ID NO: 33.

In various embodiments of the present disclosure the antibody may be an anti-CXCR4 antibody that has the same or higher antigen-binding affinity as that of the antibody comprising the light chain sequence as set forth in any of SEQ ID NOs: 35, 37 and 39. In various embodiments, the antibody may be an anti-CXCR4 antibody which binds to the same epitope as the antibody comprising the light chain sequence as set forth in any of SEQ ID NOs: 35, 37 and 39. In various embodiments, the antibody is an anti-CXCR4 antibody which competes with the antibody comprising the light chain sequence as set forth in any of SEQ ID NOs: 35, 37 and 39. In various embodiments, the antibody may be an anti-CXCR4 antibody which comprises at least one (such as two or three) CDRs of the light chain sequence as set forth in any of SEQ ID NOs: 35, 37 and 39.

In various embodiments, the antibody contains an light chain amino acid sequence that shares an observed homology of, e.g., at least 70%, at least 75%, at least 80%, at least 85%, at least 90%, at least 95%, at least 96%, at least 97%, at least 98%, or at least 99% with any of SEQ ID NOs: 35, 37 and 39. In various embodiments, the antibody contains a nucleic acid sequence that shares an observed homology of, e.g., at least 70%, at least 75%, at least 80%, at least 85%, at least 90%, at least 95%, at least 96%, at least 97%, at least 98%, or at least 99% with any of SEQ ID NOs: 35, 37 and 39.

In various embodiments, an isolated humanized antibody or antigen-binding fragment thereof of the present invention binds to human CXCR4 and comprises a heavy chain variable region having a sequence identical, substantially identical or substantially similar to SEQ ID NO; 33, and a light chain variable region having the sequence identical, substantially identical or substantially similar to SEQ ID NOs: 35, 37 and 39. In various embodiments, an isolated humanized antibody or antigen-binding fragment thereof of the present invention binds to human CXCR4 and comprises the heavy chain sequence set forth in SEQ ID NO: 33, and the light chain sequence set forth in SEQ ID NO: 35. In various embodiments, an isolated humanized antibody or antigen-binding fragment thereof of the present invention binds to human CXCR4 and comprises the heavy chain sequence set forth in SEQ ID NO: 33, and the light chain sequence set forth in SEQ ID NO: 37. In various embodiments, an isolated humanized antibody or antigen-binding fragment thereof of the present invention binds to human CXCR4 and comprises the heavy chain sequence set forth in SEQ ID NO: 33, and the light chain sequence set forth in SEQ ID NO: 39.

Antibodies or antigen-binding fragments thereof of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a IgA-, IgD-, IgE-, IgG- and IgM-type heavy chain constant region. In various embodiments, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lanitto et al., Methods Mol. Biol. 178:303-16, 2002.

In various embodiments, an antibody of the invention further comprises a light chain kappa or lambda constant domain, or a fragment thereof, and further comprises a heavy chain constant domain, or a fragment thereof. Sequences of the light chain constant region and heavy chain constant region used in the exemplified antibodies, and polynucleotides encoding them, are provided below.

```
Light Chain (Kappa) Constant Region
                              (SEQ ID NO: 41)
RTVAAPSVFIFPPSDEQLKSGTASVVCLLNNFYPR

EAKVQWKVDNALQSGNSQESVTEQDSKDSTYSLSS

TLTLSKADYEKHKVYACEVTHQGLSSPVTKSFNRG

EC

Light Chain (Lambda) Constant Region
                              (SEQ ID NO: 42)
GQPKAAPSVTLFPPSSEELQANKATLVCLISDFYP

GAVTVAWKADSSPVKAGVETTTPSKQSNNKYAASS

YLSLTPEQWKSHRSYSCQVTHEGSTVEKTVAPTEC

S

Heavy Chain Constant Region
                              (SEQ ID NO: 43)
ASTKGPSVFPLAPSSKSTSGGTAALGCLVKDYFPE

PVTVSWNSGALTSGVHTFPAVLQSSGLYSLSSVVT

VPSSSLGTQTYICNVNHKPSNTKVDKKVEPKSCDK

THTCPPCPAPELLGGPSVFLFPPKPKDTLMISRTP

EVTCVVVDVSHEDPEVKFNWYVDGVEVHNAKTKPR

EEQYNSTYRVVSVLTVLHQDWLNGKEYKCKVSNKA

LPAPIEKTISKAKGQPREPQVYTLPPSRDELTKNQ

VSLTCLVKGFYPSDIAVEWESNGQPENNYKTTPPV

LDSDGSFFLYSKLTVDKSRWQQGNVFSCSVMHEAL

HNHYTQKSLSLSPGK
```

Antibodies of the present invention may also be described or specified in terms of their cross-reactivity. Antibodies that bind CXCR4s, which have at least 95%, at least 90%, at least 85%, at least 80%, at least 75%, at least 70%, at least 65%, at least 60%, at least 55%, and at least 50% identity (as calculated using methods known in the art and described herein) to human CXCR4 are also included in the present invention.

Further included in the present invention are antibodies that bind to the same epitope as the anti-CXCR4 antibodies of the present invention. To determine if an antibody can compete for binding to the same epitope as the epitope bound by the anti-CXCR4 antibodies of the present invention, a cross-blocking assay, e.g., a competitive ELISA assay, can be performed. In an exemplary competitive ELISA assay, CXCR4 coated on the wells of a microtiter plate is pre-incubated with or without candidate competing antibody and then the biotin labeled anti-CXCR4 antibody of the invention is added. The amount of labeled anti-CXCR4 antibody bound to the CXCR4 antigen in the wells is measured using avidin-peroxidase conjugate and appropriate substrate. The antibody can be labeled with a radioactive or fluorescent label or some other detectable and measurable label. The amount of labeled anti-CXCR4 antibody that bound to the antigen will have an indirect correlation to the ability of the candidate competing antibody (test antibody) to compete for binding to the same epitope, i.e., the greater the affinity of the test antibody for the same epitope, the less labeled antibody will be bound to the antigen-coated wells. A candidate competing antibody is considered an antibody that binds substantially to the same epitope or that competes for binding to the same epitope as an anti-CXCR4 antibody of the invention if the candidate antibody can block binding of the CXCR4 antibody by at least 20%, by at least 30%, by at least 40%, or by at least 50% as compared to the control performed in parallel in the absence of the candidate competing antibody. It will be understood that variations of this assay can be performed to arrive at the same quantitative value.

In certain alternative embodiments, the antibodies of the present invention can be engineered by modifying one or more residues within one or both variable regions (i.e., $V_H$ and/or $V_L$), or by modifying residues within the constant region(s), e.g., to alter the effector function(s) of the antibody. In various embodiments, the variable region of the antibody will by modified by performing CDR grafting using framework sequences can be obtained from public DNA databases or published references that include germline antibody gene sequences (e.g., Tomlinson, I. M., et al., J. Mol. Biol. 227:776-798, 1992; and Cox, J. P. L. et al., Eur. J. Immunol. 24:827-836, 1994; the contents of each of which are expressly incorporated herein by reference). In various embodiments, the antibodies may be modified using site-directed mutagenesis or PCR-mediated mutagenesis to introduce a mutation(s) in the VH and/or VL which improves binding affinity and/or decreases immunogenicity. In various embodiments, the antibodies may be modified in the Fc region for purposes of altering the serum half-life, complement fixation, Fc receptor binding, and/or antigen-dependent cellular cytotoxicity of the antibody. In various embodiments, the antibodies may be modified for purposes of modifying the glycosylation of the antibody. Methods for performing each of the modifications described herein, and others, are well known to the skilled artisan.

Pharmaceutical Compositions

In another aspect, the present invention provides a pharmaceutical composition comprising an antibody or antigen-binding fragment thereof as described above. The pharmaceutical compositions, methods and uses of the invention thus also encompass embodiments of combinations (co-administration) with other active agents, as detailed below.

Generally, the antibodies, or antigen-binding fragments thereof antibodies of the present invention are suitable to be administered as a formulation in association with one or more pharmaceutically acceptable excipient(s). The term 'excipient' is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the antibodies and portions of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Various embodiments include the intravenous and the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-CXCR4 antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurized container, pump, spray, atomizer (preferably an atomizer using electrohydrodynamics to produce a fine mist), or nebulizer, with or without the use of a suitable propellant, or as nasal drops.

The pressurized container, pump, spray, atomizer, or nebulizer generally contains a solution or suspension of an antibody of the invention comprising, for example, a suitable agent for dispersing, solubilizing, or extending release of the active, a propellant(s) as solvent.

Prior to use in a dry powder or suspension formulation, the drug product is generally micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the compound of the invention, a suitable powder base and a performance modifier.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate- and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

The antibodies and antibody portions of the invention may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Pharmaceutical compositions intended for oral use may be prepared according to any method known to the art for the manufacture of pharmaceutical compositions and such compositions may contain one or more agents selected from the group consisting of sweetening agents in order to provide a pharmaceutically elegant and palatable preparation. For example, to prepare orally deliverable tablets, the antibody or antigen-binding fragment thereof is mixed with at least one pharmaceutical excipient, and the solid formulation is compressed to form a tablet according to known methods, for delivery to the gastrointestinal tract. The tablet composition is typically formulated with additives, e.g. a saccharide or cellulose carrier, a binder such as starch paste or methyl cellulose, a filler, a disintegrator, or other additives typically usually used in the manufacture of medical preparations. To prepare orally deliverable capsules, DHEA is mixed with at least one pharmaceutical excipient, and the solid formulation is placed in a capsular container suitable for delivery to the gastrointestinal tract. Compositions comprising antibodies or antigen-binding fragments thereof may be prepared as described generally in Remington's Pharmaceutical Sciences, 18th Ed. 1990 (Mack Publishing Co. Easton Pa. 18042) at Chapter 89, which is herein incorporated by reference.

In various embodiments, the pharmaceutical compositions are formulated as orally deliverable tablets containing antibodies or antigen-binding fragments thereof in admixture with non-toxic pharmaceutically acceptable excipients which are suitable for manufacture of tablets. These excipients may be inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid, or talc. The tablets may be uncoated or they may be coated with known techniques to delay disintegration and absorption in the gastrointestinal track and thereby provide a sustained action over a longer period of time. For example, a time delay material such as glyceryl monostearate or glyceryl distearate alone or with a wax may be employed.

In various embodiments, the pharmaceutical compositions are formulated as hard gelatin capsules wherein the antibody or antigen-binding fragment thereof is mixed with an inert solid diluent, for example, calcium carbonate, calcium phosphate, or kaolin or as soft gelatin capsules wherein the antibody or antigen-binding fragment thereof is mixed with an aqueous or an oil medium, for example, arachis oil, peanut oil, liquid paraffin or olive oil.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Therapeutic Uses

In another aspect, the present invention relates to methods of treating a subject suffering from a CXCR4-associated disorder, comprising administering to said subject a therapeutically effective amount of an antibody or antigen-binding fragment thereof of the present invention. In various embodiments, the subject is a human subject.

In various embodiments, the present invention provides methods for treating cancer in a subject, comprising administering to said subject a therapeutically effective amount (either as monotherapy or in a combination therapy regimen) of an antibody or antigen-binding fragment thereof of the present invention. Such disorders include, but are not limited to solid tumors, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, and combinations of said cancers. In various embodiments, the subject previously responded to treatment with an anti-cancer therapy, but, upon cessation of therapy, suffered relapse (hereinafter "a recurrent cancer"). In various embodiments, the subject has resistant or refractory cancer. In various embodiments, the cancerous cells are immunogenic tumors (e.g., those tumors for which vaccination using the tumor itself can lead to immunity to tumor challenge). In various embodiments, the cancer is selected from the group consisting of melanoma (e.g., metastatic malignant melanoma), colorectal cancer (CRC), renal cancer, bladder cancer, non-small-cell lung cancer (NSCLC), prostate cancer, breast cancer, colon cancer, ovarian cancer and lung cancer.

In various embodiments, the subject previously responded to treatment with an anti-cancer therapy, but, upon cessation of therapy, suffered relapse (hereinafter "a recurrent cancer"). In various embodiments, the subject has resistant or refractory cancer. In various embodiments, the cancerous cells are immunogenic tumors (e.g., those tumors for which vaccination using the tumor itself can lead to immunity to tumor challenge).

In various embodiments, the present antibodies and antigen-binding fragments thereof can be utilized to directly kill or ablate cancerous cells in vivo. Direct killing involves administering the antibodies (which are optionally fused to a cytotoxic drug) to a subject requiring such treatment. In various embodiments, the cancer comprises cancer cells expressing CXCR4 at a higher level than noncancerous cells of a comparable tissue. Since the antibodies recognize CXCR4 on cancer cells, any such cells to which the antibodies bind are destroyed. Where the antibodies are used alone to kill or ablate cancer cells, such killing or ablation can be affected by initiating endogenous host immune functions, such as CDC and/or ADCC. Assays for determining whether an antibody kills cells in this manner are within the purview of those skilled in the art.

In various embodiments, the present antibodies and antigen-binding fragments thereof can be utilized to promote growth inhibition and/or proliferation of a cancerous tumor cell. These methods may inhibit or prevent the growth of the cancer cells of said subject, such as for example, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. As a result, where the cancer is a solid tumor, the modulation may reduce the size of the solid tumor by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

The inhibition of the cancer cell proliferation can be measured by cell-based assays, such as bromodeoxyuridine (BRDU) incorporation (Hoshino et al., Int. J. Cancer 38, 369, 1986; Campana et al., J. Immunol. Meth. 107:79, 1988; [³H]-thymidine incorporation (Chen, J., Oncogene 13:1395-403, 1996; Jeoung, J., J. Biol. Chem. 270:18367-73, 1995; the dye Alamar Blue (available from Biosource International) (Voytik-Harbin et al., In Vitro Cell Dev Biol Anim 34:239-46, 1998). The anchorage independent growth of cancer cells is assessed by colony formation assay in soft agar, such as by counting the number of cancer cell colonies formed on top of the soft agar (see Examples and Sambrook et al., Molecular Cloning, Cold Spring Harbor, 1989).

The inhibition of cancer cell growth in a subject may be assessed by monitoring the cancer growth in a subject, for example in an animal model or in human subjects. One exemplary monitoring method is tumorigenicity assays. In one example, a xenograft comprises human cells from a pre-existing tumor or from a tumor cell line. Tumor xenograft assays are known in the art and described herein (see, e.g., Ogawa et al., Oncogene 19:6043-6052, 2000). In another embodiment, tumorigenicity is monitored using the hollow fiber assay, which is described in U.S. Pat. No. 5,698,413, which is incorporated herein by reference in its entirety.

The percentage of the inhibition is calculated by comparing the cancer cell proliferation, anchorage independent growth, or cancer cell growth under modulator treatment with that under negative control condition (typically without modulator treatment). For example, where the number of cancer cells or cancer cell colonies (colony formation assay), or PRDU or [³H]-thymidine incorporation is A (under the treatment of modulators) and C (under negative control condition), the percentage of inhibition would be $(C-A)/C \times 100\%$.

Examples of tumor cell lines derived from human tumors and available for use in the in vitro and in vivo studies include, but are not limited to, leukemia cell lines (e.g., CCRF-CEM, HL-60(TB), K-562, MOLT-4, RPM1-8226, SR, P388 and P388/ADR); non-small cell lung cancer cell lines (e.g., A549/ATCC, EKVX, HOP-62, HOP-92, NCI-H226, NCI-H23, NCI-H322M, NCI-H460, NCI-H522 and LXFL 529); small cell lung cancer cell lines (e.g., DMS 114 and SHP-77); colon cancer cell lines (e.g., COLO 205, HCC-2998, HCT-116, HCT-15, HT29, KM12, SW-620, DLD-1 and KM20L2); central nervous system (CNS) cancer cell lines (e.g., SF-268, SF-295, SF-539, SNB-19, SNB-75, U251, SNB-78 and XF 498); melanoma cell lines (e.g., LOX I MVI, MALME-3M, M14, SK-MEL-2, SK-MEL-28, SK- MEL-5, UACC-257, UACC-62, RPMI-7951 and M19-MEL); ovarian cancer cell lines (e.g., IGROV1, OVCAR-3, OVCAR-4, OVCAR-5, OVCAR-8 and SK-OV-3); renal cancer cell lines (e.g., 786-0, A498, ACHN, CAKI-1, RXF 393, SN12C, TK-10, UO-31, RXF-631 and SN12K1); prostate cancer cell lines (e.g., PC-3 and DU-145); breast cancer cell lines (e.g., MCF7, NCI/ADR-RES, MDA-MB-231/ATCC, HS 578T, MDA-MB-435, BT-549, T-47D and MDA-MB-468); and thyroid cancer cell lines (e.g., SK-N-SH).

In another aspect, the present invention provides methods for treating a rare disorder in a subject, comprising administering to the subject a therapeutically effective amount (either as monotherapy or in a combination therapy regimen) of an isolated antibody or antigen-binding fragment of the present invention. In various embodiments, the rare disorder is selected from Waldenstrom Macroglobulinemia (WM) and WHIM syndrome. Waldenstrom Macroglobulinemia (WM) is a rare form of non-Hodgkin's lymphoma which affects about 2700 patients per year in the US. The mutations in CXCR4 led to its overexpression on cell membranes and overactivation of the receptor signaling pathways Poulain et al., Clin Cancer Res., 22(6) 1480-1488, 2016). WHIM syndrome is a congenital immune deficiency inherited in an autosomal dominant manner which affects young children. Individuals affected by WHIM are more susceptible to life-threating bacterial and viral infections. Chronic viral infections combined with neutropenia (low levels of circulating neutrophils) and hypogammaglobulinemia (low levels of certain antibodies) were reported to be the causes of lymphoma and carcinoma developed in some affected individuals with WHIM syndrome. To date, there are no approved therapeutics to treat the underline genetic causes of WHIM and WM. The present inventors propose that inhibitors of CXCR4 may be promising therapeutic agents for the treatment of rare disorders such as WHIM and WM, and other rare disorders involving aberrant expression of CXCR4.

"Therapeutically effective amount" or "therapeutically effective dose" refers to that amount of the therapeutic agent being administered which will relieve to some extent one or more of the symptoms of the disorder being treated.

A therapeutically effective dose can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact composition, route of administration and dosage can be chosen by the individual physician in view of the subject's condition.

Dosage regimens can be adjusted to provide the optimum desired response (e.g., a therapeutic or prophylactic response). For example, a single bolus can be administered, several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure will be dictated primarily by the unique characteristics of the antibody and the particular therapeutic or prophylactic effect to be achieved.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of the antibodies or antigen-binding fragments thereof of the disclosure can be in the range of 0.5-1200 mg per subject, 0.5-1100 mg per subject, 0.5-1000 mg per subject, 0.5-900 mg per subject, 0.5-800 mg per subject, 0.5-700 mg per subject, 0.5-600 mg per subject, 0.5-500 mg per subject, 0.5-400 mg per subject, 0.5-300 mg per subject, 0.5-200 mg per subject, 0.5-100 mg per subject, 0.5-50 mg per subject, 1-1200 mg per subject, 1-1100 mg per subject, 1-1000 mg per subject, 1-900 mg per subject, 1-800 mg per subject, 1-700 mg per subject, 1-600 mg per subject, 1-500 mg per subject, 1-400 mg per subject, 1-300 mg per subject, 1-200 mg per subject, 1-100 mg per subject, or 1-50 mg per subject depending, of course, on the mode of administration. For example, an intravenous monthly dose can require about 1-1000 mg/subject. In various embodiments, the antibodies or antigen-binding fragments thereof of the disclosure can be administered at about 1-200 mg per subject, 1-150 mg per subject or 1-100 mg/subject. The total monthly dose can be administered in single or divided doses and can, at the physician's discretion, fall outside of the typical ranges given herein.

In various embodiments, a non-limiting daily dosing range for a therapeutically or prophylactically effective amount of an antibody or antigen-binding fragment thereof of the disclosure can be 0.001 to 100 mg/kg, 0.001 to 90 mg/kg, 0.001 to 80 mg/kg, 0.001 to 70 mg/kg, 0.001 to 60 mg/kg, 0.001 to 50 mg/kg, 0.001 to 40 mg/kg, 0.001 to 30 mg/kg, 0.001 to 20 mg/kg, 0.001 to 10 mg/kg, 0.001 to 5 mg/kg, 0.001 to 4 mg/kg, 0.001 to 3 mg/kg, 0.001 to 2 mg/kg, 0.001 to 1 mg/kg, 0.010 to 50 mg/kg, 0.010 to 40 mg/kg, 0.010 to 30 mg/kg, 0.010 to 20 mg/kg, 0.010 to 10 mg/kg, 0.010 to 5 mg/kg, 0.010 to 4 mg/kg, 0.010 to 3 mg/kg, 0.010 to 2 mg/kg, 0.010 to 1 mg/kg, 0.1 to 50 mg/kg, 0.1 to 40 mg/kg, 0.1 to 30 mg/kg, 0.1 to 20 mg/kg, 0.1 to 10 mg/kg, 0.1 to 5 mg/kg, 0.1 to 4 mg/kg, 0.1 to 3 mg/kg, 0.1 to 2 mg/kg, 0.1 to 1 mg/kg, 1 to 50 mg/kg, 1 to 40 mg/kg, 1 to 30 mg/kg, 1 to 20 mg/kg, 1 to 10 mg/kg, 1 to 5 mg/kg, 1 to 4 mg/kg, 1 to 3 mg/kg, 1 to 2 mg/kg, or 1 to 1 mg/kg body weight.

For repeated administrations over several days or longer, depending on the condition, the treatment is sustained until a desired suppression of symptoms occurs or until sufficient therapeutic levels are achieved, for example, to reduce pain. An exemplary dosing regimen comprises administering an initial dose of about 2 mg/kg, followed by a weekly maintenance dose of about 1 mg/kg of the anti-CXCR4 antibody, or followed by a maintenance dose of about 1 mg/kg every other week. However, other dosage regimens may be useful, depending on the pattern of pharmacokinetic decay that the practitioner wishes to achieve. For example, in some embodiments, dosing from one-four times a week is contemplated. The progress of this therapy is easily monitored by conventional techniques and assays. The dosing regimen (including the CXCR4 antagonist(s) used) can vary over time. In various embodiments, the appropriate dosage of an anti-CXCR4 antagonist antibody will depend on the anti-CXCR4 antagonist antibody (or compositions thereof) employed, the type and severity of headache (e.g., migraine) to be treated, whether the agent is administered for preventive or therapeutic purposes, previous therapy, the patient's clinical history and response to the agent, and the discretion of the attending physician. Typically, the clinician will administer an anti-CXCR4 antagonist antibody, until a dosage is reached that achieves the desired result. Dose and/or frequency can vary over course of treatment.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In various embodiments, the total dose administered will achieve a plasma antibody concentration in the range of, e.g., about 1 to 1000 μg/ml, about 1 to 750 μg/ml, about 1 to 500 μg/ml, about 1 to 250 μg/ml, about 10 to 1000 μg/ml, about 10 to 750 μg/ml, about 10 to 500 μg/ml, about 10 to 250 μg/ml, about 20 to 1000 μg/ml, about 20 to 750 μg/ml, about 20 to 500 μg/ml, about 20 to 250 μg/ml, about 30 to 1000 μg/ml, about 30 to 750 μg/ml, about 30 to 500 μg/ml, about 30 to 250 μg/ml.

Toxicity and therapeutic index of the pharmaceutical compositions of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effective dose is the therapeutic index and it can be expressed as the ratio $LD_{50}/ED_{50}$. Compositions that exhibit large therapeutic indices are generally preferred.

In various embodiments, single or multiple administrations of the pharmaceutical compositions are administered depending on the dosage and frequency as required and tolerated by the subject. In any event, the composition should provide a sufficient quantity of at least one of the antibodies or antigen-binding fragments thereof disclosed herein to effectively treat the subject. The dosage can be administered once but may be applied periodically until either a therapeutic result is achieved or until side effects warrant discontinuation of therapy.

The dosing frequency of the administration of the antibody or antigen-binding fragment thereof pharmaceutical composition depends on the nature of the therapy and the particular disease being treated. The subject can be treated at regular intervals, such as weekly or monthly, until a desired therapeutic result is achieved. Exemplary dosing frequencies include, but are not limited to: once weekly without break; once weekly, every other week; once every 2 weeks; once every 3 weeks; weakly without break for 2 weeks, then monthly; weakly without break for 3 weeks, then monthly; monthly; once every other month; once every three months; once every four months; once every five months; or once every six months, or yearly.

Combination Therapy

As used herein, the terms "co-administration", "co-administered" and "in combination with", referring to the antibodies or antigen-binding fragments thereof of the disclosure and one or more other therapeutic agents, is intended to mean, and does refer to and include the following: simultaneous administration of such combination of antibodies or antigen-binding fragments thereof of the disclosure and therapeutic agent(s) to a subject in need of treatment, when such components are formulated together into a single dosage form which releases said components at substantially the same time to said subject; substantially simultaneous administration of such combination of antibodies or antigen-binding fragments thereof of the disclosure and therapeutic agent(s) to a subject in need of treatment, when such components are formulated apart from each other into separate dosage forms which are taken at substantially the same time by said subject, whereupon said components are released at substantially the same time to said subject; sequential administration of such combination of antibodies or antigen-binding fragments thereof of the disclosure and therapeutic agent(s) to a subject in need of treatment, when such components are formulated apart from each other into separate dosage forms which are taken at consecutive times by said subject with a significant time interval between each administration, whereupon said components are released at substantially different times to said subject; and sequential administration of such combination of antibodies or antigen-binding fragments thereof of the disclosure and therapeutic agent(s) to a subject in need of treatment, when such components are formulated together into a single dosage form which releases said components in a controlled manner whereupon they are concurrently, consecutively, and/or overlappingly released at the same and/or different times to said subject, where each part may be administered by either the same or a different route.

In another aspect, the present invention relates to combination therapies designed to treat a cancer, or an infectious disease, in an subject, comprising administering to the subject a therapeutically effective amount of an isolated antibody or antigen-binding fragment of the present invention, and b) one or more additional therapies selected from the group consisting of immunotherapy, chemotherapy, small molecule kinase inhibitor targeted therapy, surgery, radiation therapy, vaccination protocols, and stem cell transplantation, wherein the combination therapy provides increased cell killing of tumor cells, i.e., a synergy exists between the isolated antibody or antigen-binding fragment and the additional therapies when co-administered.

In various embodiments, the immunotherapy is selected from the group consisting of: treatment using agonistic, antagonistic, or blocking antibodies to co-stimulatory or co-inhibitory molecules (immune checkpoints) such as PD-1, PD-L1, OX-40, CD137, GITR, LAGS, TIM-3, and VISTA; treatment using bispecific T cell engaging antibodies (BiTE®) such as blinatumomab: treatment involving administration of biological response modifiers such as IL-2, IL-12, IL-15, IL-21, GM-CSF and IFN-α, IFN-β and IFN-γ; treatment using therapeutic vaccines such as sipuleucel-T; treatment using dendritic cell vaccines, or tumor antigen peptide vaccines; treatment using chimeric antigen receptor (CAR)-T cells; treatment using CAR-NK cells; treatment using tumor infiltrating lymphocytes (TILs); treatment using adoptively transferred anti-tumor T cells (ex vivo expanded and/or TCR transgenic); treatment using TALL-104 cells; and treatment using immunostimulatory agents such as Toll-like receptor (TLR) agonists CpG and imiquimod.

In various embodiments, the additional therapy comprises an antibody that specifically binds an immune-checkpoint protein antigen from the list including, but not limited to, CD276, CD272, CD152, CD223, CD279, CD274, TIM-3 and B7-H4; or any immune-checkpoint protein antigen antibody taught in the art. In various embodiments, the PD-1 inhibitor used in the combination therapy methods is selected from the group consisting of, but not limited to, pembrolizumab (Merck), nivolumab (Bristol-Myers Squibb), and pidilizumab (Medivation). In various embodiments, the PD-1 inhibitor is pembrolizumab. In various embodiments, the PD-1 inhibitor is nivolumab. In various embodiments, the PD-1 inhibitor is pidilizumab. In various embodiments, between about 0.1 mg/kg to about 10 mg/kg of PD-1 inhibitor is administered. In various embodiments, between about 1 mg/kg to about 15 mg/kg of PD-1 inhibitor is administered.

A wide array of conventional compounds has been shown to have anti-neoplastic activities. These compounds have been used as pharmaceutical agents in chemotherapy to shrink solid tumors, prevent metastases and further growth, or decrease the number of malignant T-cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments When the antibody or antigen-binding fragment disclosed herein is administered in combination with another conventional anti-neoplastic agent, either concomitantly or sequentially, such antibody or antigen-binding fragment may enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant T-cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In various embodiments, the chemotherapy comprises a chemotherapeutic agent selected from the group consisting of: daunorubicin, dactinomycin, doxorubicin, bleomycin, mitomycin, nitrogen mustard, chlorambucil, melphalan, cyclophosphamide, 6-mercaptopurine, 6-thioguanine, bendamustine, cytarabine (CA), 5-fluorouracil (5-FU), floxuridine (5-FUdR), methotrexate (MTX), colchicine, vincristine, vinblastine, etoposide, teniposide, cisplatin, carboplatin, oxaliplatin, pentostatin, cladribine, cytarabine, gemcitabine, pralatrexate, mitoxantrone, diethylstilbestrol (DES), fluradabine, ifosfamide, hydroxyureataxanes (such as paclitaxel and doxetaxel) and/or anthracycline antibiotics, as well as combinations of agents such as, but not limited to, DA-EPOCH, CHOP, CVP or FOLFOX.

In various embodiments, the small molecule kinase inhibitor targeted therapy comprises a small molecule kinase inhibitor selected from the group consisting of Bruton's tyrosine kinase (BTK) inhibitor, phosphatidylinositol-3-kinase (PI3K) inhibitor, SYK inhibitor (e.g., entospletinib), AKT inhibitor, mTOR inhibitor, Src inhibitor, JAK/STAT inhibitor, Ras/Raf/MEK/ERK inhibitor, and Aurora inhibitor (see, D'Cruz et al, Expert Opin Pharmacother, 14(6): 707-21, 2013).

In various embodiments, the combination therapy comprises administering the antibody or antigen-binding fragment thereof and the one or more additional therapies simultaneously. In various embodiments, antibody or antigen-binding fragment thereof composition and the one or more additional therapies are administered sequentially, i.e., the antibody or antigen-binding fragment thereof composition is administered either prior to or after the administration of the one or more additional therapies.

In various embodiments, the administrations of the antibody or antigen-binding fragment thereof composition and the one or more additional therapies are concurrent, i.e., the administration period of the antibody or antigen-binding fragment thereof composition and the one or more additional therapies overlap with each other.

In various embodiments, the administrations of the antibody or antigen-binding fragment thereof composition and the one or more additional therapies are non-concurrent. For example, in various embodiments, the administration of the antibody or antigen-binding fragment thereof composition is terminated before the one or more additional therapies is administered. In various embodiments, the administration of the one or more additional therapies is terminated before the antibody or antigen-binding fragment thereof composition is administered.

When the antibody or antigen-binding fragment thereof disclosed herein is administered in combination with one or more additional therapies, either concomitantly or sequentially, such antibody or antigen-binding fragment thereof may enhance the therapeutic effect of the one or more additional therapies or overcome cellular resistance to the one or more additional therapies. This allows for decreased dosage or duration of the one or more additional therapies, thereby reducing the undesirable side effects, or restores the effectiveness of the one or more additional therapies.

Diagnostic Uses

In another aspect, the present invention provides a method for detecting in vitro or in vivo the presence of human CXCR4 peptide in a sample, e.g., for diagnosing a human CXCR4-related disorder. In some methods, this is achieved by contacting a sample to be tested, along with a control sample, with a human sequence antibody or a human monoclonal antibody of the invention, or an antigen-binding portion thereof (or a bispecific or multispecific molecule), under conditions that allow for formation of a complex between the antibody and human CXCR4. Complex formation is then detected (e.g., using an ELISA) in both samples, and any statistically significant difference in the formation of complexes between the samples is indicative the presence of human CXCR4 antigen in the test sample.

In various embodiments, methods are provided for detecting a CXCR4-related disorder or confirming the diagnosis of a CXCR4-related disorder in a subject. The method includes contacting a biological sample from the subject with an isolated antibody or antigen-biding fragment thereof of the invention and detecting binding of the isolated human monoclonal antibody or antigen-binding fragment thereof to the sample. An increase in binding of the isolated human monoclonal antibody or antigen-binding fragment thereof to the sample as compared to binding of the isolated human monoclonal antibody or antigen-binding fragment thereof to a control sample detects a CXCR4-related disorder in the subject or confirms the diagnosis of a CXCR4-related disorder in the subject. The control can be a sample from a subject known not to have a CXCR4-related disorder, or a standard value. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, and spinal fluid.

In one embodiment, a kit is provided for detecting CXCR4 in a biological sample, such as a blood sample. Kits for detecting a polypeptide will typically comprise a human antibody that specifically binds CXCR4, such as any of the antibodies disclosed herein. In some embodiments, an antibody fragment, such as an Fv fragment is included in the kit. For in vivo uses, the antibody can be a scFv fragment. In a further embodiment, the antibody is labeled (for example, with a fluorescent, radioactive, or an enzymatic label).

In one embodiment, a kit includes instructional materials disclosing means of use of an antibody that specifically binds CXCR4. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting CXCR4 in a biological sample generally includes the steps of contacting the biological sample with an antibody which specifically reacts, under immunologically reactive conditions, to CXCR4. The antibody is allowed to specifically bind under immunologically reactive conditions to form an immune complex, and the presence of the immune complex (bound antibody) is detected directly or indirectly.

In various embodiments, the antibodies or antigen-binding fragments can be labeled or unlabeled for diagnostic purposes. Typically, diagnostic assays entail detecting the formation of a complex resulting from the binding of an antibody to CXCR4. The antibodies can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the antibodies can be used in assays, such as agglutination assays. Unlabeled antibodies can also be used in combination with another (one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

The antibody or antigen-binding fragment provided herein may also be used in a method of detecting the susceptibility of a mammal to certain diseases. To illustrate, the method can be used to detect the susceptibility of a mammal to diseases which progress based on the amount of CXCR4 present on cells and/or the number of CXCR4-positive cells in a mammal. In one embodiment, the application provides a method of detecting susceptibility of a mammal to a tumor. In this embodiment, a sample to be tested is contacted with an antibody which binds to CXCR4 or portion thereof under conditions appropriate for binding of said antibody thereto, wherein the sample comprises cells which express CXCR4 in normal individuals. The binding of antibody and/or amount of binding is detected, which indicates the susceptibility of the individual to a tumor, wherein higher levels of receptor correlate with increased susceptibility of the individual to a tumor.

In various embodiments, the antibodies or antigen-binding fragments are attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}K$, $^{52}Fe$, $^{57}Co$, $^{67}Cu$, $^{67}Ga$, $^{68}Ga$, $^{123}I$, $^{125}I$, $^{131}I$, $^{132}I$, or $^{99}Tc$. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography.

Immunoscintigraphy using antibodies or antigen-binding fragments directed at CXCR4 may be used to detect and/or diagnose cancers and vasculature. For example, monoclonal antibodies against the CXCR4 marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically, 0.1-100 millicuries per dose of imaging agent, or 1-10 millicuries, or 2-5 millicuries are administered. Thus, the compositions disclosed are useful as imaging agents comprising a targeting moiety conjugated to a radioactive moiety comprise 0.1-100 millicuries, in some embodiments 1-10 millicuries, in some embodiments 2-5 millicuries, in some embodiments 1-5 millicuries.

Immunoconjugates

The application further provides immunoconjugates comprising an antibody or antigen-binding fragment thereof of the present invention conjugated (or linked) directly or indirectly to an effector molecule. In this regard, the term "conjugated" or "linked" refers to making two polypeptides into one contiguous polypeptide molecule. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. In various embodiments, an antibody or antigen-binding fragment is joined to an effector molecule. In other embodiments, an antibody or antigen-binding fragment joined to an effector molecule is further joined to a lipid, a protein or peptide to increase its half-life in the body. Accordingly in various embodiments, the antibodies of the present disclosure may be used to deliver a variety of effector molecules.

The effector molecule can be a detectable label, an immunotoxin, cytokine, chemokine, therapeutic agent, or chemotherapeutic agent.

Specific, non-limiting examples of immunotoxins include, but are not limited to, abrin, ricin, Pseudomonas exotoxin (PE, such as PE35, PE37, PE38, and PE40), diphtheria toxin (DT), botulinum toxin, cholix toxin, or modified toxins thereof, or other toxic agents that directly or indirectly inhibit cell growth or kill cells.

A "cytokine" is class of proteins or peptides released by one cell population which act on another cell as intercellular mediators. Cytokines can act as an immune-modulating agent. Examples of cytokines include lymphokines, monokines, growth factors and traditional polypeptide hormones. Thus, embodiments may utilize an interferon (e.g., IFN-α, IFN-β, and IFN-γ); tumor necrosis factor super family (TNFSF) member; human growth hormone; thyroxine; insulin; proinsulin; relaxin; prorelaxin; follicle stimulating hormone (FSH); thyroid stimulating hormone (TSH); luteinizing hormone (LH); hepatic growth factor; prostaglandin, fibroblast growth factor; prolactin; placental lactogen, OB protein; TNF-α; TNF-β; integrin; thrombopoietin (TPO); a nerve growth factor such as NGF-β.; platelet-growth factor; TGF-α; TGF-β; insulin-like growth factor-I and -II; erythropoietin (EPO); colony stimulating factors (CSFs) such as macrophage-CSF (M-CSF); granulocyte-macrophage-CSF (GM-CSF); and granulocyte-CSF (G-CSF); an interleukin (IL-1 to IL-21), kit-ligand or FLT-3, angiostatin, thrombospondin, or endostatin. These cytokine include proteins from natural sources or from recombinant cell culture and biologically active equivalents of the native sequence cytokines.

Chemokines can also be conjugated to the antibodies disclosed herein. Chemokines are a superfamily of small (approximately about 4 to about 14 kDa), inducible and secreted pro-inflammatory cytokines that act primarily as chemoattractants and activators of specific leukocyte cell subtypes. Chemokine production is induced by inflammatory cytokines, growth factors and pathogenic stimuli. The chemokine proteins are divided into subfamilies (alpha, beta, and delta) based on conserved amino acid sequence motifs and are classified into four highly conserved groups—CXC, CC, C and CX3C, based on the position of the first two cysteines that are adjacent to the amino terminus. To date, more than 50 chemokines have been discovered and there are at least 18 human seven-transmembrane-domain (7TM) chemokine receptors. Chemokines of use include, but are not limited to, RANTES, MCAF, MCP-1, and fractalkine.

The therapeutic agent can be a chemotherapeutic agent. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2.sup.nd ed., 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Useful chemotherapeutic agents for the preparation of immunoconjugates include auristatin, dolastatin, MMAE, MMAF, AFP, DM1, AEB, doxorubicin, daunorubicin, methotrexate, melphalan, chlorambucil, vinca alkaloids, 5-fluorouridine, mitomycin-C, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbazine, topotecan, nitrogen mustards, cytoxan, etoposide, BCNU, irinotecan, camptothecins, bleomycin, idarubicin, dactinomycin, plicamycin, mitoxantrone, asparaginase, vinblastine, vincristine, vinorelbine, paclitaxel, and docetaxel and salts, solvents and derivatives thereof. In various embodiments, the chemotherapeutic agent is auristatin E (also known in the art as dolastatin-10) or a derivative thereof as well as pharmaceutically salts or solvates thereof. Typical auristatin derivatives include DM1, AEB, AEVB, AFP, MMAF, and MMAE. The synthesis and structure of auristatin E and its derivatives, as well as linkers, are described in, e.g., U.S. Patent Application Publication No. 20030083263; U.S. Patent Application Publication No. 20050238629; and U.S. Pat. No. 6,884,869 (each of which is incorporated by reference herein in its entirety). In various embodiments, the therapeutic agent is an auristatin or an auristatin derivative. In various embodiments, the auristatin derivative is dovaline-valine-dolaisoleunine-dolaproine-phenylalanine (MMAF) or monomethyauristatin E (MMAE). In various embodiments, the therapeutic agent is a maytansinoid or a maytansinol analogue. In various embodiments, the maytansinoid is DM1.

The effector molecules can be linked to an antibody or antigen-binding fragment of the present invention using any number of means known to those of skill in the art. Both covalent and noncovalent attachment means may be used. The procedure for attaching an effector molecule to an antibody varies according to the chemical structure of the effector molecule. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

Procedures for conjugating the antibodies with the effector molecules have been previously described and are within the purview of one skilled in the art. For example, procedures for preparing enzymatically active polypeptides of the immunotoxins are described in WO84/03508 and WO85/03508, which are hereby incorporated by reference for purposes of their specific teachings thereof. Other techniques are described in Shih et al., Int. J. Cancer 41:832-839 (1988); Shih et al., Int. J. Cancer 46:1101-1106 (1990); Shih et al., U.S. Pat. No. 5,057,313; Shih Cancer Res. 51:4192, International Publication WO 02/088172; U.S. Pat. No. 6,884,869; International Patent Publication WO 2005/081711; U.S. Published Application 2003-0130189 A; and US Patent Application No. 20080305044, each of which is incorporated by reference herein for the purpose of teaching such techniques.

An immunoconjugate of the present invention retains the immunoreactivity of the antibody or antigen-binding fragment, e.g., the antibody or antigen-binding fragment has approximately the same, or only slightly reduced, ability to bind the antigen after conjugation as before conjugation. As used herein, an immunoconjugate is also referred to as an antibody drug conjugate (ADC).

Bispecific Molecules

In another aspect, the present invention features bispecific molecules comprising an anti-CXCR4 antibody, or antigen-binding fragment thereof, of the invention. An antibody of the invention, or antigen-binding fragment thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results. In various embodiments, the invention includes bispecific molecules capable of binding both to FcγR or FcαR expressing effector cells (e.g., monocytes, macrophages or polymorphonuclear cells (PMNs)), and to target cells expressing PD. In such embodiments, the bispecific molecules target CXCR4 expressing cells to effector cell and trigger Fc receptor-mediated effector cell activities, e.g., phagocytosis of an CXCR4 expressing cells, antibody dependent cell-mediated cytotoxicity (ADCC), cytokine release, or generation of superoxide anion. Methods of preparing the bispecific molecules of the present invention are well known in the art.

Polynucleotides and Antibody Expression

The application further provides polynucleotides comprising a nucleotide sequence encoding an anti-CXCR4 antibody or antigen-binding fragment thereof. Because of the degeneracy of the genetic code, a variety of nucleic acid sequences encode each antibody amino acid sequence. The application further provides polynucleotides that hybridize under stringent or lower stringency hybridization conditions, e.g., as defined herein, to polynucleotides that encode an antibody that binds to human CXCR4.

Stringent hybridization conditions include, but are not limited to, hybridization to filter-bound DNA in 6×SSC at about 45° C. followed by one or more washes in 0.2×SSC/ 0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3).

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR. In one embodiment, the codons that are used comprise those that are typical for human or mouse (see, e.g., Nakamura, Y., Nucleic Acids Res. 28: 292 (2000)).

A polynucleotide encoding an antibody may also be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably polyA+ RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

The present invention is also directed to host cells that express a CXCR4 and/or the anti-CXCR4 antibodies of the invention. A wide variety of host expression systems known in the art can be used to express an antibody of the present invention including prokaryotic (bacterial) and eukaryotic expression systems (such as yeast, baculovirus, plant, mammalian and other animal cells, transgenic animals, and hybridoma cells), as well as phage display expression systems.

An antibody of the invention can be prepared by recombinant expression of immunoglobulin light and heavy chain genes in a host cell. To express an antibody recombinantly, a host cell is transformed, transduced, infected or the like with one or more recombinant expression vectors carrying DNA fragments encoding the immunoglobulin light and/or heavy chains of the antibody such that the light and/or heavy chains are expressed in the host cell. The heavy chain and the light chain may be expressed independently from different promoters to which they are operably-linked in one vector or, alternatively, the heavy chain and the light chain may be expressed independently from different promoters to which they are operably-linked in two vectors one expressing the heavy chain and one expressing the light chain. Optionally, the heavy chain and light chain may be expressed in different host cells.

Additionally, the recombinant expression vector can encode a signal peptide that facilitates secretion of the antibody light and/or heavy chain from a host cell. The antibody light and/or heavy chain gene can be cloned into the vector such that the signal peptide is operably-linked in-frame to the amino terminus of the antibody chain gene. The signal peptide can be an immunoglobulin signal peptide or a heterologous signal peptide. Preferably, the recombinant antibodies are secreted into the medium in which the host cells are cultured, from which the antibodies can be recovered or purified.

An isolated DNA encoding a HCVR can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification. The heavy chain constant region can be of any type, (e.g., IgG, IgA, IgE, IgM or IgD), class (e.g., IgG$_1$, IgG$_2$, IgG$_3$ and IgG$_4$) or subclass constant region and any allotypic variant thereof as described in Kabat (supra).

An isolated DNA encoding a LCVR region may be converted to a full-length light chain gene (as well as to a Fab light chain gene) by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

In addition to the antibody heavy and/or light chain gene(s), a recombinant expression vector of the invention carries regulatory sequences that control the expression of the antibody chain gene(s) in a host cell. The term "regulatory sequence" is intended to include promoters, enhancers and other expression control elements (e.g., polyadenylation signals), as needed, that control the transcription or translation of the antibody chain gene(s). The design of the expression vector, including the selection of regulatory sequences may depend on such factors as the choice of the host cell to be transformed, the level of expression of protein desired. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and/or polyoma virus.

Additionally, the recombinant expression vectors of the invention may carry additional sequences, such as sequences that regulate replication of the vector in host cells (e.g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (dhfr) gene (for use in dhfr-minus host cells with methotrexate selection/amplification), the neo gene (for G418 selection), and glutamine synthetase (GS) in a GS-negative cell line (such as NSO) for selection/amplification.

For expression of the light and/or heavy chains, the expression vector(s) encoding the heavy and/or light chains is introduced into a host cell by standard techniques e.g. electroporation, calcium phosphate precipitation, DEAE-dextran transfection, transduction, infection and the like. Although it is theoretically possible to express the antibodies of the invention in either prokaryotic or eukaryotic host cells, eukaryotic cells are preferred, and most preferably mammalian host cells, because such cells are more likely to assemble and secrete a properly folded and immunologically active antibody. Preferred mammalian host cells for expressing the recombinant antibodies of the invention include Chinese Hamster Ovary (CHO cells) [including dhfr minus CHO cells, as described in Urlaub and Chasin, Proc. Natl. Acad. Sci. USA 77:4216-20, 1980, used with a DHFR selectable marker, e.g. as described in Kaufman and Sharp, J. Mol. Biol. 159:601-21, 1982], NSO myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown under appropriate conditions known in the art. Antibodies can be recovered from the host cell and/or the culture medium using standard purification methods.

The invention provides a host cell comprising a nucleic acid molecule of the present invention. Preferably a host cell of the invention comprises one or more vectors or constructs comprising a nucleic acid molecule of the present invention. For example, a host cell of the invention is a cell into which a vector of the invention has been introduced, said vector comprising a polynucleotide encoding a LCVR of an antibody of the invention and/or a polynucleotide encoding a HCVR of the invention. The invention also provides a host cell into which two vectors of the invention have been introduced; one comprising a polynucleotide encoding a LCVR of an antibody of the invention and one comprising a polynucleotide encoding a HCVR present in an antibody of the invention and each operably-linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes.

Once expressed, the intact antibodies, individual light and heavy chains, or other immunoglobulin forms of the present invention can be purified according to standard procedures of the art, including ammonium sulfate precipitation, ion exchange, affinity (e.g., Protein A), reverse phase, hydrophobic interaction column chromatography, hydroxyapatite chromatography, gel electrophoresis, and the like. Standard procedures for purification of therapeutic antibodies are described, for example, by Feng L1, Joe X. Zhou, Xiaoming Yang, Tim Tressel, and Brian Lee in an article entitled "Current Therapeutic Antibody Production and Process Optimization" (BioProcessing Journal, September/October 2005)(incorporated by reference in its entirety for purposes of teaching purification of therapeutic antibodies). Additionally, standard techniques for removing viruses from recombinantly expressed antibody preparations are also known in the art (see, for example, Gerd Kern and Mani Krishnan, "Viral Removal by Filtration: Points to Consider" (Biopharm International, October 2006)). The effectiveness of filtration to remove viruses from preparations of therapeutic antibodies is known to be at least in part dependent on the concentration of protein and/or the antibody in the solution to be filtered. The purification process for antibodies of the present invention may include a step of filtering to remove viruses from the mainstream of one or more chromatography operations. Preferably, prior to filtering through a pharmaceutical grade nanofilter to remove viruses, a chromatography mainstream containing an antibody of the present invention is diluted or concentrated to give total protein and/or total antibody concentration of about 1 g/L to about 3 g/L. Even more preferably, the nanofilter is a DV20 nanofilter (e.g., Pall Corporation; East Hills, N.Y.). Substantially pure immunoglobulins of at least about 90%, about 92%, about 94% or about 96% homogeneity are preferred, and about 98 to about 99% or more homogeneity most preferred, for pharmaceutical uses. Once purified, partially or to homogeneity as desired, the sterile antibodies may then be used therapeutically, as directed herein.

In view of the aforementioned discussion, the present invention is further directed to an antibody obtainable by a process comprising the steps of culturing a host cell including, but not limited to a mammalian, plant, bacterial, transgenic animal, or transgenic plant cell which has been transformed by a polynucleotide or a vector comprising nucleic acid molecules encoding antibodies of the invention so that the nucleic acid is expressed and, optionally, recovering the antibody from the host cell culture medium.

In certain aspects, the present application provides hybridoma cell lines, as well as to the monoclonal antibodies produced by these hybridoma cell lines. The cell lines disclosed have uses other than for the production of the monoclonal antibodies. For example, the cell lines can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-CXCR4 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a rearranged anti-CXCR4 light or heavy chain can be isolated (e.g., by PCR) or cDNA libraries can be prepared from mRNA isolated from the cell lines, and cDNA clones encoding an anti-CXCR4 immunoglobulin chain can be isolated. Thus, nucleic acids encoding the heavy and/or light chains of the antibodies or portions thereof can be obtained and used in accordance with recombinant DNA techniques for the production of the specific immunoglobulin, immunoglobulin chain, or variants thereof (e.g., humanized immunoglobulins) in a variety of host T-cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host T-cell by an appropriate method (e.g., transformation, transfection, electroporation, infection), such that the nucleic acid is operably linked to one or more expression control elements (e.g., in the vector or integrated into the host T-cell genome). For production, host T-cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host T-cells or medium). It will be appreciated that the method of production encompasses expression in a host T-cell of a transgenic animal (see e.g., WO 92/03918, GenPharm International, published Mar. 19, 1992)(incorporated by reference in its entirety).

Host cells can also be used to produce portions, or fragments, of intact antibodies, e.g., Fab fragments or scFv molecules by techniques that are conventional. For example, it may be desirable to transfect a host cell with DNA encoding either the light chain or the heavy chain of an antibody of this invention. Recombinant DNA technology may also be used to remove some or all the DNA encoding either or both of the light and heavy chains that is not necessary for binding to human CXCR4. The molecules expressed from such truncated DNA molecules are also encompassed by the antibodies of the invention.

Methods for expression of single chain antibodies and/or refolding to an appropriate active form, including single chain antibodies, from bacteria such as E. coli have been described and are well-known and are applicable to the antibodies disclosed herein (see, e.g., Buchner et al., Anal. Biochem. 205:263-270, 1992; Pluckthun, Biotechnology 9:545, 1991; Huse et al., Science 246:1275, 1989 and Ward et al., Nature 341:544, 1989, all incorporated by reference herein).

Often, functional heterologous proteins from E. coli or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., Biochemistry 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two-chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. Excess oxidized glutathione or other oxidizing low molecular weight compounds can be added to the refolding solution after redox shuffling is completed.

In addition to recombinant methods, the antibodies, labeled antibodies and antigen-binding fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield et al., J. Am. Chem. Soc. 85:2149-2156, 1963, and Stewart et al., Solid Phase Peptide Synthesis, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

The following examples are offered to more fully illustrate the invention but are not construed as limiting the scope thereof.

Example 1

Generation of Monoclonal Antibodies Targeting Specifically to Human CXCR4

Balb/c and C57BI/6 mouse (22 gms, 6-8 weeks old) were each immunized bi-weekly (6 total immunizations) with 100 μg or 50 μg hCXCR4 plasmid DNA with Gene Gun, and splenocytes were harvested 4 days after the final immunization for fusion with myeloma cell line NS0 from ATCC (Allendale, N.J.). Electric fusion methods are used to obtain hybridoma cells and then the hybridoma supernatants are screened for antigen binding, ligand blocking, IgG binning, reference antibody binding, and FACS binding. 23 murine mAbs were ultimately selected from the initial screens for subcloning (limited dilution method). BD Cell MAb Medium was used to grow hybridomas in roller bottles for the collection of supernatants for antibody production. mAbs were purified with Protein A affinity chromatography. Estimated purity of mAbs was higher than 90% based on SDS-PAGE Coomassie staining. Secondary screening of the 23 mAbs comprised: human CXCR4 binding assays (FACS) and evolution of functional effects in a CXCR4 cAMP assay (Dynamic cAMP Assay, Cisbio).

Figure 2:
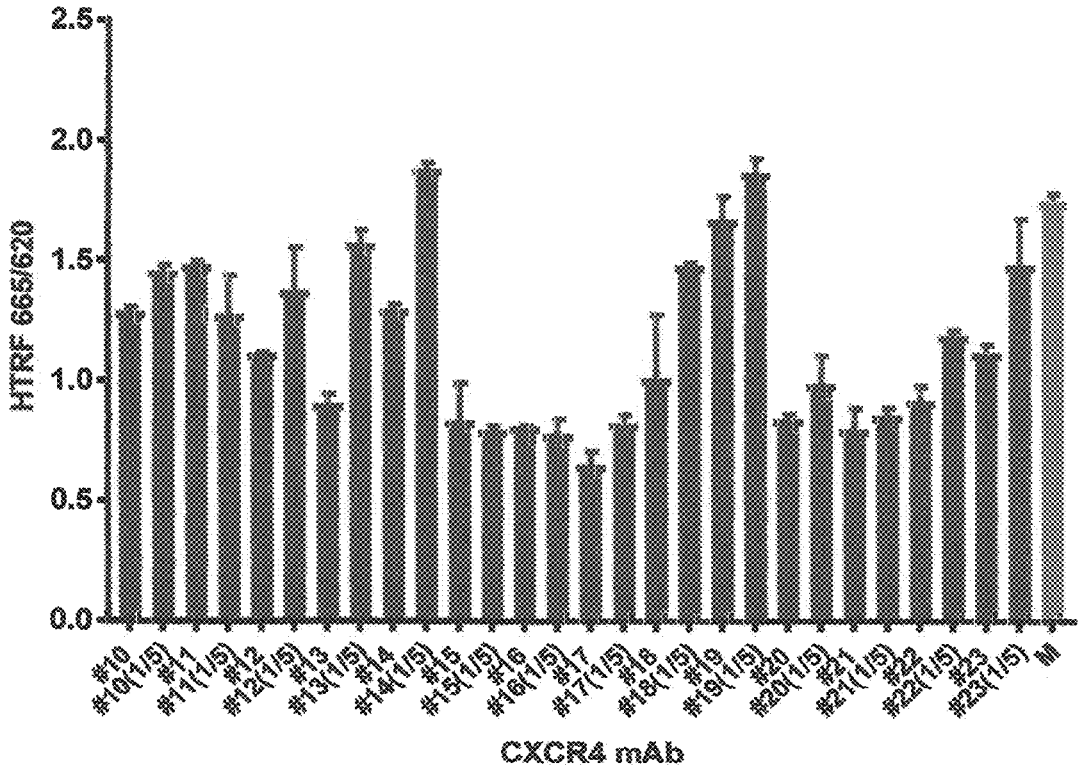
FIG. 2 is a bar graph depicting the CXCR4 cAMP functional assay data for murine mAbs #10-#23.
Figure 3:
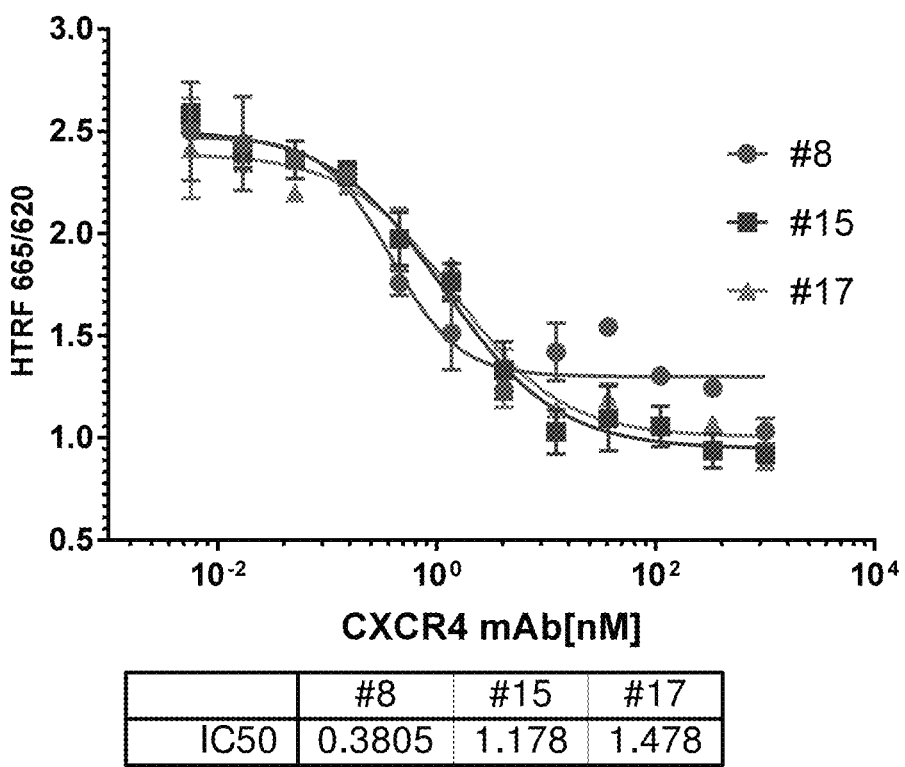
FIG. 3 is line graph depicting the CXCR4 cAMP functional assay data (IC50) for murine mAbs #8, #15 and #17.

To evaluate the functional effects of CXCR4, the 23 purified mAbs were assessed in recombinant CHO cells stably expressing CXCR4 receptors using a cAMP assay (Dynamic cAMP Assay, Cisbio). Recombinant CHO cells expressing tagged CXCR4 receptors were added to 96-well half-area white plates (40,000 cells per well) and were treated with SDF-1 at concentrations from 0.5 pM to 100 nM and with Forskolin at 500 nM to assess agonist activity. To assess antagonist activity, CXCR4 mAb were added to cells at 0.5 pM to 1 μM for 30 min at room temperature. 5.0 nM of SDF-1 corresponding to the EC50, was then added and cells were further incubated for 30 min at room temperature. The reaction was stopped by adding detection mix to all wells followed by a 60 min incubation at room temperature. The assay plates were read on an EnVision® Multilabel Plate Reader (Perkin Elmer; Waltham, Mass., USA) at an emission wavelength of 665 nm. The ratio of HTRF 665/620 is used to indicate the blocking of ligand binding. The lower the ratio, the higher degree of the blockage. All results were analyzed by nonlinear regression curve fit using Graph Pad Prism version 6 (Graph Pad Inc., La Jolla, Calif.). The functional assay data for the 23 mAbs are summarized in FIG. 1 and FIG. 2. The IC50 of the top three Abs are summarized in FIG. 3 and Table 3:

TABLE 3

| Murine mAb | mAb ID | HuCXCR4 Binding IC50 (nM) |
|---|---|---|
| A8 | 132F3F3H11 | .3805 |
| A15 | 201D10A12C1 | 1.178 |
| A17 | 201D10E9F2 | 1.478 |

Based on the cumulative results of the binding and secondary assays, purified murine mAb 132F3F3H11 ("A8"), mAb 201 D10A12C1 ("A15") and mAb 201D10E9F2 (#A17) were selected for sequencing and further analysis. Total RNA was extracted from frozen hybridoma cells following the technical manual of TRIzol® Reagent. The total RNA was analyzed by agarose gel electrophoresis. Total RNA was reverse transcribed into cDNA using isotype-specific anti-sense primers or universal primers following the technical manual of PrimeScript™ 1st Strand cDNA Synthesis Kit. PCR was then performed to amplify the variable regions (heavy and light chains) of the antibodies, which were then cloned into a standard cloning vector separately and sequenced. Murine mAbs 132F3F3H11 ("A8") and 201D10A12C1 ("A15") comprise the heavy chain variable region sequences set forth in SEQ ID NOs: 14 and 16, respectively, and the light chain variable region sequences set forth in SEQ ID NOs: 18 and 20, respectively. The heavy chain variable regions of mAbs 132F3F3H11 ("A8") and 201D10A12C1 ("A15") are encoded by the nucleic acid sequences set forth in SEQ ID NOs: 15 and 17, respectively, and the light chain variable regions are encoded by the nucleic acid sequences set forth in SEQ ID NOs: 19 and 21, respectively. Murine mAb 201 D10E9F2 ("A17") was found to have HCVR and LCVR sequences identical to mAb A15.

Example 2

Generation of a Chimeric IgG1 Targeting Human CXCR4

Using the HCVR and LCVR sequences of mAb 201D10A12C1 ("A15"), a murine-human IgG1 chimeric Fab (hereinafter "chimeric IgG1") was prepared and which comprised the heavy chain sequence set forth in SEQ ID NO: 22 and the light chain sequence set forth in SEQ ID NO: 23.

The DNA sequences encoding the chimeric IgG heavy and light chains were synthesized and inserted into pTT5 vector to construct the expression plasmids of full-length IgGs. Expression of chimeric IgG was conducted in HEK293 cell culture and the supernatants were purified with protein A affinity column. The purified antibody was buffer-exchanged into PBS using PD-10 desalting column. The concentration and purity of the purified protein were determined by $OD_{280}$ and SDS-PAGE, respectively. The purified chimeric IgG migrated as ~170 kDa band in SDS-PAGE under non-reducing conditions. Evaluating by the SDS-PAGE result, the purity of the IgGs was >95%.

Example 3

Generation of Humanized Abs Specifically Targeting Human CXCR4

A CDR grafting and back mutation method was used to prepare humanized anti-CXCR4 mAbs derived from murine mAb 201D10A12C1 ("A15"). The structure of parental antibody was modelled by computer-aided homology modelling program. Humanized antibodies were designed using CDR grafting and subsequent replaced putative back mutation sites of grafted antibody. Briefly, the CDRs of parental mAb A15 were grafted into the human acceptors to obtain humanized light chains and humanized heavy chains for the parental antibody. The sequences of six humanized heavy chain variable regions (referred to as VH1, VH2, VH3, VH4, VH5, and VH6) are set forth in SEQ ID NOs: 24-29, respectively and the sequences of three humanized light chain variable regions (referred to as VL1, VL2, and VL3) are set forth in SEQ ID NOs: 30-32, respectively were paired with each other for affinity ranking experiments.

The DNA sequences encoding the chimeric antibody and humanized IgG heavy and light chains were synthesized and inserted into pCDNA3.4 vector to construct the expression plasmids of full-length IgGs. 18 humanized Abs were expressed in Expi293F cell culture, and then the cells were spun down. For affinity ranking, the supernatants were assayed by FACS against cell lines for the assessment of binding activity. Positive cells lines (CXCR4 E4) were cultured following the protocol and harvested by centrifugation. About $1 \times 10^5$ cells per well were washed with 1*PBS and incubated in a serial dilution of antibodies for 30 minutes at 4° C. After washing with PBS, secondary antibody [1 μg/ml Alexa Fluor® 647 AffiniPure® Goat Anti-Human IgG (H+L)] was added to the cells and incubated in PBS for 30 minutes at 4° C. After washing with PBS, cells were analyzed for binding by using FACS Calibur (BD Bioscience, San Jose, CA) and Flowjo® software. The antibodies were ranked by EC50.

The binding data is summarized in Table 4 below:

TABLE 4

| Humanized Antibody | | EC50 (μg/ml) | EC50 (nM) | Conc. (ug/ml) |
|---|---|---|---|---|
| Chimeric VH | Chimeric VL | 1.559 | 10.393 | 41.306 |
| VH1 | VL1 | 1.721 | 11.473 | 55.221 |
| | VL2 | 2.194 | 14.627 | 59.428 |
| | VL3 | 2.275 | 15.167 | 62.745 |
| VH2 | VL1 | 5.368 | 35.787 | 30.627 |
| | VL2 | 4.816 | 32.107 | 69.344 |
| | VL3 | 8.350 | 55.667 | 26.803 |
| VH3 | VL1 | 4.185 | 27.900 | 92.136 |
| | VL2 | 2.929 | 19.527 | 75.827 |
| | VL3 | 2.824 | 18.827 | 59.179 |
| VH4 | VL1 | 2.393 | 15.953 | 61.875 |
| | VL2 | 1.985 | 13.233 | 61.475 |
| | VL3 | 1.974 | 13.160 | 36.892 |
| VH5 | VL1 | 0.375 | 2.502 | 31.433 |
| | VL2 | 1.611 | 10.740 | 58.791 |
| | VL3 | 1.927 | 12.847 | 43.835 |

TABLE 4-continued

| Humanized Antibody | | EC50 (μg/ml) | EC50 (nM) | Conc. (ug/ml) |
|---|---|---|---|---|
| VH6 | VL1 | 1.448 | 9.653 | 33.976 |
| | VL2 | 1.943 | 12.953 | 48.933 |
| | VL3 | 2.863 | 19.087 | 41.491 |

Three IgGs (VH1/VL1), (VH1/VL2) and (VH1/VL3) were selected for expression in the Expi293F cell culture. The recombinant plasmids encoding target IgG were transiently co-transfected and the supernatants were purified with protein A affinity column. The purified antibody was buffer exchanged into PBS using dialysis bag. The concentration and purity of the purified protein were determined by OD280 and SDS-PAGE, respectively. Evaluating from the SDS-PAGE, the purity of humanized IgGs were >95%. Binding confirmation were tested by FACS Calibur (BD Bioscience, San Jose, Calif.).

The HC and LC amino acid sequences for the 3 selected humanized CXCR4 antibodies are summarized in Table 5:

TABLE 5

| Humanized IgG | HC | LC |
|---|---|---|
| 1 (VH1/VL1) | SEQ ID NO: 33 | SEQ ID NO: 35 |
| 2 (VH1/VL2) | SEQ ID NO: 33 | SEQ ID NO: 37 |
| 3 (VH1/VL3) | SEQ ID NO: 33 | SEQ ID NO: 39 |

Figure 4:
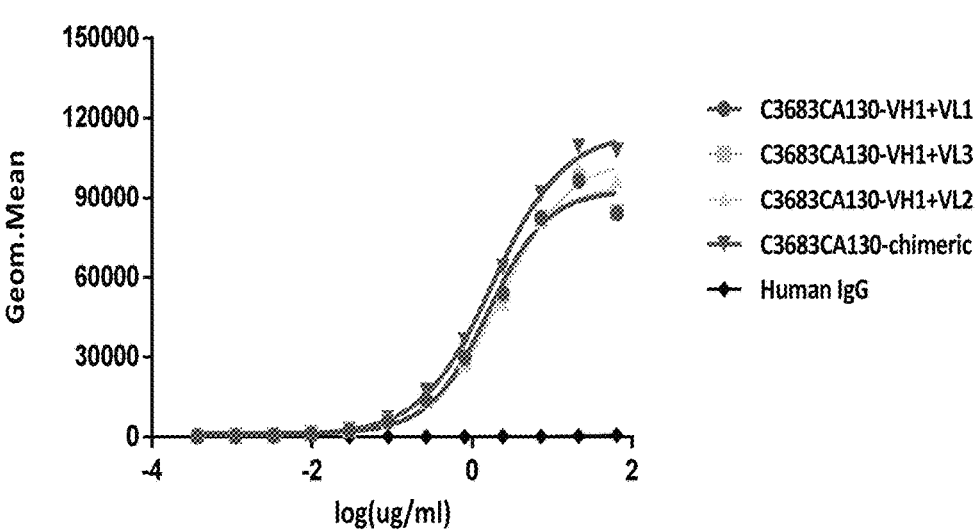
FIG. 4 is line graph depicting the FACS binding assay data for various CXCR4 humanized antibodies.

The FACS binding data is summarized in FIG. 4 and Table 6 below:

TABLE 6

| Humanized IgG | EC50 (μg/ml) |
|---|---|
| 1 (VH1/VL1) | 1.599 |
| 2 (VH1/VL2) | 1.718 |
| 3 (VH1/VL3) | 2.345 |
| 4 Chimeric (VH/VL) | 1.799 |

Various monoclonal antibodies were assessed in recombinant CHO cells stably expressing CXCR4 receptors using a CAMP assay (Dynamic CAMP Assay, Cisbio). Recombinant CHO cells expressing tagged CXCR4 receptors were added to 96-well half-area white plates (40,000 cells per well) and were treated with SDF-1 at concentrations from 0.5 pM to 100 nM and with Forskolin at 500 nM to assess agonist activity. To assess antagonist activity, CXCR4 mAb were added to cells at 0.5 pM to 1 μM for 30 min at room temperature. 5.0 nM of SDF-1 corresponding to the EC80, was then added and cells were further incubated for 30 min at room temperature. The reaction was stopped by adding detection mix to all wells followed by a 60 min incubation at room temperature. The assay plates were read on an EnVision® Multilabel Plate Reader (PerkinElmer; Waltham, MA, USA) at an emission wavelength of 665 nm. The maximal CAMP accumulation response (considered 100% of control) was measured from wells containing agonist only (the highest concentration of SDF-1 for agonist curves). Measurements from wells also containing antagonist were normalized to the maximal control value and expressed as percentage of control (POC). Wells containing assay buffer without test compounds were considered 0%. All results were analyzed by nonlinear regression curve fit using GraphPad Prism™ version 6 (GraphPad Inc., La Jolla, CA).

Figure 5:
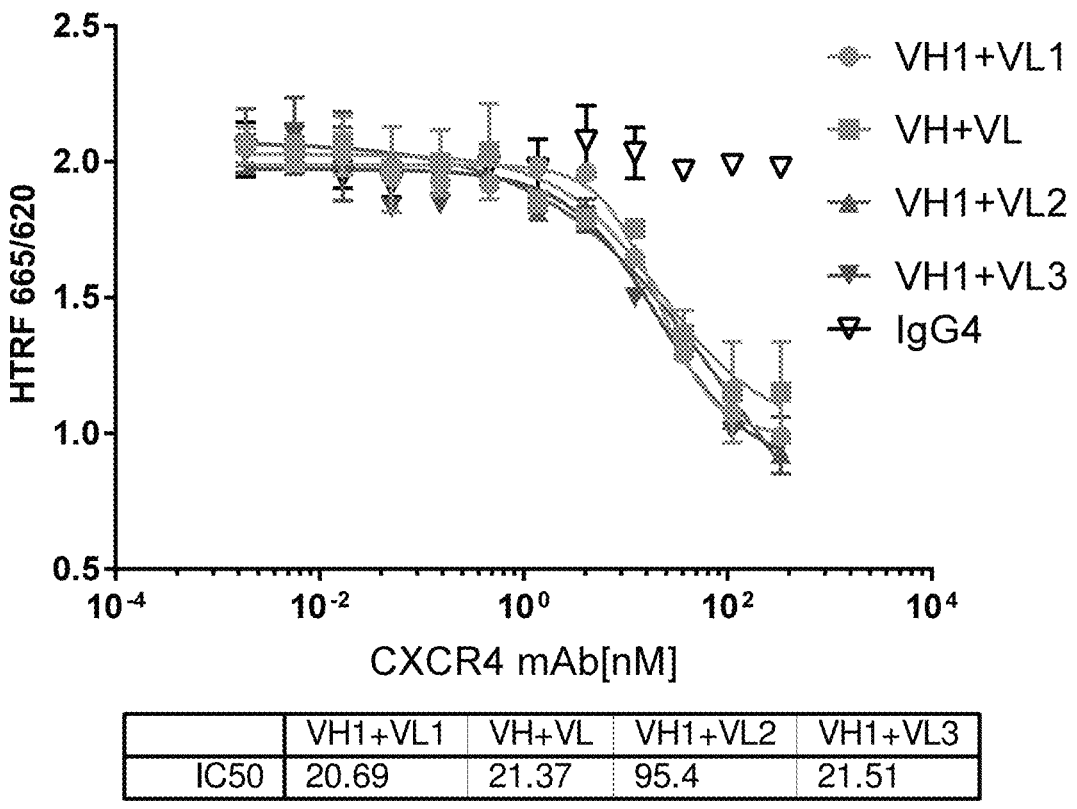
FIG. 5 is line graph depicting the binding assay data for various CXCR4 humanized antibodies.

The binding data is summarized in FIG. 5 and Table 7 below:

TABLE 7

| Humanized IgG | IC50 |
|---|---|
| 1 (VH1/VL1) | 20.69 |
| 2 (VH1/VL2) | 95.40 |
| 3 (VH1/VL3) | 21.51 |
| 4 Chimeric (VH/VL) | 21.37 |

All of the articles and methods disclosed and claimed herein can be made and executed without undue experimentation in light of the present disclosure. While the articles and methods of this invention have been described in terms of preferred embodiments, it will be apparent to those of skill in the art that variations may be applied to the articles and methods without departing from the spirit and scope of the invention. All such variations and equivalents apparent to those skilled in the art, whether now existing or later developed, are deemed to be within the spirit and scope of the invention as defined by the appended claims. All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes. The invention illustratively described herein suitably may be practiced in the absence of any element(s) not specifically disclosed herein. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Sequence Listings

The nucleic and amino acid sequences listed in the accompanying sequence listing are shown using standard letter abbreviations for nucleotide bases and three letter code for amino acids, as defined in 37 C.F.R. 1.822.

SEQ ID NO: 1 is an amino acid sequence comprising a human CXCR4.

SEQ ID NOs: 2-3 are the amino acid sequence of a heavy chain CDR1 in a monoclonal antibody which specifically binds CXCR4.

SEQ ID NOs: 4-5 are the amino acid sequences of a heavy chain CDR2 in a monoclonal antibody which specifically binds CXCR4.

SEQ ID NOs: 6-7 are the amino acid sequences of a heavy chain CDR3 in a monoclonal antibody which specifically binds CXCR4.

SEQ ID NOs: 8-9 are the amino acid sequences of a light chain CDR1 in a monoclonal antibody which specifically binds CXCR4.

SEQ ID NO: 10-11 is the amino acid sequences of a light chain CDR2 in a monoclonal antibody which specifically binds CXCR4.

SEQ ID NOs: 12-13 are the amino acid sequences of a light chain CDR3 in a monoclonal antibody which specifically binds CXCR4.

SEQ ID NOs: 14 and 16 are amino acid sequences of a heavy chain variable region of murine monoclonal antibodies which specifically bind CXCR4.

SEQ ID NOs: 15 and 17 are nucleic acid sequences encoding a heavy chain variable region of murine monoclonal antibodies which specifically bind CXCR4.

SEQ ID NOs: 18 and 20 are amino acid sequences of a light chain variable region of murine monoclonal antibodies which specifically bind CXCR4.

SEQ ID NOs: 19 and 21 are nucleic acid sequences encoding a light chain variable region of murine monoclonal antibodies which specifically bind CXCR4.

SEQ ID NO: 22 is the amino acid sequence of a heavy chain variable region of a murine-human chimeric antibody which specifically binds CXCR4.

SEQ ID NO: 23 is the amino acid sequence of a light chain variable region of a murine-human chimeric antibody which specifically binds CXCR4.

SEQ ID NOs: 24-29 are amino acid sequences of a heavy chain variable regions of humanized monoclonal antibodies which specifically binds CXCR4.

SEQ ID NOs: 30-32 are amino acid sequences of a light chain variable regions of humanized monoclonal antibodies which specifically binds CXCR4.

SEQ ID NO: 33 is the amino acid sequence of a heavy chain of humanized monoclonal antibodies which specifically binds CXCR4.

SEQ ID NOs: 34 is the nucleic acid sequence of a heavy chain of humanized monoclonal antibodies which specifically binds CXCR4.

SEQ ID NOs: 35, 37 and 39 are amino acid sequences of a light chain of humanized monoclonal antibodies which specifically binds CXCR4.

SEQ ID NOs: 36, 38 and 40 are nucleic acid sequences of a light chain of humanized monoclonal antibodies which specifically binds CXCR4.

SEQ ID NOs: 41 and 42 are the amino acid sequences of a light chain constant region of a monoclonal antibody which specifically binds CXCR4.

SEQ ID NO: 43 is the amino acid sequence of a heavy chain constant region of a monoclonal antibody which specifically binds CXCR4.

```
SEQUENCE LISTINGS
CXCR4 amino acid sequence
                                    SEQ ID NO: 1
MEGISSIPLPLLQIYTSDNYTEEMGSGDYDSMKEP

CFREENANFNKIFLPTIYSIIFLTGIVGNGLVILV

MGYQKKLRSMTDKYRLHLSVADLLFVITLPFWAVD

AVANWYFGNFLCKAVHVIYTVNLYSSVLILAFISL

DRYLAIVHATNSQRPRKLLAEKVVYVGVWIPALLL

TIPDFIFANVSEADDRYICDRFYPNDLWVVVFQFQ

HIMVGLILPGIVILSCYCIIISKLSHSKGHQKRKA

LKTTVILILAFFACWLPYYIGISIDSFILLEIIKQ

GCEFENTVHKWISITEALAFFHCCLNPILYAFLGA

KFKTSAQHALTSVSRGSSLKILSKGKRGGHSSVST

ESESSSFHSS
```

-continued

```
Murine monoclonal antibody heavy chain CDR1
amino acid sequence
                                    SEQ ID NO: 2
SSGMH Murine monoclonal antibody heavy chain CDR1
amino acid sequence
                                    SEQ ID NO: 3
GYAFTDFHLN Murine monoclonal antibody heavy chain CDR2
amino acid sequence
                                    SEQ ID NO: 4
YISSGSSSIYYADTVKG Murine monoclonal antibody heavy chain CDR2
amino acid sequence
                                    SEQ ID NO: 5
VINPYNGGTNYNQKFKD Murine monoclonal antibody heavy chain CDR3
amino acid sequence
                                    SEQ ID NO: 6
PYYYGSIAMDY Murine monoclonal antibody heavy chain CDR3
amino acid sequence
                                    SEQ ID NO: 7
YYASRYGYAMDY Murine monoclonal antibody light chain CDR1
                                    SEQ ID NO: 8
amino acid sequence
KASQDINSYLS Murine monoclonal antibody light chain CDR1
                                    SEQ ID NO: 9
amino acid sequence
RSSKSLLHSNGNTYLY Murine monoclonal antibody light chain CDR2
amino acid sequence
                                    SEQ ID NO: 10
RANRLVD Murine monoclonal antibody light chain CDR2
amino acid sequence
                                    SEQ ID NO: 11
RMSNLAS Murine monoclonal antibody light chain CDR3
amino acid sequence
                                    SEQ ID NO: 12
LQYDEFPFT Murine monoclonal antibody light chain CDR3
amino acid sequence
                                    SEQ ID NO: 13
MQHVEYPLT Murine monoclonal antibody heavy chain
variable region amino acid sequence
                                    SEQ ID NO: 14
DVQLVESGGGLVQPGGSRKLSCAASGFTFSSSGMHWVRQA

PEKGLEWVAYISSGSSSIYYADTVKGRFTISRDNPKNTLF

LQMTSLRSEDTAMYYCARPYYYGSIAMDYWGQGTSVTVSS

Murine monoclonal antibody heavy chain
variable region nucleic acid sequence
                                    SEQ ID NO: 15
gatgtgcagctggtggagtctggggggaggcttagtgcagc ctggagggtcccggaaactctcctgtgcagcctctggatt cactttcagtagctctggaatgcactgggttcgtcaggct ccagagaagggactggagtgggtcgcatacattagtagtg
```

-continued gcagtagttccatctactatgcagacacagtgaagggccg attcaccatctccagagacaatcccaagaacaccctgttc ttgcaaatgaccagtctaaggtctgaggacacggccatgt attactgtgcaagaccttattactacggctccattgctat ggactactgggtcaaggaacctcagtcaccgtctcctca Murine monoclonal antibody heavy chain
variable region amino acid
sequence
SEQ ID NO: 16
EVQLQQSGPVLVRPGASVKMSCKASGYAFTDFHLNWVKQS

HGKSLEWIGVINPYNGGTNYNQKFKDKATLTVDKSSSTAY

MELNRLTSEDSAVYYCARYYASRYGYAMDYWGQGTSVTVS

S

Murine monoclonal antibody heavy chain
variable region nucleic acid
sequence
SEQ ID NO: 17
gaggtccaactgcaacagtctggacctgtgctggtgaggc ctggggcttcagtgaagatgtcctgtaaggcttctggata cgcattcactgacttccatttgaactgggtgaagcagagc catggaaagagccttgagtggattggagttattaatcctt acaacggtggtactaactacaaccagaagttcaaggacaa ggccacattgactgttgacaagtcctccagcacagcctac atggagctcaacagactgacatctgaggactctgcagtct attactgtgcaagatactacgctagtaggtacggctatgc tatggactactgggtcaaggaacctcagtcaccgtctcc tca Murine monoclonal antibody light chain
variable region amino acid sequence
SEQ ID NO: 18
DIKMTQSPSSMYASLGERVTITCKASQDINSYLSWFQQKP

GKSPKTLIYRANRLVDGVPSRFSGSGSGQDYSLTISSLEY

EDMGIYYCLQYDEFPFTFGSGTKLEIK

Murine monoclonal antibody light chain
variable region nucleic acid sequence
SEQ ID NO: 19
gacatcaagatgacccagtctccatcttccatgtatgcat ctctaggagagagtcactatcacttgcaaggcgagtca ggacattaatagctatttaagctggttccagcagaaacca gggaaatctcctaagaccctgatctatcgtgcaaacagat tggtagatggggtcccatcaaggttcagtggcagtggatc tgggcaagattattctctcaccatcagcagcctggagtat gaagatatgggaatttattattgtctacagtatgatgagt ttccattcacgttcggctcggggacaaagttggaaataaa a -continued Murine monoclonal antibody light chain
variable region
amino acid sequence
SEQ ID NO: 20
DIVMTQAAPSVPVTPGESVSISCRSSKSLLHSNGNTYLYW

FLQRPGQSPQLLIYRMSNLASGVPDRFSGSGSGTAFTLRI

SRVEAEDVGIYYCMQHVEYPLTFGAGTKLELK

Murine monoclonal antibody light chain
variable region nucleic acid sequence
SEQ ID NO: 21
gatattgtgatgactcaggctgcaccctctgtacctgtca ctcctggagagtcagtatccatctcctgcaggtctagtaa gagtctcctgcatagtaatggcaacacttacttgtattgg ttcctgcagaggccaggccagtctcctcagctcctgatat atcggatgtccaaccttgcctcaggagtcccagacaggtt cagtggcagtgggtcaggaactgctttcacactgagaatc agtagagtggaggctgaggatgtgggtatttattattgta tgcaacatgtagaatatcctctcacgttcggtgctgggac caagctggagctgaaa Heavy chain amino acid sequence
of a murine-human chimeric antibody
SEQ ID NO: 22
MGWSCIILFLVATATGVHSEVQLQQSGPVLVRPGASVKMS

CKASGYAFTDFHLNWVKQSHGKSLEWIGVINPYNGGTNYN

QKFKDKATLTVDKSSSTAYMELNRLTSEDSAVYYCARYYA

SRYGYAMDYWGQGTSVTVSSASTKGPSVFPLAPSSKSTSG

GTAALGCLVKDYFPEPVTVSWNSGALTSGVHTFPAVLQSS

GLYSLSSVVTVPSSSLGTQTYICNVNHKPSNTKVDKKVEP

KSCDKTHTCPPCPAPELLGGPSVFLFPPKPKDTLMISRTP

EVTCVVVDVSHEDPEVKFNWYVDGVEVHNAKTKPREEQYN

STYRVVSVLTVLHQDWLNGKEYKCKVSNKALPAPIEKTIS

KAKGQPREPQVYTLPPSRDELTKNQVSLTCLVKGFYPSDI

AVEWESNGQPENNYKTTPPVLDSDGSFFLYSKLTVDKSRW

QQGNVFSCSVMHEALHNHYTQKSLSLSPGK

Light chain
amino acid sequence of a murine-human
chimeric antibody
SEQ ID NO: 23
MGWSCIILFLVATATGVHSDIVMTQAAPSVPVTPGESVSI

SCRSSKSLLHSNGNTYLYWFLQRPGQSPQLLIYRMSNLAS

GVPDRFSGSGSGTAFTLRISRVEAEDVGIYYCMQHVEYPL

TFGAGTKLELKRTVAAPSVFIFPPSDEQLKSGTASVVCLL

NNFYPREAKVQWKVDNALQSGNSQESVTEQDSKDSTYSLS

STLTLSKADYEKHKVYACEVTHQGLSSPVTKSFNRGEC

Humanized heavy chain
variable region amino acid sequence
SEQ ID NO: 24
QVQLVQSGAEVKKPGASVKVSCKASGYAFTDFHLNWVRQA

PGQGLEWMGVINPYNGGTNYNQKFKDRVTMTRDTSISTAY

MELSRLRSDDTAVYYCARYYASRYGYAMDYWGQGTLVTVS

S

Humanized heavy chain
variable region amino acid sequence
SEQ ID NO: 25
QVQLVQSGAEVKKPGASVKVSCKASGYAFTDFHLNWVRQS

PGQGLEWIGVINPYNGGTNYNQKFKDRVTLTVDTSISTAY

MELSRLRSDDTAVYYCARYYASRYGYAMDYWGQGTLVTVS

S

Humanized heavy chain
variable region amino acid sequence
SEQ ID NO: 26
QVQLVQSGAEVKKPGASVKVSCKASGYAFTDFHLNWVRQS

HGQGLEWIGVINPYNGGTNYNQKFKDRVTLTVDTSISTAY

MELSRLRSDDTAVYYCARYYASRYGYAMDYWGQGTLVTVS

S

Humanized heavy chain
variable region amino acid sequence
SEQ ID NO: 27
QVQLVQSGAEVKKPGASVKMSCKASGYAFTDFHLNWVRQS

HGQGLEWIGVINPYNGGTNYNQKFKDRVTLTVDTSISTAY

MELSRLRSDDTAVYYCARYYASRYGYAMDYWGQGTLVTVS

S

Humanized heavychain
variable region amino acid sequence
SEQ ID NO: 28
QVQLVQSGAEVKKPGASVKMSCKASGYAFTDFHLNWVKQS

HGQGLEWIGVINPYNGGTNYNQKFKDRVTLTVDTSISTAY

MELSRLRSDDTAVYYCARYYASRYGYAMDYWGQGTLVTVS

S

Humanized heavy chain
variable region amino acid sequence
SEQ ID NO: 29
QVQLVQSGAEVKKPGASVKMSCKASGYAFTDFHLNWVKQS

HGQGLEWIGVINPYNGGTNYNQKFKDRATLTVDTSISTAY

MELSRLRSDDSAVYYCARYYASRYGYAMDYWGQGTLVTVS

S

Humanized light chain variable region
amino acid sequence
SEQ ID NO: 30
DIVMTQSPLSLPVTPGEPASISCRSSKSLLHSNGNTYLYW

YLQKPGQSPQLLIYRMSNLASGVPDRFSGSGSGTDFTLKI

SRVEAEDVGVYYCMQHVEYPLTFGGGTKLEIK

Humanized light chain variable region
amino acid sequence
SEQ ID NO: 31
DIVMTQSPLSLPVTPGEPVSISCRSSKSLLHSNGNTYLYW

FLQKPGQSPQLLIYRMSNLASGVPDRFSGSGSGTDFTLKI

SRVEAEDVGVYYCMQHVEYPLTFGGGTKLEIK

Humanized light chain
variable region amino acid sequence
SEQ ID NO: 32
DIVMTQSALSLPVTPGEPVSISCRSSKSLLHSNGNTYLYW

FLQKPGQSPQLLIYRMSNLASGVPDRFSGSGSGTDFTLKI

SRVEAEDVGVYYCMQHVEYPLTFGGGTKLEIK

Humanized heavy chain amino acid sequence
SEQ ID NO: 33
QVQLVQSGAEVKKPGASVKVSCKASGYAFTDFHLNWVRQA

PGQGLEWMGVINPYNGGTNYNQKFKDRVTMTRDTSISTAY

MELSRLRSDDTAVYYCARYYASRYGYAMDYWGQGTLVTVS

SASTKGPSVFPLAPSSKSTSGGTAALGCLVKDYFPEPVTV

SWNSGALTSGVHTFPAVLQSSGLYSLSSVVTVPSSSLGTQ

TYICNVNHKPSNTKVDKKVEPKSCDKTHTCPPCPAPELLG

GPSVFLFPPKPKDTLMISRTPEVTCVVVDVSHEDPEVKFN

WYVDGVEVHNAKTKPREEQYNSTYRVVSVLTVLHQDWLNG

KEYKCKVSNKALPAPIEKTISKAKGQPREPQVYTLPPSRD

ELTKNQVSLTCLVKGFYPSDIAVEWESNGQPENNYKTTPP

VLDSDGSFFLYSKLTVDKSRWQQGNVFSCSVMHEALHNHY

TQKSLSLSPGK

Humanized heavy chain nucleic acid sequence
SEQ ID NO: 34
caggtgcagctggtgcagagcggagcagaggtgaagaagc caggagcctccgtgaaggtgtcttgcaaggccagcggcta cgccttcaccgactttcacctgaactgggtgcggcaggca ccaggacagggactggagtggatgggcgtgatcaaccctt acaatggcggcacaaactataatcagaagttcaaggacag ggtgaccatgacacgcgatacctctatcagcacagcctac atggagctgtcccggctgagatctgacgataccgccgtgt actattgtgcccggtactatgcctccagatacggctatgc catggattattggggccagggcaccctggtgacagtgagc tccgccagcaccaaggggcccttccgtgtttccactggccc cctcctctaaatccacatctggcggcaccgccgccctggg ctgtctggtgaaggactacttcccagagcctgtgacagtg tcctggaactctggcgccctgacatccggcgtgcacacat ttccagccgtgctgcagagctccggcctgtacagcctgtc tagcgtggtgacagtgccctcctctagcctgggcacacag acctatatctgcaacgtgaatcacaagccaagcaatacca aggtggacaagaaggtggagcccaagtcctgtgataagac -continued acacacctgccccccttgtcctgctcccgagctgctgggc ggccctagcgtgttcctgtttccacccaagcctaaggaca ccctgatgatctcccggacacccgaggtgacctgcgtggt ggtggacgtgtctcacgaggatcctgaggtgaagttcaac tggtatgtggatggcgtggaggtgcacaatgccaagacca agcccagagaggagcagtacaactctacatataagggtggt gagcgtgctgaccgtgctgcaccaggactggctgaacggc aaggagtataagtgcaaggtgtccaataaggccctgcccg cccccatcgagaagacaatcagcaaggccaagggccagcc tcgggagccacaggtgtacaccctgcctccatccagagac gagctgacaaagaaccaggtgtctctgacatgtctggtga agggcttctatcctagcgatatcgccgtggagtgggagtc caatggccagccagagaacaattacaagaccacacccct gtgctggactccgatggctccttctttctgtattccaagc tgaccgtggataagtctcggtggcagcagggcaacgtgtt cagctgttccgtgatgcacgaagccctgcataatcactat actcagaaatccctgtccctgtcacctggaaagtga Humanized light chain amino acid sequence

SEQ ID NO: 35

DIVMTQSPLSLPVTPGEPASISCRSSKSLLHSNGNTYLYW

YLQKPGQSPQLLIYRMSNLASGVPDRFSGSGSGTDFTLKI

SRVEAEDVGVYYCMQHVEYPLTFGGGTKLEIKRTVAAPSV

FIFPPSDEQLKSGTASVVCLLNNFYPREAKVQWKVDNALQ

SGNSQESVTEQDSKDSTYSLSSTLTLSKADYEKHKVYACE

VTHQGLSSPVTKSFNRGEC

Humanized light chain nucleic acid sequence

SEQ ID NO: 36 gacatcgtgatgacccagtcccctctgtctctgcccgtga cacctggcgagccagcctctatcagctgcaggagctccaa gagcctgctgcactccaacggcaataacctacctgtattgg tacctgcagaagcccggccagtcccctcagctgctgatct atcggatgtctaacctggccagcggcgtgccagacagatt ctccggatctggaagcggaaccgacttcaccctgaagatc tctcgggtggaggccgaggatgtgggcgtgtactattgta tgcagcacgtggagtacccactgaccttcggcggaggaac aaagctggagatcaagaggacagtggccgcccccaagcgtg ttcatctttcccccttccgacgagcagctgaagtctggca ccgccagcgtggtgtgcctgctgaacaacttctaccctcg ggaggccaaggtccagtggaaggtggataacgccctgcag -continued tctggcaatagccaggagtccgtgaccgagcaggactcta aggatagcacatattccctgtctagcaccctgacactgag caaggccgattacgagaagcacaaggtgtatgcctgtgaa gtcacccatcaggggctgtcatcacccgtcactaagtcat tcaatcgcggagaatgctag Humanized light chain amino acid sequence

SEQ ID NO: 37

DIVMTQSPLSLPVTPGEPVSISCRSSKSLLHSNGNTYLYW

FLQKPGQSPQLLIYRMSNLASGVPDRFSGSGSGTDFTLKI

SRVEAEDVGVYYCMQHVEYPLTFGGGTKLEIKRTVAAPSV

FIFPPSDEQLKSGTASVVCLLNNFYPREAKVQWKVDNALQ

SGNSQESVTEQDSKDSTYSLSSTLTLSKADYEKHKVYACE

VTHQGLSSPVTKSFNRGEC

Humanized light chain nucleic acid sequence

SEQ ID NO: 38 gacatcgtgatgacccagtcccctctgtctctgcccgtga cacctggcgagccagtgtctatcagctgcaggagctccaa gagcctgctgcactccaacggcaataacctacctgtattgg ttcctgcagaagcccggccagtcccctcagctgctgatct accggatgtctaacctggccagcggcgtgccagacagatt ctccggatctggaagcggaaccgacttcaccctgaagatc tctcgggtggaggccgaggatgtgggcgtgtactattgta tgcagcacgtggagtatcccctgacctttggcggcggcac aaagctggagatcaagaggacagtggccgcccccaagcgtg ttcatctttcccccttccgacgagcagctgaagtctggca ccgccagcgtggtgtgcctgctgaacaacttctaccctcg ggaggccaaggtccagtggaaggtggataacgccctgcag tctggcaatagccaggagtccgtgaccgagcaggactcta aggatagcacatattccctgtctagcaccctgacactgag caaggccgattacgagaagcacaaggtgtatgcctgtgaa gtcacccatcaggggctgtcatcacccgtcactaagtcat tcaatcgcggagaatgctag Humanized heavy chain amino acid sequence

SEQ ID NO: 39

DIVMTQSALSLPVTPGEPVSISCRSSKSLLHSNGNTYLYW

FLQKPGQSPQLLIYRMSNLASGVPDRFSGSGSGTDFTLKI

SRVEAEDVGVYYCMQHVEYPLTFGGGTKLEIKRTVAAPSV

FIFPPSDEQLKSGTASVVCLLNNFYPREAKVQWKVDNALQ

SGNSQESVTEQDSKDSTYSLSSTLTLSKADYEKHKVYACE

VTHQGLSSPVTKSFNRGEC

Humanized heavy chain nucleic acid sequence

SEQ ID NO: 40 gacatcgtgatgacccagtccgccctgtctctgccagtga cacctggagagccagtgtctatcagctgcaggagctccaa -continued

```
gagcctgctgcactccaacggcaatacctacctgtattgg ttcctgcagaagcccggccagtcccctcagctgctgatct accggatgtctaacctggccagcggcgtgccagacagatt ctccggatctggaagcggaaccgacttcaccctgaagatc tctcgggtggaggccgaggatgtgggcgtgtactattgta tgcagcacgtggagtatcccctgacctttggcggcggcac aaagctggagatcaagaggacagtggccgcccccaagcgtg ttcatctttccccccttccgacgagcagctgaagtctggca ccgccagcgtggtgtgcctgctgaacaacttctaccctcg ggaggccaaggtccagtggaaggtggataacgccctgcag tctggcaatagccaggagtccgtgaccgagcaggactcta aggatagcacatattccctgtctagcaccctgacactgag caaggccgattacgagaagcacaaggtgtatgcctgtgaa gtcacccatcaggggctgtcatcacccgtcactaagtcat tcaatcgcggagaatgctag
```

Light chain constant region amino acid sequence
SEQ ID NO: 41
RTVAAPSVFIFPPSDEQLKSGTASVVCLLNNFYPREAKVQ

WKVDNALQSGNSQESVTEQDSKDSTYSLSSTLTLSKADYE

KHKVYACEVTHQGLSSPVTKSFNRGEC

Light chain constant region amino acid sequence
SEQ ID NO: 42
GQPKAAPSVTLFPPSSEELQANKATLVCLISDFYPGAVTV

AWKADSSPVKAGVETTTPSKQSNNKYAASSYLSLTPEQWK

SHRSYSCQVTHEGSTVEKTVAPTECS

Heavy chain constant region amino acid sequence
SEQ ID NO: 43
ASTKGPSVFPLAPSSKSTSGGTAALGCLVKDYFPEPVTVS

WNSGALTSGVHTFPAVLQSSGLYSLSSVVTVPSSSLGTQT

YICNVNHKPSNTKVDKKVEPKSCDKTHTCPPCPAPELLGG

PSVFLFPPKPKDTLMISRTPEVTCVVVDVSHEDPEVKFNW

YVDGVEVHNAKTKPREEQYNSTYRVVSVLTVLHQDWLNGK

EYKCKVSNKALPAPIEKTISKAKGQPREPQVYTLPPSRDE

LTKNQVSLTCLVKGFYPSDIAVEWESNGQPENNYKTTPPV

LDSDGSFFLYSKLTVDKSRWQQGNVFSCSVMHEALHNHYT

QKSLSLSPGK

What is claimed is:

1. An isolated antibody or antigen-binding fragment thereof which specifically binds human Chemokine receptor 4 (CXCR4) and comprises: the light chain CDR1, CDR2, and CDR3 sequences set forth in SEQ ID NO: 9, SEQ ID NO: 11 and SEQ ID NO: 13 and the heavy chain CDR1, CDR2, and CDR3 sequences set forth in SEQ ID NO: 3, SEQ ID NO: 5, and SEQ ID NO: 7.

2. An isolated antibody or antigen-binding fragment thereof according to claim 1, further comprising a set of four variable region framework regions from a human immunoglobulin (IgG).

3. An isolated antibody or antigen-binding fragment thereof according to claim 1 that binds to CXCR4 protein with a dissociation constant ($K_D$) of at least about $1 \times 10^{-6}$ M, at least about $1 \times 10^{-7}$ M, at least about $1 \times 10^{-8}$ M, at least about $1 \times 10^{-9}$ M, at least about $1 \times 10^{-10}$ M, at least about $1 \times 10^{-11}$ M, or at least about $1 \times 10^{-12}$ M.

4. An isolated antibody or antigen-binding fragment thereof according to claim 1 wherein the antibody or antigen-binding fragment is selected from a human antibody, a humanized antibody, chimeric antibody, a monoclonal antibody, a polyclonal antibody, a recombinant antibody, an antigen-binding antibody fragment, a single chain antibody, a diabody, a triabody, a tetrabody, a Fab fragment, a Fab' fragment, a $Fab_2$ fragment, a F (ab)'$_2$ fragment, a domain antibody, an IgD antibody, an IgE antibody, an IgM antibody, an IgG1 antibody, an IgG2 antibody, an IgG3 antibody, an IgG4 antibody, or an IgG4 antibody having at least one mutation in the hinge region that alleviates a tendency to form intra H-chain disulfide bonds.

5. An isolated humanized antibody or antigen-binding fragment thereof that specifically binds human CXCR4 and comprises a heavy chain variable region sequence selected from the group consisting of SEQ ID NOs: 24-29, and a light chain variable region sequence selected from the group consisting of SEQ ID NOs: 30-32.

6. An isolated humanized antibody or antigen-binding fragment thereof according to claim 5 which comprises the heavy chain sequence set forth in SEQ ID NO: 33, and the light chain sequence set forth in SEQ ID NO: 35.

7. An isolated humanized antibody or antigen-binding fragment thereof according to claim 5 which comprises the heavy chain sequence set forth in SEQ ID NO: 33, and the light chain sequence set forth in SEQ ID NO: 37.

8. An isolated humanized antibody or antigen-binding fragment thereof according to claim 5 which comprises the heavy chain sequence set forth in SEQ ID NO: 33, and the light chain sequence set forth in SEQ ID NO: 39.

9. A pharmaceutical composition comprising an isolated antibody or antigen-binding fragment thereof according to claim 1 in admixture with a pharmaceutically acceptable carrier.

10. A method of treating a subject suffering from a CXCR4-associated disorder, comprising administering to said subject a therapeutically effective amount of the pharmaceutical composition of claim 9.

11. An isolated immunoconjugate or fusion protein comprising an antibody or antigen-binding fragment thereof according to claim 1 coupled to an effector molecule.

12. An isolated nucleic acid comprising a polynucleotide sequence encoding an antibody or antigen-binding fragment thereof according to claim 1.

13. A recombinant expression vector comprising the isolated nucleic acid of claim 12.

14. A host cell comprising the vector of claim 13.

* * * * *